(12) United States Patent
Barzel et al.

(10) Patent No.: US 12,060,572 B2
(45) Date of Patent: Aug. 13, 2024

(54) RECOMBINATION ACTIVATING GENE (RAG) INDUCED V(D)J GENE TARGETING

(71) Applicant: Ramot at Tel-Aviv University Ltd., Tel-Aviv (IL)

(72) Inventors: Adi Barzel, Hod Hasharon (IL); Iris Dotan, Tel-Aviv (IL); Carmel Pundak-Mintz, Tel-Aviv (IL); Daniel Nataf, Tel-Aviv (IL); Miriam Fried, Tel-Aviv (IL); Natalia Gritsenko, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1304 days.

(21) Appl. No.: 16/606,240

(22) PCT Filed: Apr. 18, 2018

(86) PCT No.: PCT/IL2018/050443
§ 371 (c)(1),
(2) Date: Oct. 18, 2019

(87) PCT Pub. No.: WO2018/193457
PCT Pub. Date: Oct. 25, 2018

(65) Prior Publication Data
US 2020/0131540 A1 Apr. 30, 2020

Related U.S. Application Data

(60) Provisional application No. 62/487,799, filed on Apr. 20, 2017.

(51) Int. Cl.
*C12N 15/90* (2006.01)
*C07K 16/28* (2006.01)
*C12N 15/86* (2006.01)

(52) U.S. Cl.
CPC ........ *C12N 15/907* (2013.01); *C07K 16/2809* (2013.01); *C12N 15/86* (2013.01); *C07K 2317/14* (2013.01); *C07K 2317/24* (2013.01); *C07K 2317/76* (2013.01); *C12N 2510/00* (2013.01)

(58) Field of Classification Search
None
See application file for complete search history.

(56) References Cited

U.S. PATENT DOCUMENTS

2014/0283153 A1* 9/2014 Killeen .............. A01K 67/0275
800/9
2015/0329850 A1* 11/2015 Gallo .................. C07K 16/005
536/23.53

FOREIGN PATENT DOCUMENTS

| WO | WO-02077228 A1 | 10/2002 | |
|---|---|---|---|
| WO | WO-03046175 A1 | 6/2003 | |
| WO | WO-2009129247 A2 | 10/2009 | |
| WO | WO-2013134880 A1 | 9/2013 | |
| WO | WO-2014172489 A2 | 10/2014 | |
| WO | WO-2015072760 A1 | 5/2015 | |
| WO | WO-2017123804 A1 * | 7/2017 | ......... A01K 67/0275 |

OTHER PUBLICATIONS

Barzel, A., et al., "Promoterless Gene Targeting Without Nucleases Ameliorates Haemophilia B in Mice," Nature, 517(7534):360-364, Nature Publishing Group, England (2015).
Beatty, G.L., et al., "Mesothelin-specific Chimeric Antigen Receptor Mrna-engineered T Cells Induce Anti-tumor Activity in Solid Malignancies," Cancer Immunology Research, 2(2):112-120, American Association for Cancer Research, United States (2014).
Boutros, C., et al., "Safety Profiles of Anti-CTLA-4 and Anti-PD-1 Antibodies Alone and in Combination," Nature Reviews Clinical Oncology 13(8):473-486, Nature Publishing Group, England (2016).
Bryant, L.M., et al., "Lessons Learned From the Clinical Development and Market Authorization of Glybera," Human Gene Therapy. Clinical Development, 24(2):55-64, Mary Ann Liebert Inc. Publishers, United States (2013).
Chen, Z., et al., "Cross-neutralizing Human Anti-Poliovirus Antibodies Bind the Recognition Site for Cellular Receptor," Proceedings of the National Academy of Sciences of the United States of America, 110(50), 20242-20247, National Academy of Sciences, United States (2013).
Drug Bank, Rimiducid, Accession No. DB04974, Accessed at https://www.drugbank.ca/drugs/DB04974, 5 pages.
Fusil, F., et al., "A Lentiviral Vector Allowing Physiologically Regulated Membrane-anchored and Secreted Antibody Expression Depending on B-cell Maturation Status," Molecular Therapy, 23(11):1734-1747, Cell Press, United States (2015).
Garfall, A.L., et al., "Chimeric Antigen Receptor T Cells against CD19 for Multiple Myeloma," The New England Journal of Medicine, 373(11), 1040-1047 (2015).
Genbank, "Adeno-associated Virus—8, Complete Genome," Accession NC_006261.1, accessed at http://www.ncbi.nlm.nih.gov/nuccore/NC_006261, accessed on Aug. 13, 2018, 2 pages.
Genbank, "Adeno-associated virus 6, complete genome," Accession No. AF028704.1, accessed at https://www.ncbi.nlm.nih.gov/nuccore/AF028704, accessed on Jan. 12, 1998, 2 pages.

(Continued)

*Primary Examiner* — Kara D Johnson
*Assistant Examiner* — Maytee Marie Contes De Jesus
(74) *Attorney, Agent, or Firm* — Sterne Kessler Goldstein & Fox P.L.L.C.

(57) ABSTRACT

The present invention relates to methods for targeted insertion of at least one nucleic acid sequence/s of interest into a target genomic locus of a mammalian cell. More specifically, the methods of the invention are based on using nucleic acid cassettes comprising the nucleic acid sequence/s of interest and at least one recognition signal sequence (RSS), for insertion of the nucleic acid sequence of interest into the target genomic locus that is mediated by RAG-catalyzed recombination. The invention further provides cassettes, vectors and vehicles and cells comprising said cassettes, compositions and uses thereof in immunotherapy.

13 Claims, 18 Drawing Sheets
Specification includes a Sequence Listing.

(56) References Cited

OTHER PUBLICATIONS

GENPEPT., "V(D)J recombination-activating protein 1 [Mus musculus]," NCBI Reference Sequence: NP_033045.2, accessed on Dec. 10, 2019, 3 pages.

GENPEPT., "V(D)J recombination-activating protein 2 [*Homo sapiens*]," NCBI Reference Sequence: NP_001230715.1, accessed on Nov. 19, 2019, 3 pages.

GENPEPT., "V(D)J recombination-activating protein 2 [Mus musculus]," NCBI Reference Sequence: NP_033046.1, accessed on Dec. 10, 2019, 2 pages.

Hacein-Bey-Abina, S., et al., "Insertional Oncogenesis in 4 Patients After Retrovirus-mediated Gene Therapy of SCID-X1," The Journal of Clinical Investigation, 118(9):3132-3142, American Society for Clinical Investigation, United States (2008).

Liu, X., et al., "A Chimeric Switch-Receptor Targeting PD1 Augments the Efficacy of Second-Generation CAR T Cells in Advanced Solid Tumors," Cancer Research, 76(6):1578-1590, American Association for Cancer Research, United States (2016).

Luo, X.M., et al., "Engineering Human Hematopoietic Stem/progenitor Cells to Produce a Broadly Neutralizing Anti-HIV Antibody After in Vitro Maturation to Human B Lymphocytes," Blood, 113(7):1422-1431, American Society of Hematology, United States (2009).

Maude, S.L., et al., "Chimeric Antigen Receptor T Cells for Sustained Remissions in Leukemia," The New England Journal of Medicine, 371(16):1507-1517, Massachusetts Medical Society, United States (2014).

Moreau, A., et al., "Efficient Intrathymic Gene Transfer Following in Situ Administration of a Raav Serotype 8 Vector in Mice and Nonhuman Primates," Molecular Therapy, 17(3):472-479, Cell Press, United States (2009).

Nataf, D., et al., "Engineering T Cells and B Cells for Immunotherapy Using V(D)J Recombination," Department of Biochemistry and Molecular Biology, A35, Life Sciences Faculty, Tel-Aviv university, Tel-Aviv, 69978, Israel, P062, (2019).

Nataf, D., et al., "Engineering T Cells and B Cells for Immunotherapy Using V(D)J Recombination," Molecular Therapy, 25(5S1):25-26, (2017).

Poirot, L., et al., "Multiplex Genome-edited T-cell Manufacturing Platform for "Off-the-shelf" Adoptive T-cell Immunotherapies," Cancer Research, 75(18):3853-3864, American Association for Cancer Research, United States (2015).

Richter, M., et al., "In Vivo Transduction of Primitive Mobilized Hematopoietic Stem Cells After Intravenous Injection of Integrating Adenovirus Vectors," Blood, 128(18):2206-2217, American Society of Hematology, United States (2016).

Sather, B.D., et al., "Efficient Modification of CCR5 in Primary Human Hematopoietic Cells Using a MegaTAL Nuclease and AAV Donor Template," Science Translational Medicine, 7(307):307ra156, American Association for the Advancement of Science, United States (2015).

Schlereth, B., et al., "Potent Inhibition of Local and Disseminated Tumor Growth in Immunocompetent Mouse Models by a Bispecific Antibody Construct Specific for Murine CD3," Cancer Immunology, Immunotherapy, 55(7):785-796, Springer Verlag, Germany (2006).

Sharpe, M and Mount, N., "Genetically Modified T Cells in Cancer Therapy: Opportunities and Challenges," Disease Models & Mechanisms, 8(4):337-350, Company of Biologists Ltd, England (2015).

Themeli, M., et al., "Generation of Tumor-targeted Human T Lymphocytes From Induced Pluripotent Stem Cells for Cancer Therapy," Nature Biotechnology, 31(10):928-933, Nature America Publishing, United States (2013).

Zhao, Y., et al., "Extrathymic Generation of Tumor-specific T Cells From Genetically Engineered Human Hematopoietic Stem Cells via Notch Signaling," Cancer Research, 67(6):2425-2429, American Association for Cancer Research, United States (2007).

* cited by examiner

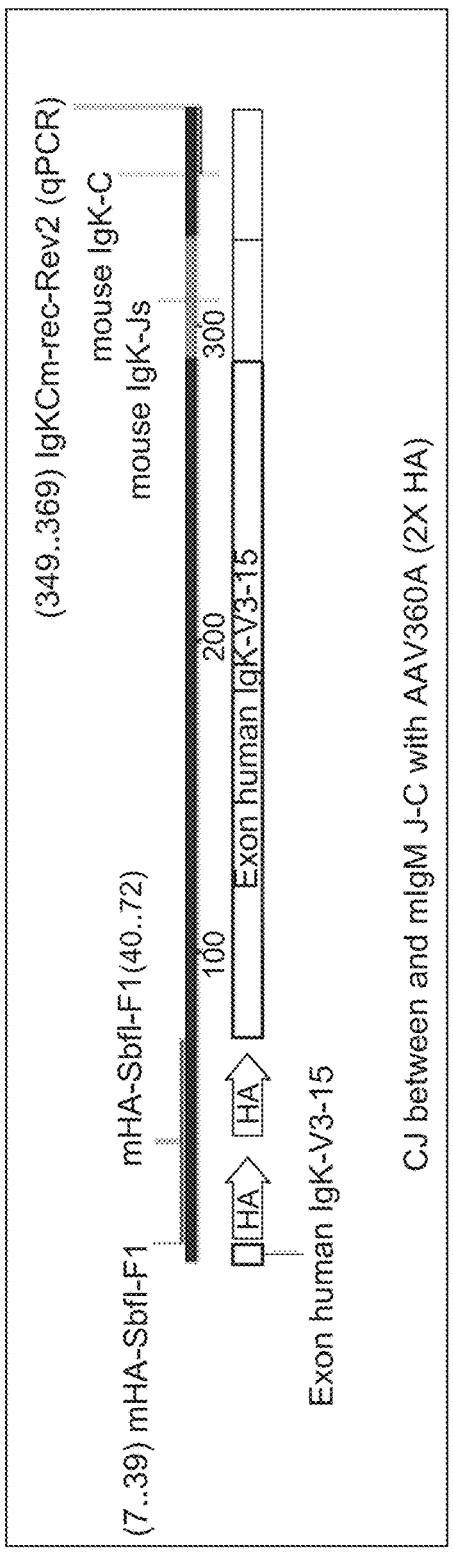
Fig. 3
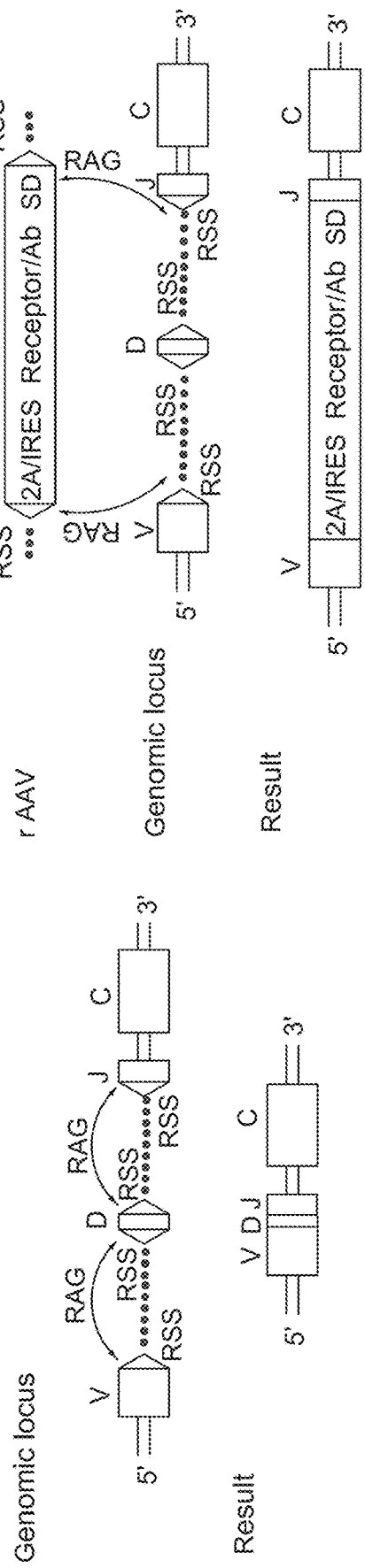
Fig. 4A
Fig. 4B 3 days of culturing without feeders and without cytokines

Fig. 17A coding joint diversity

Fig. 17B

Thymus of mouse No. 1
After extraction
Thymus of mouse No. 2
Before extraction
After extraction
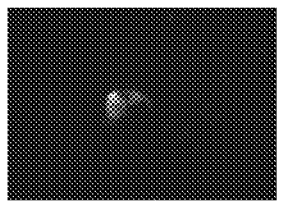 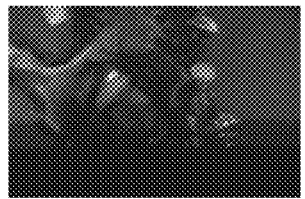 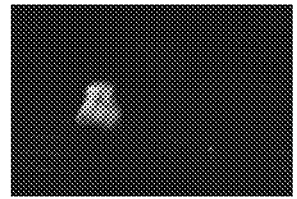
Fig. 18A    Fig. 18B    Fig. 18C
Mouse injected with fresh bone marrow cells transduced with a luciferase expressing retroviral vector
Mouse injected with Lin- enriched bone marrow cells transduced with a luciferase expressing retroviral vector
Control- non injected- mouse
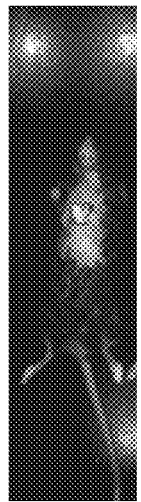 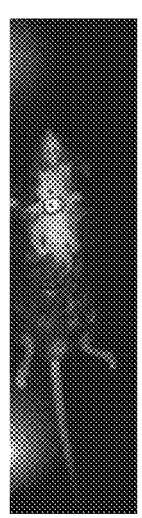 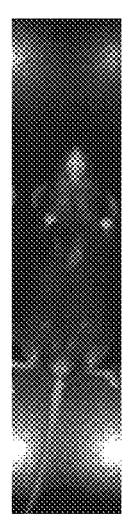
Fig. 19A    Fig. 19B    Fig. 19C

RECOMBINATION ACTIVATING GENE (RAG) INDUCED V(D)J GENE TARGETING

The project leading to this application has received funding from the European Research Council (ERC) under the European Union's Horizon 2020 research and innovation program grant agreement No 759296.

CROSS-REFERENCE TO AN ELECTRONICALLY SUBMITTED SEQUENCE LISTING

The instant application contains a Sequence Listing, which has been submitted in ASCII text file format via EFS-Web and is hereby incorporated by reference in its entirety. Said ASCII copy, created on Oct. 17, 2019, is named "4475.0030001_SL_ST25," and is 84,769 bytes in size.

FIELD OF THE INVENTION

The invention relates to immunotherapy. More specifically, the invention relates to methods and compositions for engineering T cells and B cells using V(D)J recombination, compositions, methods and uses thereof in immunotherapy.

BACKGROUND ART

References considered to be relevant as background to the presently disclosed subject matter are listed below:
[1] Beatty G L, Haas A R, Maus M V, et al. Mesothelin-specific chimeric antigen receptor mRNA-engineered T cells induce anti-tumor activity in solid malignancies. Cancer Immunol Res. 2014; 2(2): 112-120.
[2] Liu X, Ranganathan R, Jiang S, et al. A Chimeric Switch-Receptor Targeting PD1 Augments the Efficacy of Second-Generation CAR T Cells in Advanced Solid Tumors. Cancer Res. 2016; 76(6): 1578-1590.
[3] Sharpe M, Mount N. Genetically modified T cells in cancer therapy: opportunities and challenges. Dis Model Mech. 2015; 8(4):337-350.
[4] Poirot L, Philip B, Schiffer-Mannioui C, et al. Multiplex Genome-Edited T-cell Manufacturing Platform for "Off-the-Shelf" Adoptive T-cell Immunotherapies. Cancer Res. 2015; 75(18):3853-3864.
[5] Garfall A L, Maus M V, Hwang W T, et al. Chimeric Antigen Receptor T Cells against CD19 for Multiple Myeloma. N Engl J Med. 2015; 373(11):1040-1047.
[6] Maude S L, Frey N, Shaw P A, et al. Chimeric antigen receptor T cells for sustained remissions in leukemia. N Engl J Med. 2014; 371(16):1507-1517.
[7] Zhao Y, Parkhurst M R, Zheng Z, et al. Extrathymic generation of tumor-specific T cells from genetically engineered human hematopoietic stem cells via Notch signaling. Cancer Res. 2007; 67(6):2425-2429.
[8] Themeli M, Kloss C C, Ciriello G, et al. Generation of tumor-targeted human T lymphocytes from induced pluripotent stem cells for cancer therapy. Nat Biotechnol. 2013; 31(10):928-933.
[9] Hacein-Bey-Abina S, Garrigue A, Wang G P, et al. Insertional oncogenesis in 4 patients after retrovirus-mediated gene therapy of SCID-X1. J Clin Invest. 2008; 118(9):3132-3142.
[10] Bryant L M, Christopher D M, Giles A R, et al. Lessons learned from the clinical development and market authorization of Glybera. Hum Gene Ther Clin Dev. 2013; 24(2):55-64
[11] Barzel A, Paulk N K, Shi Y, et al. Promoterless gene targeting without nucleases ameliorates haemophilia B in mice. Nature. 2015; 517(7534):360-364.
[12] Sather B D, Romano Ibarra G S, Sommer K, et al. Efficient modification of CCR5 in primary human hematopoietic cells using a megaTAL nuclease and AAV donor template. Sci Transl Med. 2015; 7(307):307ra156.
[13] Boutros C, Tarhini A, Routier E, et al. Safety profiles of anti-CTLA-4 and anti-PD-1 antibodies alone and in combination. Nat Rev Clin Oncol. 2016; 13(8):473-486.
[14] Luo X M, Maarschalk E, O'Connell R M, Wang P, Yang L, Baltimore D. Engineering human hematopoietic stem/progenitor cells to produce a broadly neutralizing anti-HIV antibody
[15] Fusil F, Calattini S, Amirache F, et al. A Lentiviral Vector Allowing Physiologically Regulated Membrane-anchored and Secreted Antibody Expression Depending on B-cell Maturation Status. Mol Ther. 2015; 23(11): 1734-1747
[16] Moreau A, Vicente R, Dubreil L, et al. Efficient intrathymic gene transfer following in situ administration of a rAAV serotype 8 vector in mice and nonhuman primates. Mol Ther. 2009; 17(3):472-479.0
[17] Richter M, Saydaminova K, Yumul R, et al. In vivo transduction of primitive hematopoietic stem cells after mobilization and intravenous injection of integrating adenovirus vectors. Blood. 2016.
[18] Chen Z, Fischer E R, Kouiavskaia D, et al. Cross-neutralizing human anti-poliovirus antibodies bind the recognition site for cellular receptor. Proc Natl Acad Sci USA. 2013; 110(50):20242-20247.
[19] Schlereth B, Kleindienst P, Fichtner I, et al. Potent inhibition of local and disseminated tumor growth in immunocompetent mouse models by a bispecific antibody construct specific for Murine CD3. Cancer Immunol Immunother. 2006; 55(7): 785-796.

Acknowledgement of the above references herein is not to be inferred as meaning that these are in any way relevant to the patentability of the presently disclosed subject matter.

BACKGROUND OF THE INVENTION

Cancer immunotherapy harnesses and augments immune mechanisms to fight malignancies. In particular, adoptive T cell transfer entails the activation and expansion of T cells that target tumor associated antigens (TAA). Naturally occurring T cell receptors (TCRs) often have low affinity against TAAs. However, T cells can be engineered to express highly potent TCRs, which can recognize fragments of both intracellular and cell surface proteins when presented in a major histocompatibility complex (MHC) context. Alternatively, T cells can be engineered to express chimeric antigen receptors (CARs), which have a high TAA affinity. CARs recognize intact cell surface proteins in an MHC independent manner, and are thus insensitive to cancer escape mechanisms associated with MHC loss. Second and third generation CARs have an increased potency due to inclusion of multiple co-stimulatory domains, allowing highly promising clinical results for several hematological malignancies. Treatment of solid tumors may in turn be facilitated by identifying and targeting cancer specific antigens, by using short-lived CAR mRNA to reduce toxicity [1] and by counteracting inhibitory immune checkpoints [2]. However, large scale application of adoptive T cell therapy may be extremely challenging. State of the art T cell engineering for cancer immunotherapy relies on ex vivo manipulations. It is conducted in a limited number of specialized medical centers, because it requires dedicated facilities and expertise in clinical grade collection, purification and activation of T cell products, as well as in viral vector manipulations [3]. Furthermore, autologous T cell engineering and expansion is time-consuming, delaying treatment of patients in need. These challenges can be partially mitigated by the recent development of universal allogenic CAR T cells (UCART) which underwent nuclease-mediated knockout of the endogenous TCR to prevent graft vs. host disease (GVHD) as well as knockout of the CD52 gene, allowing expansion in the presence of the conditioning drug Alemtuzumab [4]. However, risk remains of GVHD from residual TCR coding T cells, and even "off-the-shelf" cell products may require complex cryopreservation and subsequent expansion.

Treatment outcome is determined by the subset composition of the targeted T cell population. Both CD4 and CD8 CAR modified T cells participate in an effective cancer immunotherapy. In particular, naïve and central memory effector T cells are most effective in inducing remission. However, in trials reported to date, the modified T cell population often included also terminally differentiated and exhausted T cells that contribute little to the treatment efficacy [5-6]. Therefore, methods have been developed for the introduction of CAR and engineered TCRs into pluripotent cells ((Hematopoietic stem cells (HSCs) and Induced Pluripotent Stem Cells (iPSCs)) which are later differentiated into T cells [7-8]. However, in pluripotent cells, the promiscuously integrating vectors used to date, including retroviral and lentiviral vectors as well as transposons, may induce clonal expansion and cancer by integrating near oncogenes leading to their aberrant expression [9]. In contrast, the Recombinant adeno-associated virus (rAAV) is a safe and potent vector that is widely used in gene therapy trials and approved drugs [10]. The AAV virus is non-pathogenic and the rAAV vector encodes no viral genes. rAAV is less prone to insertional mutagenesis, is not associated with adverse immunogenicity, can be produced in high titers, and requires no toxic pseudotyping for in vivo applications. Importantly, several rAAV serotypes can efficiently transduce HSCs and lymphocytes. However, rAAV is not commonly used for Immunotherapy because it rarely integrates to allow stable expression from dividing cells.

The inventors recently demonstrate that rAAV can be used to facilitate stable expression at therapeutic levels from a dividing tissue following site-specific gene integration into the genome [11]. In particular, rAAV was used to facilitate nuclease-independent insertion of a promoterless therapeutic transgene to be expressed only upon integration by homologous recombination (HR) into the liver-specific highly-expressed albumin locus. Using this method, sustained amelioration of genetic diseases such as haemophilia B38, Crigler Najjar syndrome, and methylmalonic academia, was demonstrated after a single systemic injection to either neonatal or adult mice. Other groups have attempted site specific integration of CAR genes into T cells [12]. Basal rates of HR in T cells and HSC are low, but can be increased by several orders of magnitude by the introduction of targeted DNA breaks using site-specific nucleases. However, these nucleases have off-target effects that are difficult to monitor. Even on target, a double strand break, induced by a nuclease, leads more often to mutagenic non-homologous end joining (NHEJ) than to the desired gene insertion by HR. The nucleases also include microbial protein domains that, if used in vivo, may be immunogenic, leading to elimination of targeted cells, or even worse, to an anaphylactic response. An optimal lymphocyte engineering technology should allow locus specific integration of the receptor and/or Antibody gene without relying on bacterial nucleases.

Monoclonal Antibodies are used widely to treat cancer, autoimmune diseases, and more. Mouse Antibodies, used in early day therapies, were often immunogenic and have been replaced with humanized Antibodies and fully human Antibodies produced using transgenic animals or phage display. In addition, different Antibody fragments and modified Antibodies are finding increasing utility, including single chain variable fragments (scFv), bi-specific and tri-specific Antibodies. Recent years have seen a great surge in the application of monoclonal Antibodies that block inhibitory immune checkpoints, and thus allow the immune system to better fight the malignancy. Examples include anti-PD1 and anti CTLA-4 Antibodies which have already transformed the management of patients with advanced-stage melanoma and may be highly efficient in the treatment of many other cancers [13]. Nevertheless, for most indications, monoclonal Antibody therapy is rarely curative. An Antibody has a limited half-life and has to be repeatedly administered at a very high financial cost and with aggravated risk for the development of anti-drug antibodies. B cells engineering may enable safely expression of desired antibodies and thus may represent a potent and sustained immunotherapy activated by an antigen and naturally augmented by affinity maturation. However, B cell engineering has received little attention due to concerns about sustained autoimmunity and challenges in activation and avoidance of tolerance. Luo et al. have engineered human hematopoietic stem/progenitor cells to produce an anti-HIV Antibody upon in vitro maturation to B cells [14]. However, expression levels were constitutively low as the lentivector-coded Antibody did not allow B cell activation. Fusil et al., used a different lentivector design that allowed B cell activation and differentiation into Antibody producing plasma cells [15]. However, the promiscuous and ectopic lentiviral integration as well as the synthetic polyadenylation sites that were used prevented native regulation on the transition from BCR expression to antibody secretion and did not allow for affinity maturation upon activation. In addition, lentiviral transduction is ill-fitted for in vivo applications, thus subjecting B cell engineering to similar challenges to those discussed above with regards to T cell engineering.

There is therefore a crucial unmet need to design scalable immunotherapies to treat the very large population of patients with cancer and autoimmune diseases.

The present invention address these issues by providing a revolutionary technology, named "VDJ targeting", for the engineering of B cells as well as T cells, both in vivo and ex vivo.

SUMMARY OF THE INVENTION

In a first aspect, the invention relates to a method for targeted insertion of at least one nucleic acid sequence of interest into a target genomic locus of a mammalian cell. More specifically, the method of the invention comprises the step of contacting a mammalian cell expressing the recombination activating gene (RAG) complex with at least one nucleic acid cassette comprising the nucleic acid sequence/s of interest and at least one recognition signal sequence (RSS), or with a vector comprising the cassette. It should be noted that the insertion of the nucleic acid sequence of interest into the target genomic locus is facilitated, mediated and performed by RAG-catalyzed recombination. More specifically, such recombination may occur in some embodiments between at least one genomic RSS flanking the target genomic locus and at least one RSS comprised within the nucleic acid cassette.

In a second aspect, the invention relates to a method for targeted insertion of at least one nucleic acid sequence of interest into a target genomic locus of a cell in a mammalian subject. More specifically, the method may comprise the step of administering to the subject an effective amount of at least one nucleic acid cassette comprising the nucleic acid sequence of interest and at least one RSS. The invention further encompasses in some embodiments thereof the administration of a vector comprising the cassette of the invention or any composition thereof to the subject. It should be noted that the nucleic acid cassette administered by the method of the invention enables the insertion of a nucleic acid sequence of interest into a target genomic locus.

A further aspect of the invention relates to a method of treating, preventing, ameliorating, inhibiting or delaying the onset of a pathologic disorder in a mammalian subject. More specifically, the method of the invention may comprise the step of administering to the treated subject an effective amount of at least one of: (a) nucleic acid cassette; (b) a vector, vehicle or composition comprising said nucleic acid cassette; and (c) a cell transduced or transfected with the nucleic acid cassette or with a vector comprising said cassette, or any combinations or compositions thereof. It should be noted that the cassette administered by the method of the invention may comprise at least one nucleic acid sequence of interest and at least one RSS. In yet some further embodiments, the cassette used by the method of the invention may lead to targeted insertion of at least one nucleic acid sequence of interest into a target genomic locus in at least one cell of the treated subject. The insertion of the nucleic acid sequence of interest into the target genomic locus in cell/s of the treated subject may be facilitated, mediated and/or performed by RAG-catalyzed recombination between at least one genomic RSS flanking the target genomic locus and at least one RSS comprised within the nucleic acid cassette.

In yet a further aspect, the invention relates to a nucleic acid cassette. More specifically, the cassette of the invention may comprise at least one nucleic acid sequence of interest and at least one RSS. It should be further noted that in some embodiments, the cassette provided by the invention may be suitable for targeted insertion of at least one nucleic acid sequence of interest into a target genomic locus in a mammalian cell. In more specific embodiments, the insertion of the nucleic acid sequence of interest into the target genomic locus may be facilitated, mediated and/or performed by RAG-catalyzed recombination between at least one genomic RSS flanking the target genomic locus and at least one RSS comprised within the nucleic acid cassette.

In yet a further aspect, the invention relates to a pharmaceutical composition comprising at least one nucleic acid cassette, or any vector or cell comprising said cassette. More specifically, the cassette of the composition of the invention may comprise the nucleic acid sequence of interest and at least one RSS. In yet some further embodiments, the cassette provided by the composition of the invention may be used for targeted insertion of at least one nucleic acid sequence of interest into a target genomic locus. In more specific embodiments, the compositions of the invention may comprise any of the nucleic acid cassettes of the invention. In some optional embodiments, the compositions of the invention may further comprise at least one of pharmaceutically acceptable carrier/s, diluent/s, excipient/s and additive/s.

Further aspects of the invention concern a therapeutically effective amount of the nucleic acid cassette in accordance with the invention and any compositions, vectors or vehicles thereof for use in a method for targeted insertion of at least one nucleic acid sequence of interest into a target genomic locus of a mammalian cell. In some embodiments, the cassettes for use in accordance with the invention may comprise at least one nucleic acid sequence of interest and at least one RSS. In more specific embodiments, the insertion of the nucleic acid sequence of interest into the target genomic locus is mediated by RAG-catalyzed recombination between at least one genomic RSS flanking the target genomic locus and at least one RSS comprised within said nucleic acid cassette. In yet some further aspects, the invention provides a therapeutically effective amount of the nucleic acid cassette in accordance with the invention and any compositions, vectors, vehicles or cells comprising said cassette, for use in a method for treating, preventing, ameliorating, inhibiting or delaying the onset of a pathologic disorder in a mammalian subject. In some embodiments, the cassettes for use in accordance with the invention may comprise at least one nucleic acid sequence of interest and at least one RSS. Thus, in some embodiments these cassettes lead to targeted insertion of at least one nucleic acid sequence of interest into a target genomic locus in the treated subject. In more specific embodiments, the insertion of the nucleic acid sequence of interest into the target genomic locus is mediated by RAG-catalyzed recombination between at least one genomic RSS flanking the target genomic locus and at least one RSS comprised within said nucleic acid cassette.

These and other aspects of the invention will become apparent by the hand of the following drawings.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Schematic representation of the construct incorporated into the double strand AAV vector.

Figure 2:
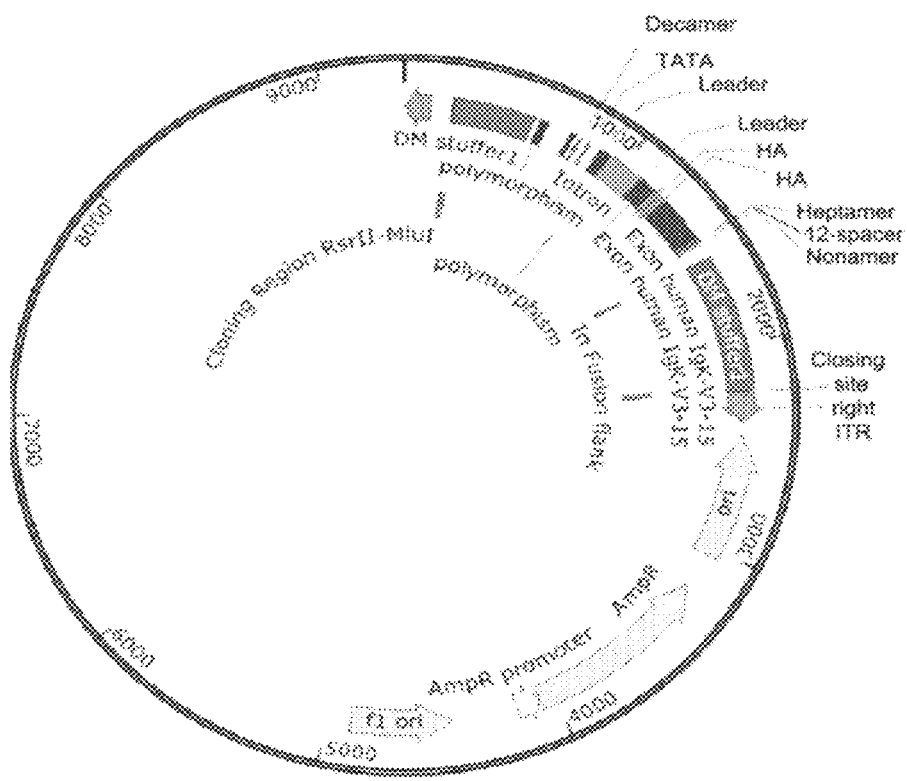

FIG. 2. dsAAV 360-A vector

Schematic map of the dsAAV 360-A vector. More specifically, the figure presents a map of a bacterial plasmid used in the preparation of the double stranded AAV vector (dsAAV) also referred to herein as self complementary AAV vector (ScAAV).

FIG. 3. VDJ targeting

Schematic representation of the location of the primers used for the Reverse transcription reactions analyzing the recombination products.

FIG. 4A-4B. V(D)J recombination and VDJ targeting

FIG. 4A shows natural V(D)J recombination during lymphocyte development. D to J recombination precedes V to DJ recombination FIG. 4B shows VDJ targeting: The rAAV vector encodes a receptor or Ab gene flanked by RSSs.

Transduction of lymphocyte precursors, which express RAG, facilitates insertion of the receptor/Ab gene between gene segments. The J recombination event may precede the V recombination event. The receptor/Ab gene is preceded by a sequence coding for a 2A peptide or an IRES to prevent protein fusions to preceding segments. A splice donor (SD)

may be provided to allow use of the endogenous C segments, upon integration and expression.

Figure 5A:
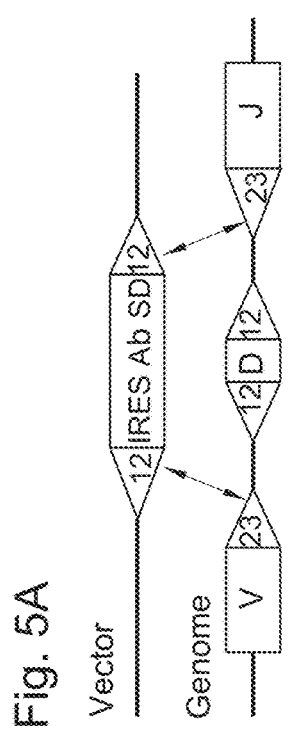
Figure 5B:
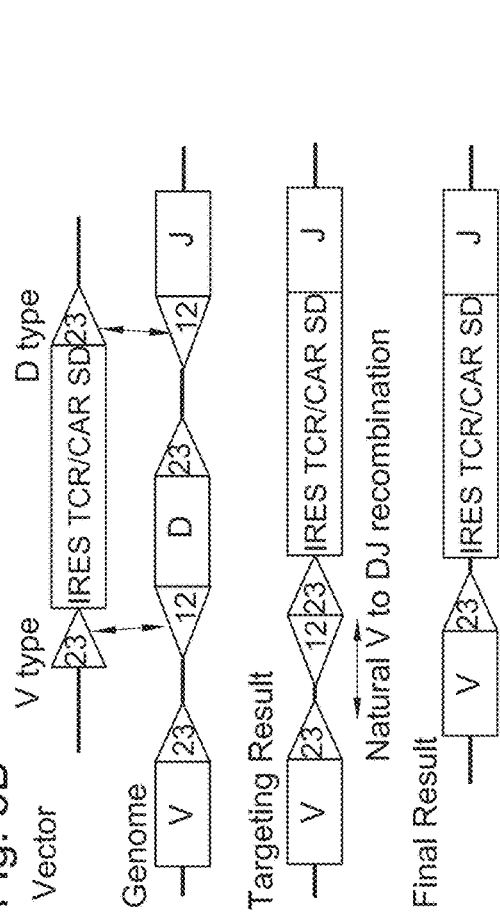

FIG. 5A-5B. RSS configurations

FIG. 5A shows specific RSS configurations and resulting VDJ targeting in the B lineage.

FIG. 5B shows specific RSS configurations and resulting VDJ targeting in the T lineage.

Triangles: RSSs, Rectangles: coding regions and transgene cassettes, Arrows: RAG recombination, SD (splice donor), Ab (antibody), CAR (chimeric antigen receptor), TCR (T cell receptor).

Figure 6A:
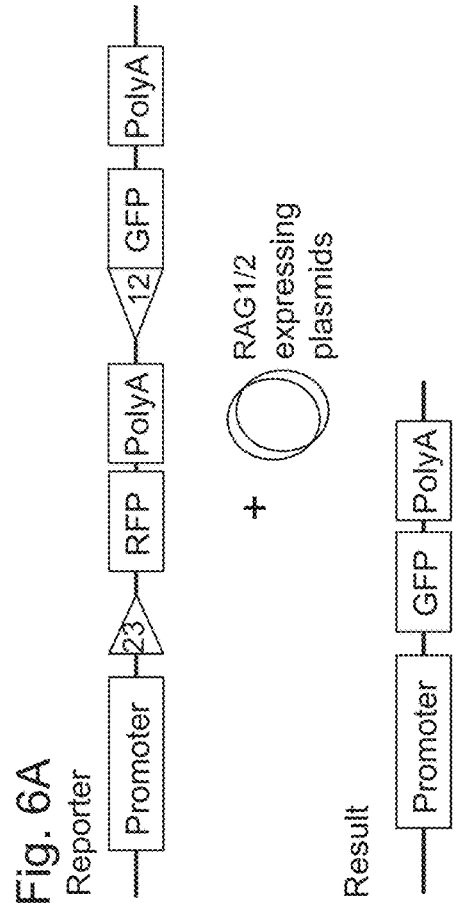
Figure 6B:
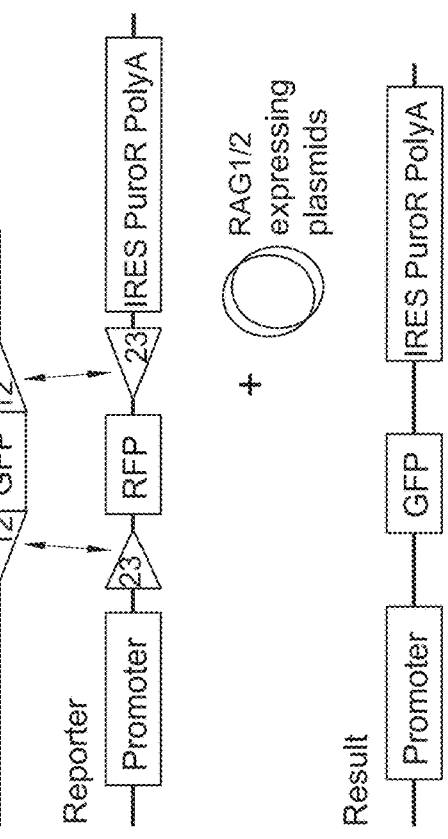

FIG. 6A-6B. Reporter systems

FIG. 6A illustrates an example of reporter system for RAG activity.

FIG. 6B. illustrates an example of reporter system for VDJ targeting in cell lines.

The reporter may be either episomal or integrated. Different donor and reporter constructs have different RSS sequences at different relative orientation in order to assess compatibility and optimize efficiency.

Figure 7A:
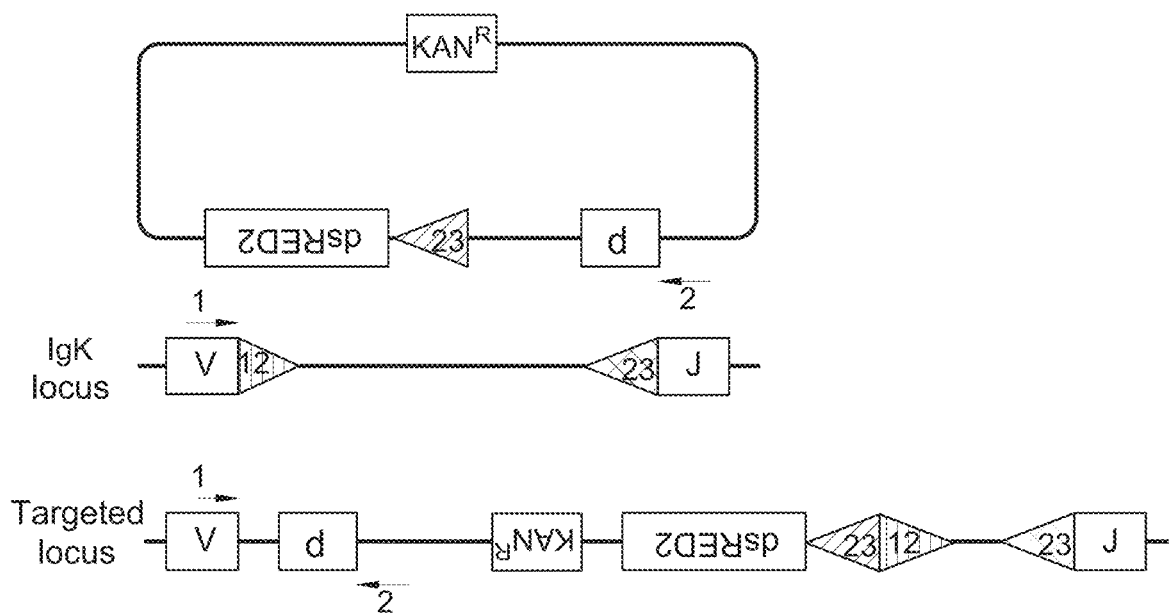
Figure 7B:
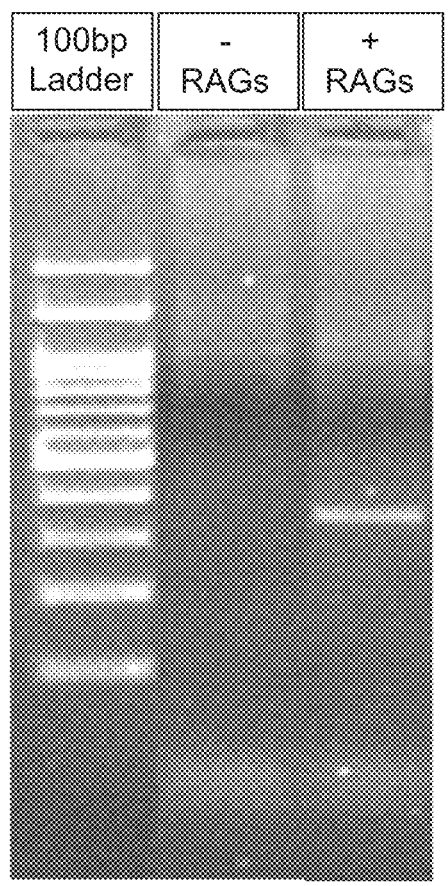

FIG. 7A-7B. VDJ targeting of a single-RSS construct to the IgK locus of HEK293T cells HEK293T cells were transfected with the dsRED2-Con23 plasmid containing a 23-consensus RSS and with plasmids encoding RAG1 and RAG2

FIG. 7A provides a Scheme of VDJ targeting between the IgK locus and the dsRED2-Con23 plasmid. Arrows with numbering 1 and 2 indicate the position of forward and reverse primers for subsequent PCR analysis.

FIG. 7B shows PCR product of recombination between the IgK locus and the dsRED2-Con23 plasmid, using primers forward/reverse designated by arrows 1 and 2 (on FIG. 7A).

Figure 8A:
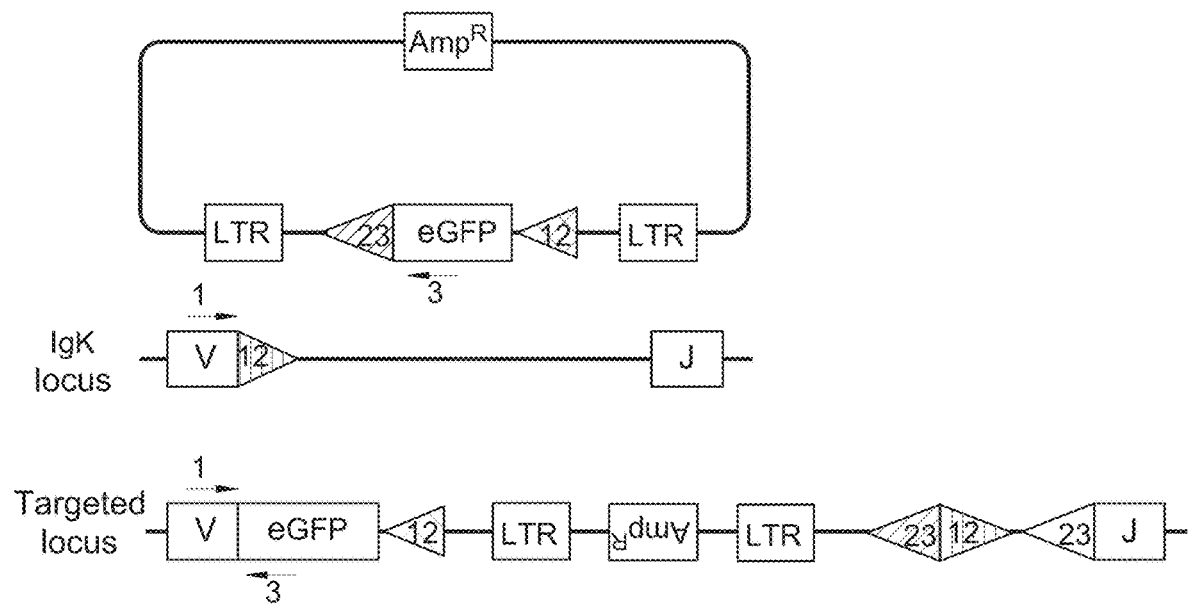
Figure 8B:
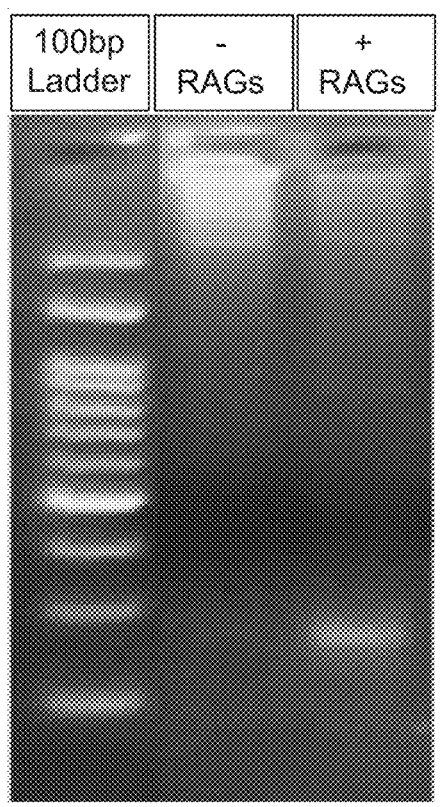

FIG. 8A-8B. VDJ targeting of a dual-RSS construct to the IgK locus of HEK293T cells HEK293T cells were transfected with the GFPi-redless plasmid containing a 23-consensus RSS and a 12-consensus RSS and with plasmids encoding RAG1 and RAG2.

FIG. 8A provides a scheme of VDJ targeting between the IgK locus and the GFPi plasmid. Arrows with numbering 1 and 3 indicate the position of forward and reverse primers for subsequent PCR analysis.

FIG. 8B shows PCR product of recombination between the IgK locus and the GFPi plasmid, using primers designated by arrows 1 and 3 (on FIG. 8A).

Figure 9A:
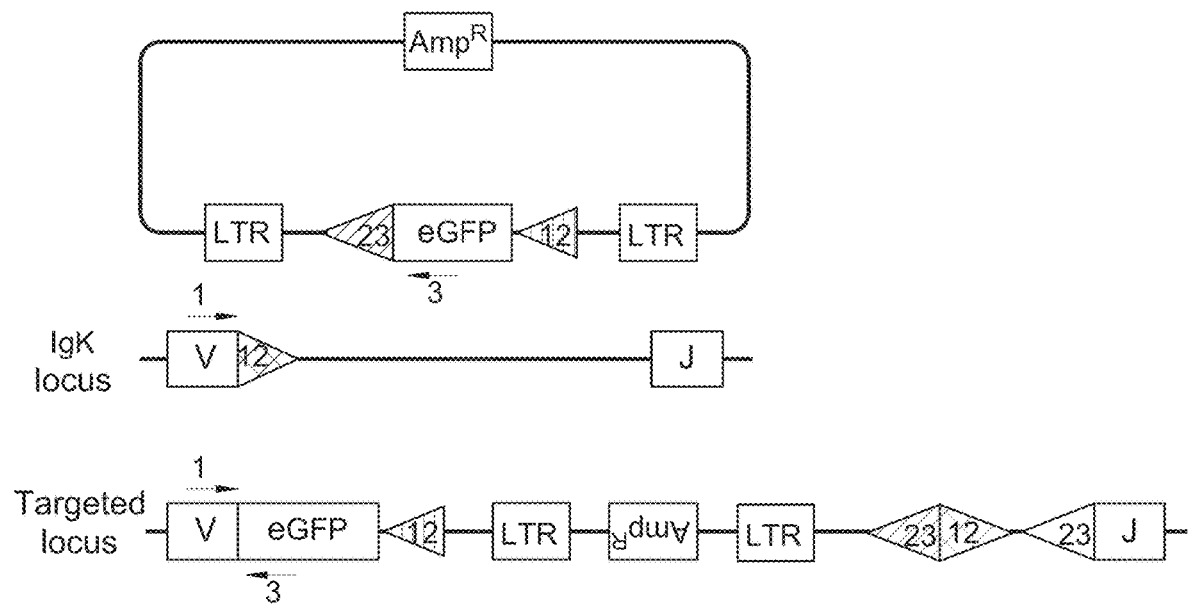
Figure 9B:
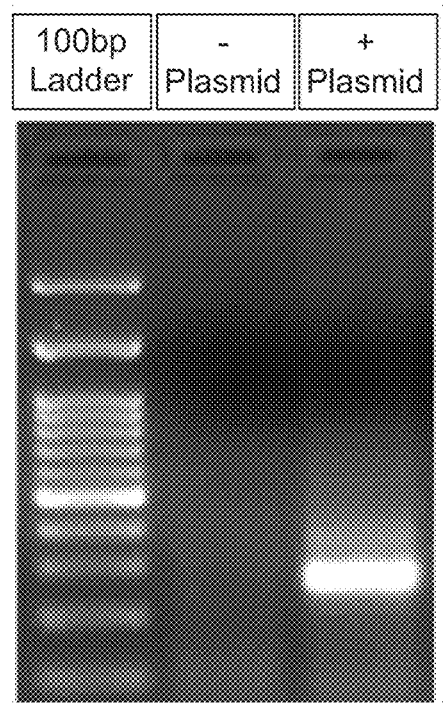

FIG. 9A-9B. VDJ targeting of a double-RSS construct to the IgK locus of inducibly differentiating B cells V-Abl immortalized murine Pro B cells were transfected with the GFPi-redless plasmid containing a 23-consensus RSS and a 12-consensus RSS and differentiation was induced using Imatinib.

FIG. 9A provides a scheme of VDJ targeting between the IgK locus and the GFPi-Redless plasmid. Arrows with numbering 1 and 3 indicate the position of forward and reverse primers for subsequent PCR analysis.

FIG. 9B shows PCR product of recombination between the IgK locus and GFPi-redless plasmid, using primers designated by arrows 1 and 3 (on FIG. 9A).

Figure 10:
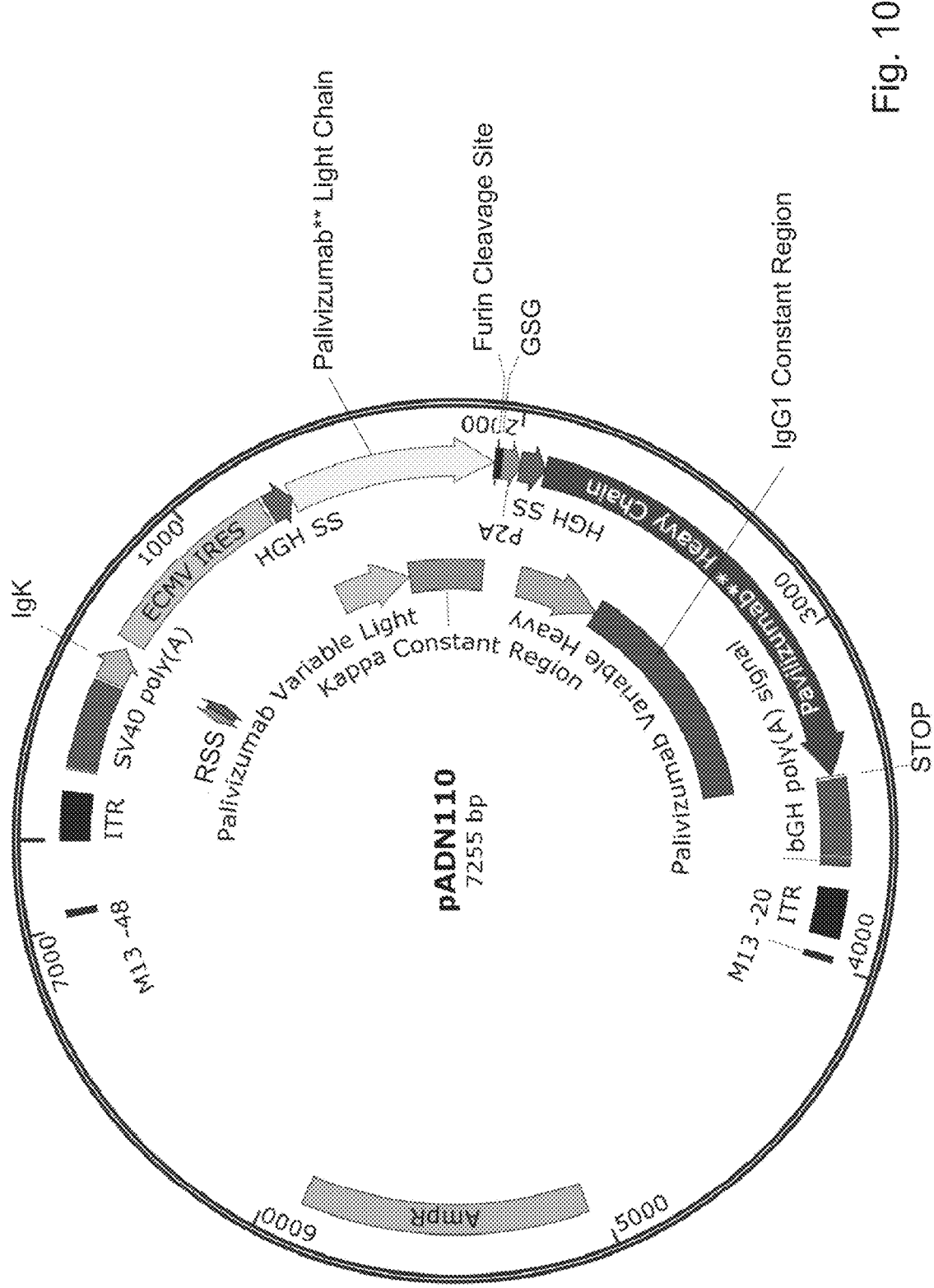

FIG. 10. pADN110 plasmid

Schematic map of the donor DNA i.e. the pADN110 plasmid comprising the nucleic acid sequence of interest (e.g., Palivizumab coding sequences).

Figure 11:
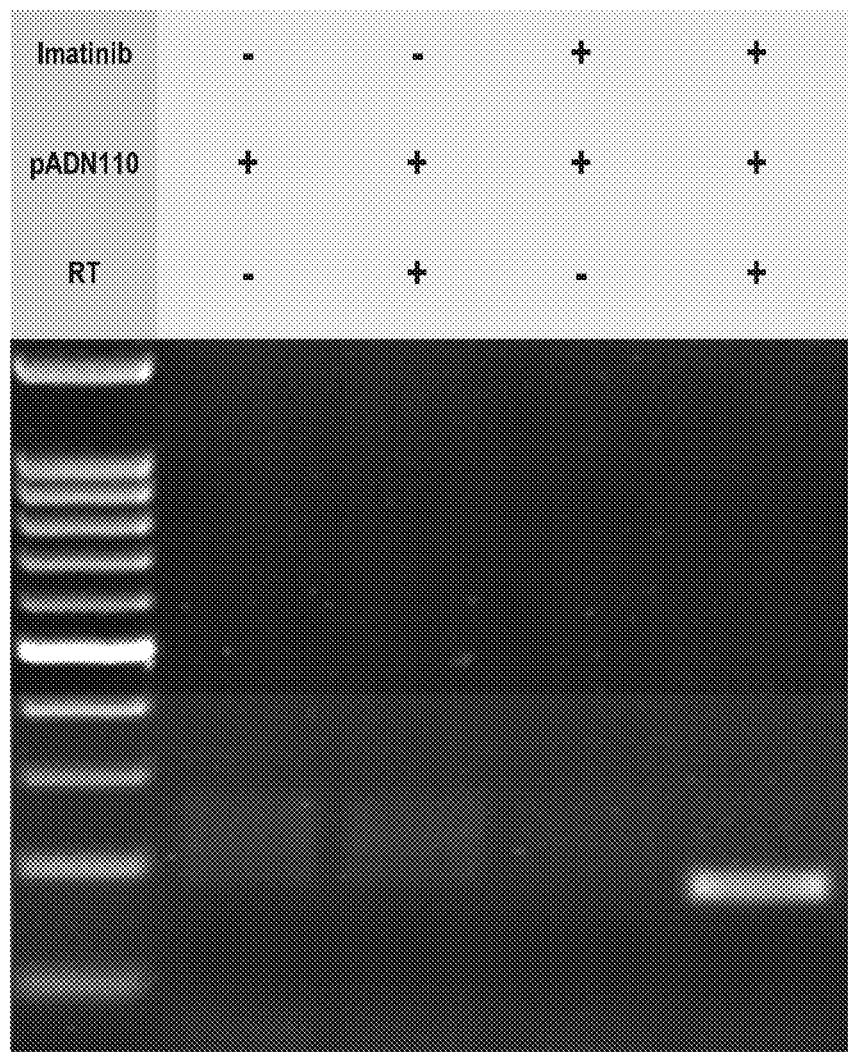

FIG. 11. VDJ targeting of antibody in inducibly differentiating B cells

DNA agarose gel of RT-PCR analysis confirming integration of the gene coding for the anti-RSV Palivizumab antibody into the IgK locus of B cell progenitors only in the presence of Imatinib.

Figure 12:
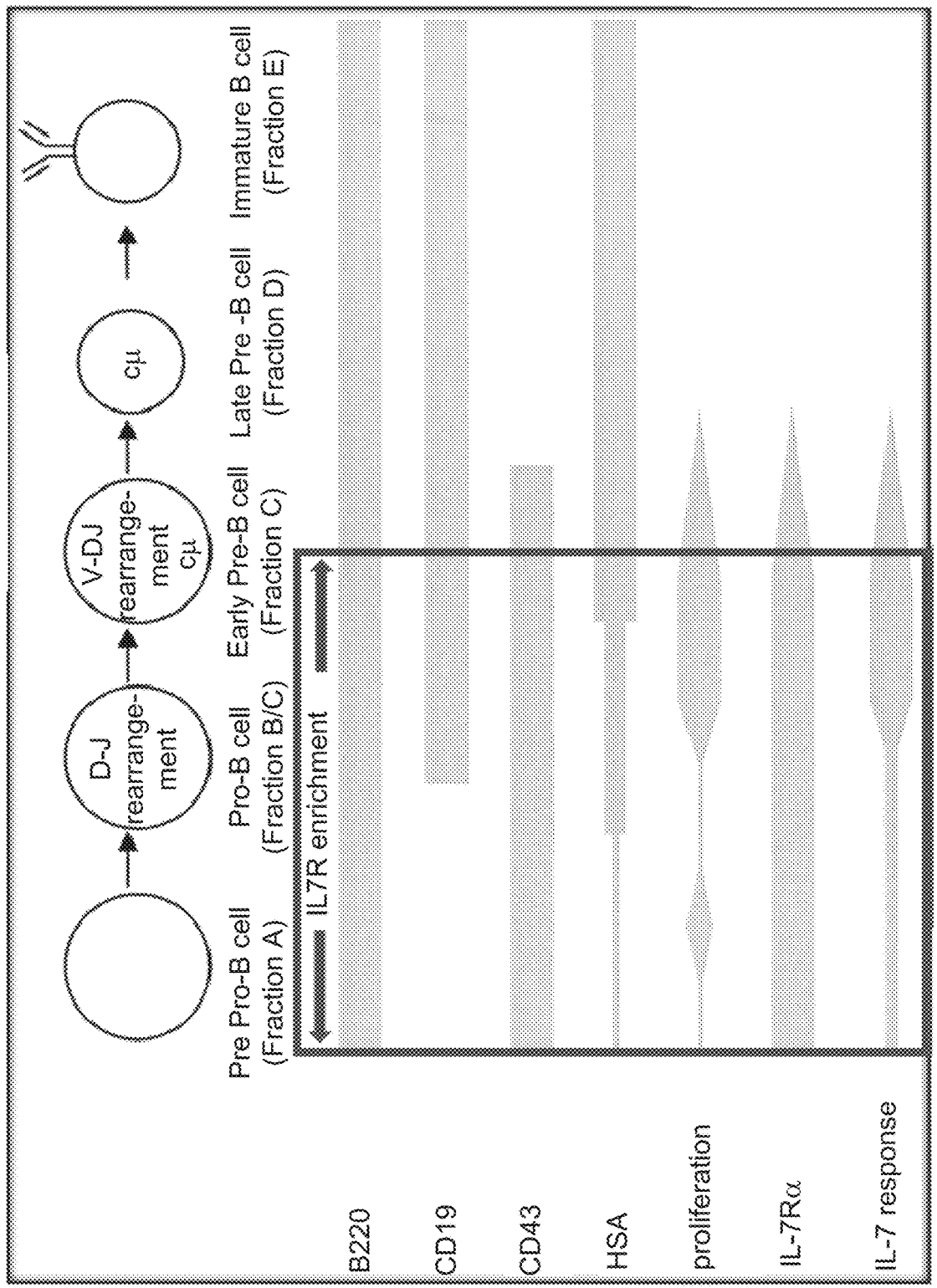

FIG. 12. VDJ recombination in B cell progenitors

Diagram representing B-cell lineage and the period of IL7-receptor enrichment.

Figure 13A:
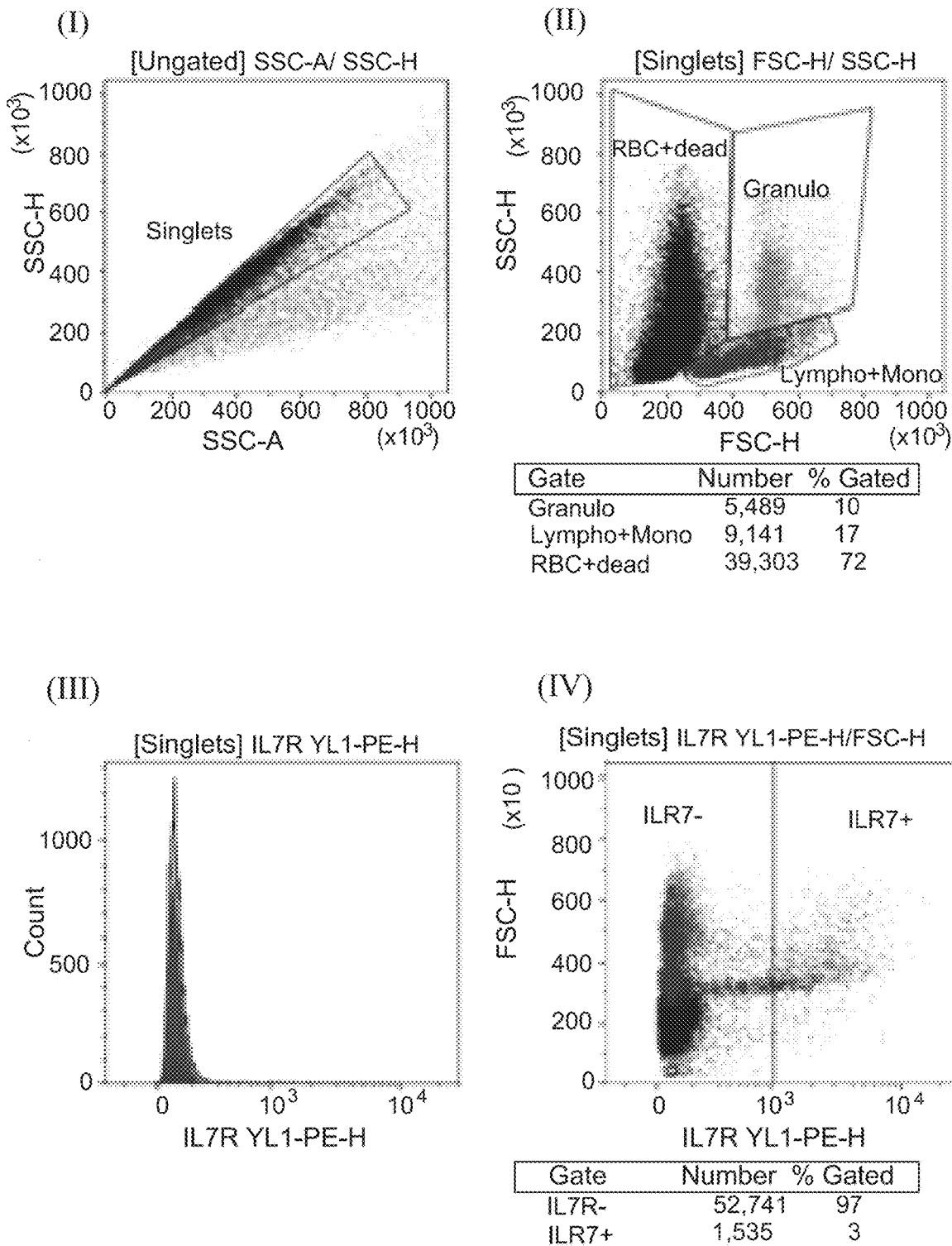
Figure 13B:
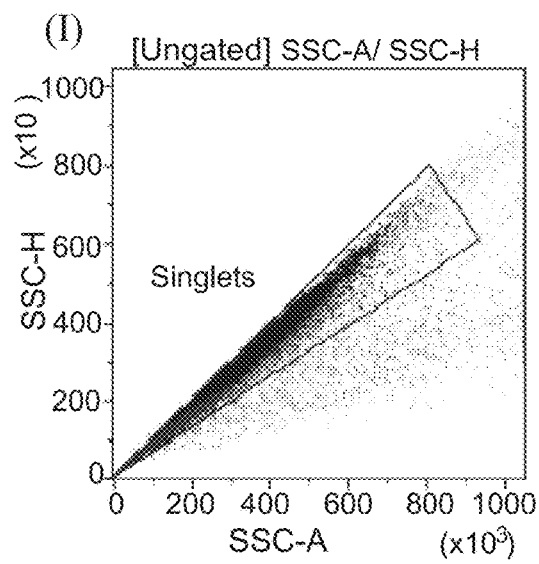
Figure 13B:
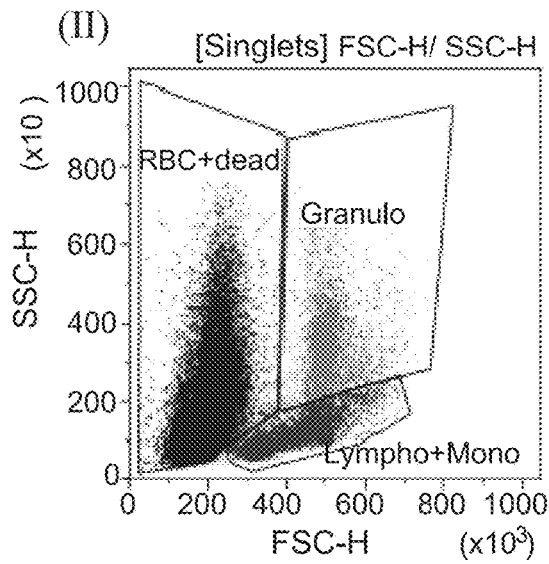
Figure 13B:
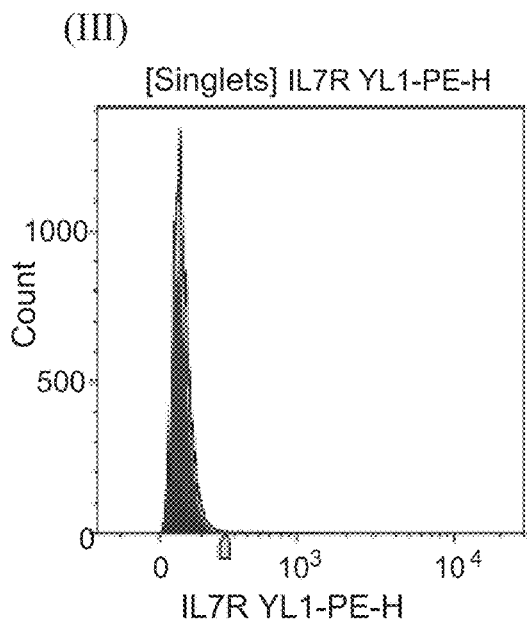
Figure 13B:
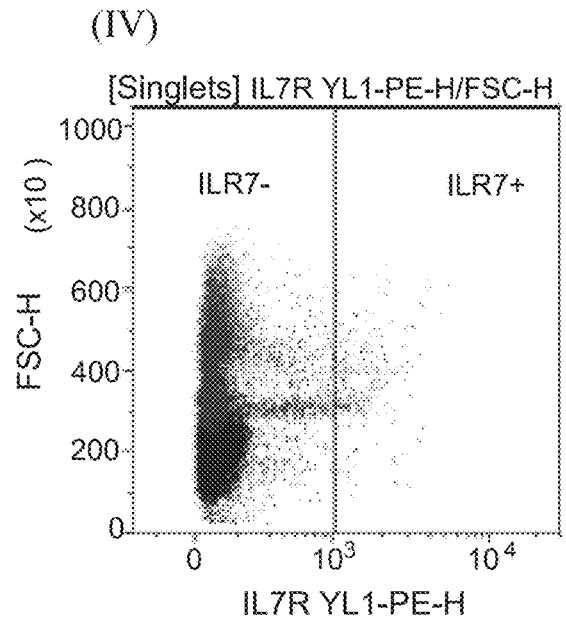
Figure 13C:
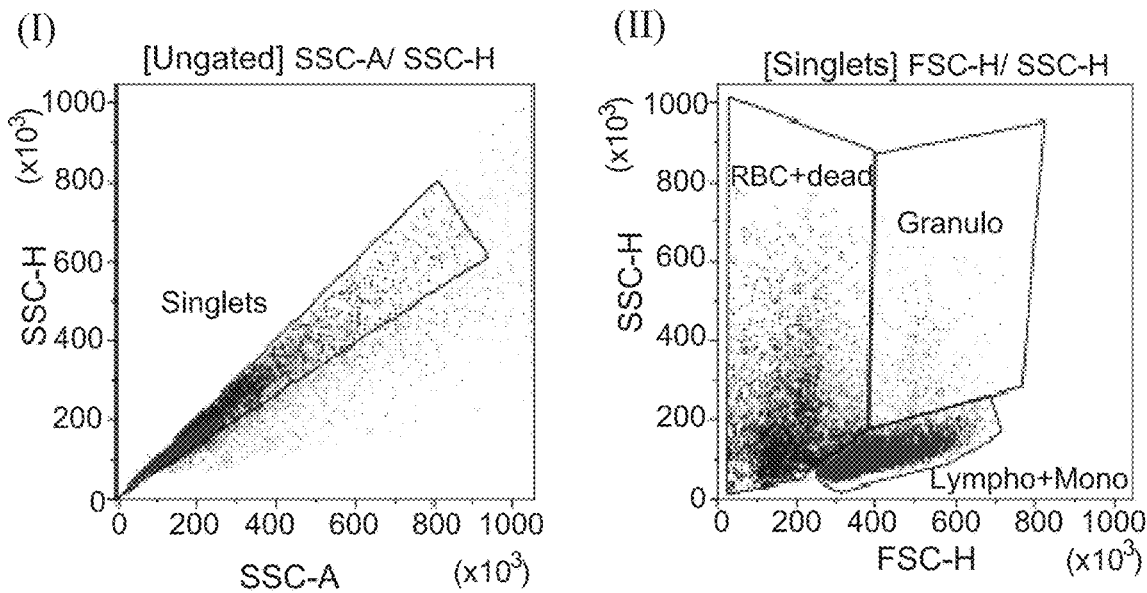
Figure 13C:
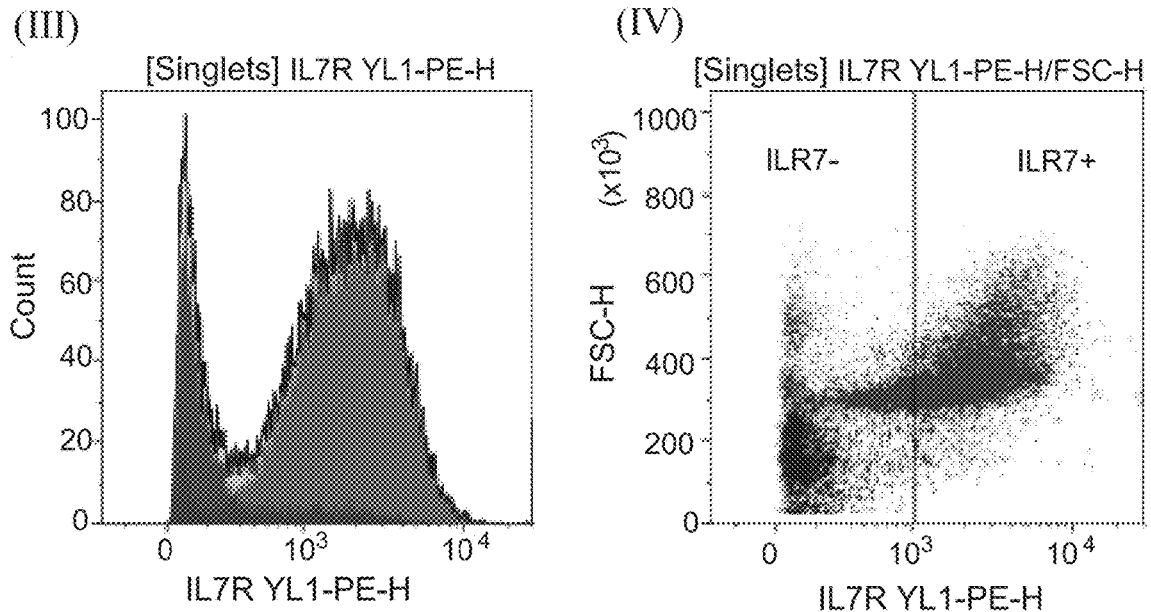

FIG. 13A-13C. IL7R enrichment

Flow cytometry profiles of murine bone marrow cells labeled with anti IL7R-PE and magnetic nano-beads, subjected to the enrichment protocol.

FIG. 13A (i-iv) are flow cytometry profiles of total loaded material.

FIG. 13B (i-iv) are flow cytometry profiles of column flow through.

FIG. 13C (i-iv) are flow cytometry profiles of column eluted IL7R-PE labeled cells.

Figure 14:
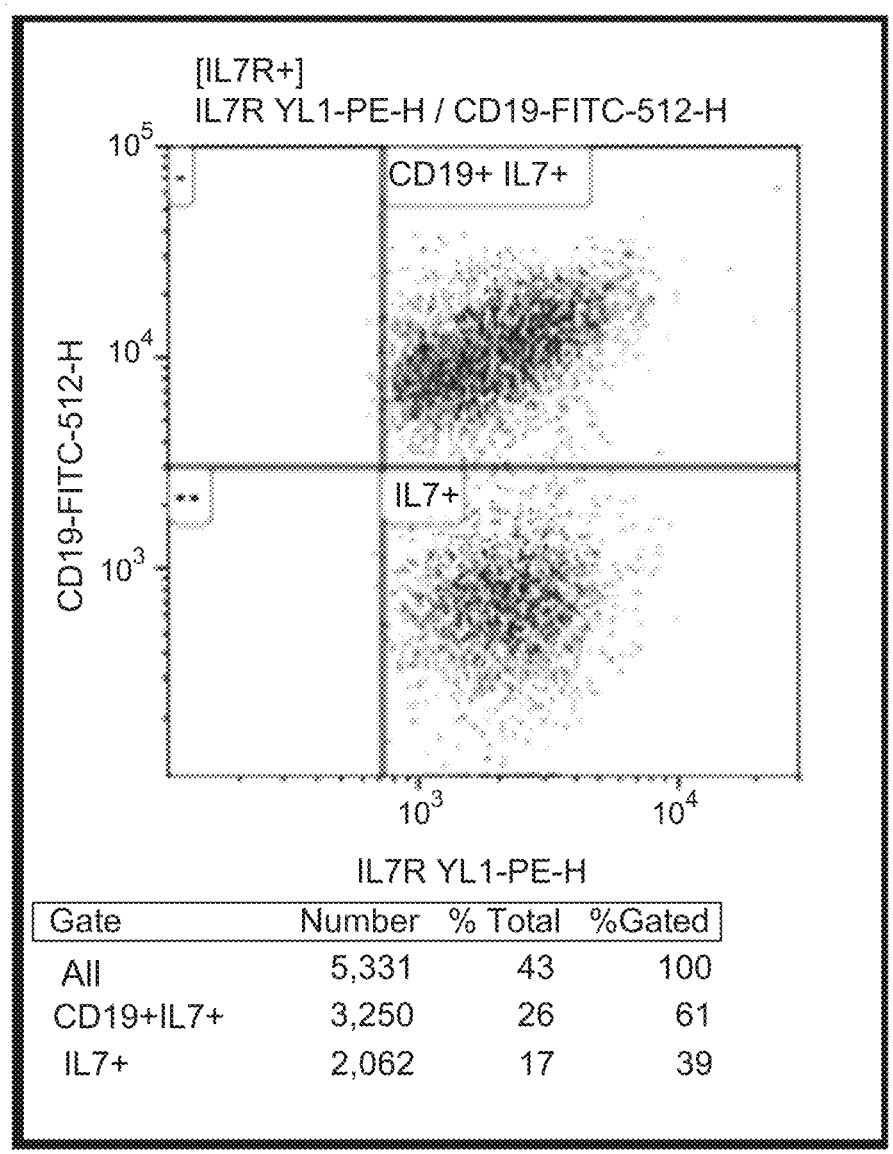

FIG. 14. CD19 staining of IL7R enriched cells

Bivariate plots of the IL7R positive gated cells. Cells at time point 0 after IL7R enrichment were washed and stained for CD19.

Figure 15A:
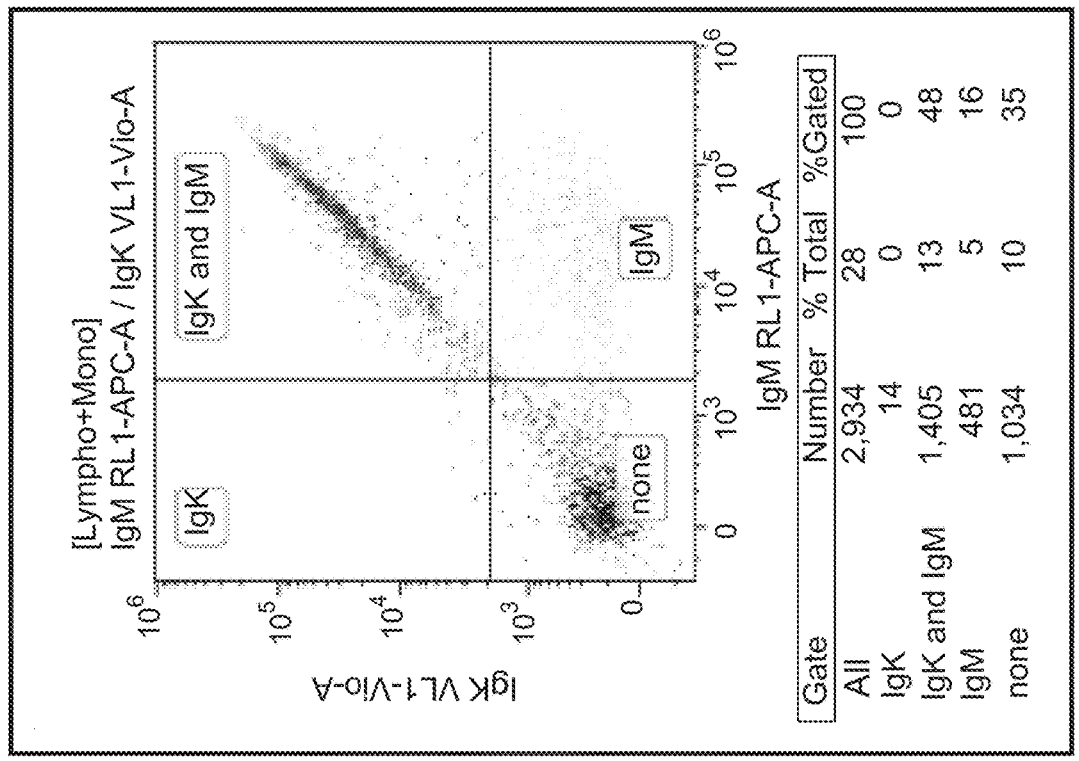
Figure 15B:
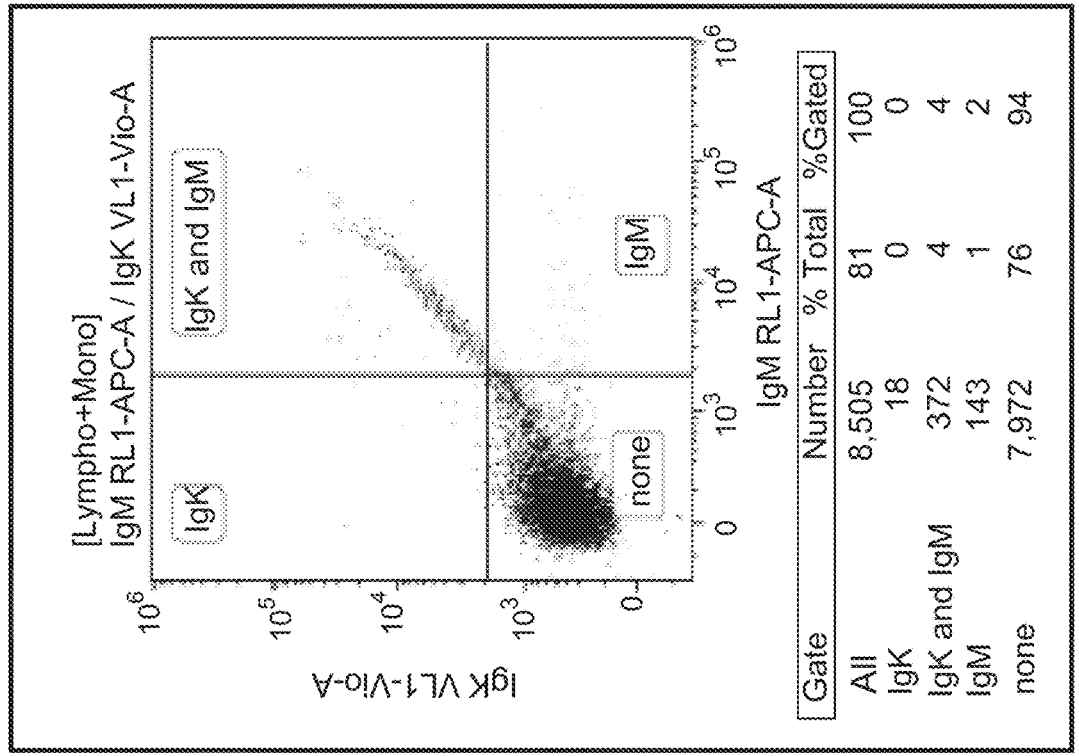

FIG. 15A-15B. Differentiation in IL7R enriched cells

Flow cytometry analysis showing differentiation of cultured IL7R positive cells.

FIG. 15A. Bivariate plots of cells at time point 0 (isolation) stained for IgK and IgM.

FIG. 15B. Bivariate plots of cells following 3 days of culture, stained for IgK and IgM.

Figure 16C:
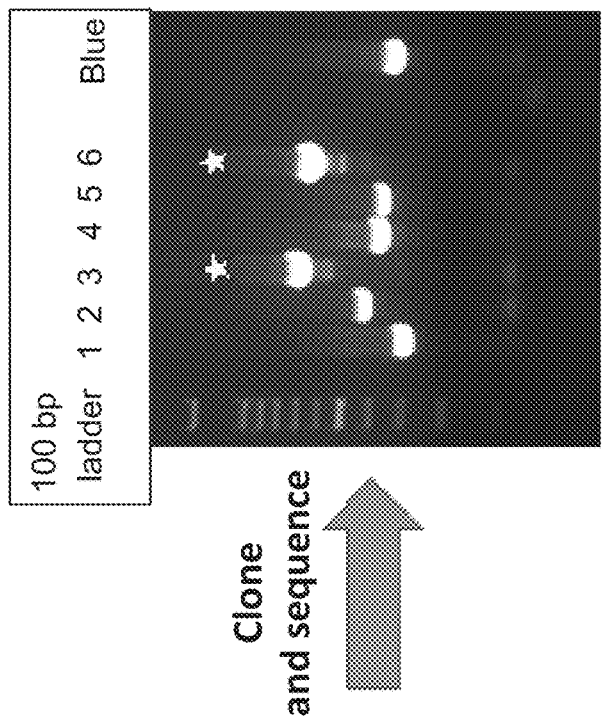
Figure 16B:
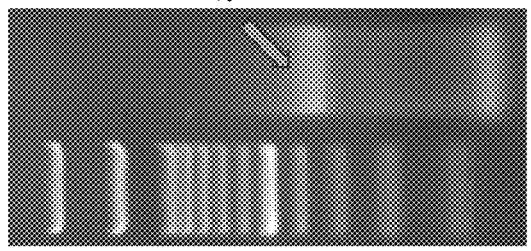
Figure 16A:
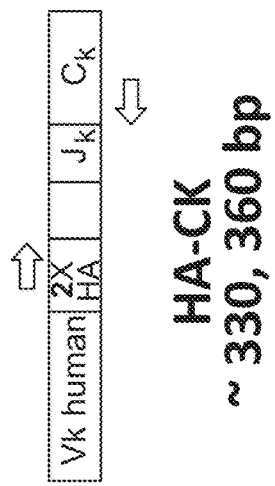

FIG. 16A-16C. RT analysis of IL7R+ enriched cells transduced with dsAAV 360-A

FIG. 16A. Schematic representations of the expected trans-recombination products. The black arrows indicate the position of the primers.

FIG. 16B. shows PCR product of the trans-recombination product using primers designated by arrows on FIG. 16A.

FIG. 16C. DNA agarose gels showing bands corresponding to the putative expected size of the trans-recombination product (marked by asterisk).

FIG. 17. Coding joint diversity

Figures 17A, 17B:
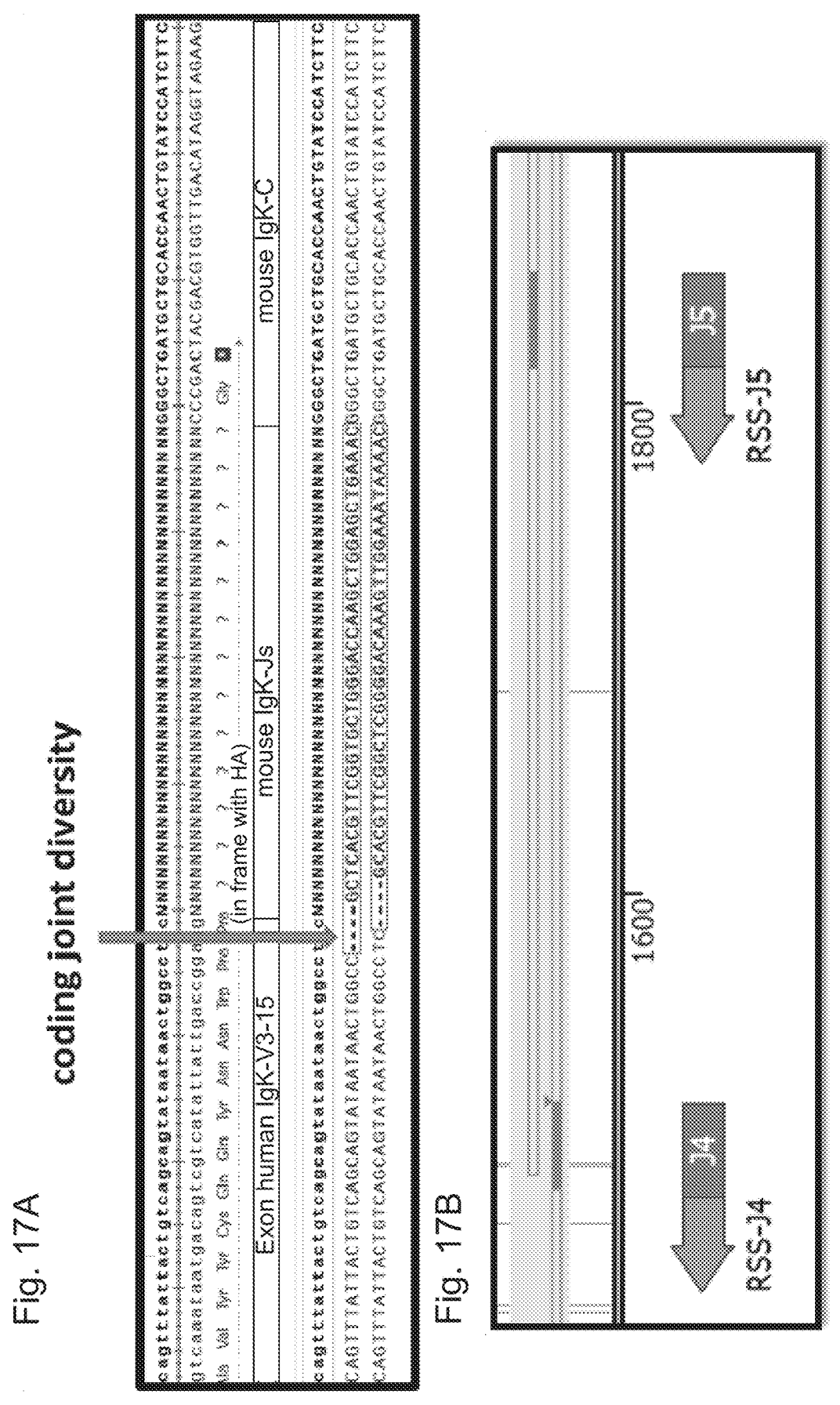

FIG. 17A. Schematic illustration of the coding joint junctional diversity—a unique attribute of RAG mediated integration, comprising the 5' to 3' fragment of the coding joints IgK-J4 and IgK-J5. More specifically, Line 1 of the figure shows IgK-V3-15 Sense strand, the Mouse IgK-J (any of J1, J2, J4, J5, that may be any sequence denoted herein as N for any nucleotide, in the middle block of line 1) and Mouse IgK-Constant Sense strand, as denoted by SEQ ID NO 42, Line 2 of the figure shows IgK-V3-15 anti-Sense strand, the Mouse IgK-J (any of J1, J2, J4, J5, that may be any sequence denoted herein as N for any nucleotide, in the middle block of line 1) and Mouse IgK-Constant Sense strand, as denoted by SEQ ID NO. 43. Line 3 of the figure shows putative encoded amino acid sequence of the IgK-V3-15, the Mouse IgK-J (any of J1, J2, J4, J5, that may be any sequence denoted herein as X for any amino acid residue, in the middle block of line 1) and Mouse IgK-Constant Sense strand, as denoted by SEQ ID NO. 44. Line 4 of the figure shows IgK-V3-15 Sense strand at the left block of the figure, as denoted by SEQ ID NO 45. The right block of line 4 of the figure shows Mouse IgK-Constant Sense strand. The same sequence is also shown at the left block of lines 5 and 6, as denoted by SEQ ID NO 46. Line 5 of the figure shows Left part of coding joint #1, as denoted by SEQ ID NO 47. The Middle part of line 5 of the figure shows Middle part of coding joint #1, as denoted by SEQ ID NO 48. Line 6 of the figure shows the Left part of coding joint #2, as denoted by SEQ ID NO. 49. The Middle part of line 6 shows Middle part of coding joint #2, as denoted by SEQ ID NO 50.

FIG. 17B. Schematic illustration of the 2 coding joints map to IgK-J4 and IgK-J5.

FIG. 18. Intrathymic injection

Fluorescent signals obtained from thymuses extracted postmortem from mice after live intrathymic injections of CFSE stained Jurkat cells.

FIG. 18A. is a photograph from a first mouse after extraction while FIG. 18B and FIG. 18C are photographs from a second mouse before and after extraction respectively.

FIG. 19. Intrathymic injection of Luciferase expressing cells

Live imaging photographs of mice after intrathymic injection of Luciferase expressing cells.

FIG. 19A is a photograph of a mouse injected with fresh bone marrow cells transduced with a luciferase expressing retroviral vector.

FIG. 19B is a photograph of a mouse injected with Lin-enriched bone marrow cells transduced with a luciferase expressing retroviral vector.

FIG. 19C is a photograph of a control, non-injected mouse.

Figure 20:
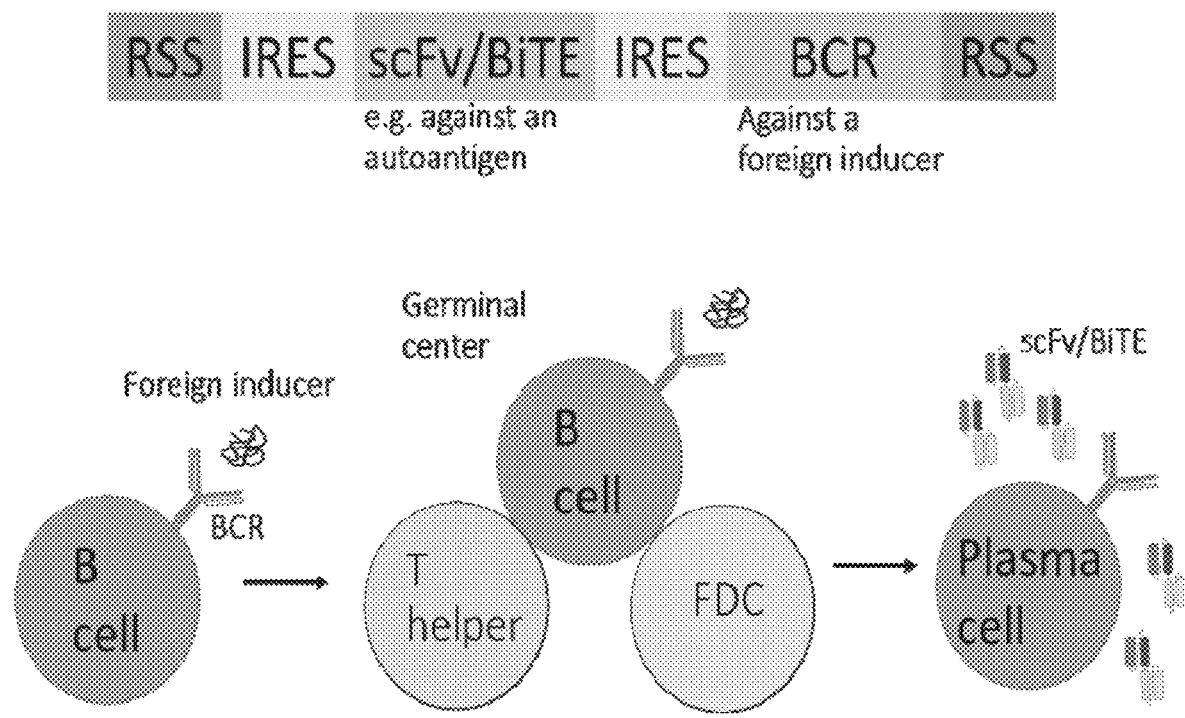

FIG. 20. Targeting B cells for inducible secretion of an autoantibody

Two independent cassettes are separately targeted: one coding for a secreted Antibody and one coding for a BCR targeting different antigens. Each gene is preceded by an IRES to allow separate translation. The secreted Antibody is preferably a scFv or a BiTE. The Antibody is directed against a disease associated autoantigen, and the BCR is directed against a foreign inducer. The B cell will differentiate to Antibody-secreting plasma cells only upon administration of the foreign inducer.

DETAILED DESCRIPTION OF THE INVENTION

T cell engineering for immunotherapy has shown clinical success, but large scale application is hindered by reliance on cumbersome ex vivo manipulations, performed in specialized centers only. In addition, B cell engineering has not shown therapeutic efficacy to date. Recombinant adeno associated vectors (rAAV) allow in vivo lymphocyte transduction but have seldom been used for lymphocyte engineering because they rarely integrate for stable expression in dividing cells. The present invention discloses herein a novel immunotherapy approach targeting immune genes into the genome using V(D)J recombination in developing lymphocytes. In some specific and non-limiting embodiments these immune-genes of interest may be delivered using any delivery vehicle, for example, a viral vehicle such as an adenoassociated virus (AAV), specifically, a recombinant AAV, (rAAV). The invention provides methods and compositions for ex vivo targeting of differentiating lymphocytes, demonstrating the feasibility and applicability thereof in the treatment and prophylaxis of pathologic disorders, specifically immune-related disorders such as cancer, autoimmune disease, pathogenic infections and immunodeficiencies (e.g., primary as well as secondary). Specifically, the methods, compositions and cassettes of the invention allow specific targeting of T cell receptors (TCRs) or chimeric antigen receptors (CARs) genes into loci coding TCR chains and specific targeting of antibody and B cell receptor genes into loci coding Immunoglobulin chains. The targeted antibodies or receptors are expressed under the endogenous regulation, only from the right cells at the right time and only at the correct amount.

More specifically, VDJ targeting in accordance with the invention, relies on the ability of the RAG complex to act in trans, i.e. to recombine RSSs found on different molecules. Indeed, by its evolution, structure and mechanism of action, RAG is a DNA transposase inducing the transposition of DNA segments in trans both in vitro and in vivo. While the efficient trans activity of RAG clearly speaks for the feasibility of VDJ targeting it is important to note that VDJ targeting is not a transposition event. In VDJ targeting cassettes provided by the invention, the relative orientation of the two RSSs precludes transposition but instead integration requires recombination of each vector RSS with an appropriate genomic RSS, thereby providing a targeted accurate insertion of the nucleic acid sequence of interest into the desired locus. Importantly, RAG has been shown to readily act in trans not only for transposition but also when the two RSSs are on different molecules. Unlike transposition, VDJ targeting is highly specific and as a second safety measure, the inventors refrain from overexpressing RAG, but rather rely on its endogenous expression only. In some embodiments, VDJ targeting as provided by the invention, may further rely on any delivery vehicle, specifically, a viral vector and more specifically, rAAV transduction. rAAV is proficient in transducing many different tissues in vivo, several rAAV variants can efficiently transduce HSCs and lymphocytes. In particular, rAAV is efficient, and superior to lentivectors, at in vivo intrathymic transfection in both mice and macaques.

VDJ targeting as provided by the methods, cassettes, compositions and uses described by the present invention, offers many advantages over state of the art technologies in safety, efficacy and scalability.

More specifically, state of the art T cell engineering is performed ex vivo using retrovectors, lentivectors or transposons, which are promiscuously integrating and bearing the risk of insertional mutagenesis and oncogene activation, particularly when applied to HSCs. In vivo use is not only genotoxic but may also requires toxic pseudotyping. In contrast, rAAV vectors are less genotoxic and are used in vivo without pseudotyping in multiple clinical trial trials and a EU approved drug. AAV is Non-pathogenic, and moreover, rAAV has no viral genes or promoters. Integration of a nucleic acid sequence of interest, is locus-directed and expression is from desired cell type only, while the promoterless vector diminishes risk of oncogene activation even upon rare off-target integration. State of the art nucleases can mediate receptor/antibody (Ab) targeting but they bear genotoxicity risk from both on and off-target mutations, as well as an immunogenicity risk if applied in vivo. In contrast, VDJ targeting in accordance with the invention, is independent of exogenous nucleases. VDJ targeting does not contribute to RAG associated genomic instability because RAG is not over-expressed, but instead targeting relies on natural RAG expression only, and the RSS orientation on the vector precludes transposition into the genome. Lymphocytes, engineered by state of the art technologies, may cross-react with autoantigens leading to adverse immune response. In contrast, in VDJ targeting in accordance with the invention, developing lymphocytes are targeted which are subjected to negative selection, thus diminishing the risk of undesired reactivity. With state of the art technologies, the chains of a targeted receptor may dimerize with those of the endogenous receptor leading to potentially dangerous undesired reactivity. In contrast, VDJ targeting at the endogenous locus as provided by the present invention, induces allelic exclusion and ensures expression of the desired receptor only.

Still further, state of the art vectors used in immunotherapy, including retrovectors, lentivectors and transposons do not allow high rates of in vivo transduction. In contrast, rAAV as used in some specific and non-limiting embodiments by the methods and compositions of the invention, is proficient in transducing many different tissues in vivo, and several rAAV variants can efficiently transduce HSCs and lymphocytes. In particular, rAAV8 is superior to lentivectors at in vivo intrathymic transfection in mice and in macaques. With state of the art technologies multiple lymphocyte subtypes are transduced, including exhausted cells. In contrast, in VDJ targeting as provided by the invention, only developing lymphocytes are engineered, leading to expression of the receptor/Ab gene in potent naïve cells. With state of the art technologies the targeted receptor may compete with the endogenous receptor and heterodimers on membrane presentation and cell activation. In contrast, VDJ targeting in accordance with the invention, induces allelic exclusion so that only the targeted receptor/Ab is expressed. Most importantly, state of the art technology does not allow B cell engineering for well controlled antibody secretion. In contrast, with VDJ targeting as disclosed by the invention, an Antibody gene can be inserted at an endogenous Antibody chain locus of a B cell in order to express a BCR and, upon antigen-induced activation, express a secreted antibody subjected to affinity maturation, including somatic hypermutation and class switching, for a potent immune response with reduced risk for antigenic escape and with memory retention.

Moreover, state of the art immunotherapy relies on cumbersome, expensive and time consuming ex vivo manipulations that can be performed in specialized centers only. In contrast, the VDJ targeting methods and compositions of the invention provide potent immunotherapeutic tool that may be applied safely to a much larger population of patients with diverse indications, in community clinics rather than specialized centers, at a lower cost and at a shorter time frame than possible with state of the art technologies.

VDJ targeting as provided by the present invention revolutionizes immunotherapy as it allows safe, efficient and scalable engineering of B cells and T cells, both in vivo and ex vivo. In addition, VDJ targeting has many important applications in basic science, biotechnology and medicine outside of immunotherapy alone.

In basic immunology studies, the technology can be used to target different reporters and allow studying the control over the expression of the endogenous locus. In addition, VDJ targeting can be used to study mechanistic aspects of the natural V(D)J recombination process, including parameters relating to the RSS sequences, RAG activity and differential gene segment availability. VDJ targeting could be used to target a barcoded library of receptors/Abs and follow cell population dynamics during development and subsequent to activation. Targeting of barcoded libraries can further be used in screens searching for optimal targeting of specific antigens. The output receptor/Ab of the screen could later be used in cell engineering for immunotherapy or in monoclonal Ab therapy. Finally, non-immune genes may be integrated into lymphocytes by VDJ targeting, and the product subsequently secreted, as a safe approach to augment the plasma levels of a desired protein.

Thus, in a first aspect, the invention relates to a method for targeted insertion of at least one nucleic acid sequence of interest into a target genomic locus of a mammalian cell.

More specifically, the method of the invention may comprise the step of contacting a mammalian cell expressing the recombination activating gene (RAG) complex with at least one nucleic acid cassette comprising the nucleic acid sequence/s of interest and at least one recognition signal sequence (RSS), or with a vector comprising the cassette. It should be noted that the insertion of the nucleic acid sequence of interest into the target genomic locus is facilitated, mediated and/or performed by RAG-catalyzed recombination between at least one genomic RSS flanking the target genomic locus and at least one RSS comprised within the nucleic acid cassette.

The present invention therefore provides safe, specific and efficient methods for V(D)J targeted insertion of a nucleic acid sequence of interest into a target genomic locus. This specific insertion is based on RAG complex expressed in the target cells, that catalyze the specific recombination. By "recombination" it is meant a process of exchange of genetic information between two polynucleotides. RAG catalyzed recombination as used herein, refers to recombination process performed by the RAG complex, for example, during V(D)J recombination. More specifically, the V(D)J recombination process cleaves and splices variable (V), diversity (D), and joining (J) non-contiguous immunoglobulin (Ig) segments in the genome. Ig heavy chains and T cell receptor (TCR) β chains are formed by sequential steps of D-J and V-DJ recombination, while Ig light chains and TCR a chains are generated by direct VJ recombination. The critical cleavage step in V(D)J recombination is executed by the lymphocyte-specific enzyme containing the multi-domain proteins recombination-activating gene 1 and 2 (RAG1 and RAG2). These two recombination-activating gene products, whose cellular expression is restricted to lymphocytes during their developmental stages, are essential to the generation of mature B and T lymphocytes.

RAG recognizes specific recombination signal sequences (RSSs) flanking the 3' end of the V, D, and J segments. RSSs are in some embodiments, genetic elements composed of a conserved heptamer (consensus: 5'CACAGTG-3'), a poorly conserved spacer of either 12±1 or 23±1 bp, and a conserved nonamer (consensus: 5'-ACAAAAACC-3') as revealed by sequence alignments of RSSs. These RSSs are designated as 12-RSS or 23-RSS after the length of the spacer. Thus, in some specific embodiments RSS applicable in the present invention may comprise a nucleic acid sequence that includes the heptamer, followed by a 12 nucleotide spacer (N may be any nucleotide), and the conserved nonamer, specifically, 5'-CACAGTG NNNNNNNNNNNN ACAAAAACC, as denoted by SEQ ID NO. 36. In yet another option, the RSS applicable in the present invention may comprise a nucleic acid sequence that includes the heptamer, followed by a 23 nucleotide spacer (N may be any nucleotide), and the conserved nonamer, specifically, 5'-CACAGTG NNNNNNNNNNNNNNNNNNNNNNN ACAAAAACC, as denoted by SEQ ID NO. 37. In yet another option, the RSS applicable in the present invention may comprise a nucleic acid sequence that includes the heptamer, followed by a 22 nucleotide spacer, and the conserved nonamer, specifically, 5'-s, as denoted by SEQ ID NO. 38. Still further, in some embodiments, the spacer may range between 12±1 or 23±1 bp, and therefore, RSSs applicable in the present invention may comprise in some embodiments spacer of 11 nucleotides, a spacer of 13 nucleotides and a spacer of 24 nucleotides, as denoted by SEQ ID NO. 39, 40 and 41, respectively. Recombination can only occur between one gene coding segment flanked by a 12-RSS and another segment flanked by a 23-RSS, establishing the 12/23 rule. Because V, D, and J segments are flanked by different RSSs, the 12/23 rule helps to ensure recombination between V, D, and J, but not within homotypic gene segments. Despite the enormous specificity that RSSs confer on the recombination process, the recombination signals themselves demonstrate a remarkable degree of sequence heterogeneity. Only the first three nucleotides of the heptamer and the fifth and sixth positions of the nonamer show almost perfect conservation and are therefore thought to be the major determinants of RSS specificity and function.

The nucleic acid sequence of interest is flanked by at least one RSS. The term "flanked" as used herein refers to a nucleic acid sequence positioned between two defined regions. For example, as indicated above, the nucleic acid sequence of interest is flanked by a first and optionally, a second RSS nucleic acid sequences, where in some embodiments, the first RSS nucleic acid sequence is positioned 5' (or upstream) to the nucleic acid sequence of interest and the optional second RSS nucleic acid sequence is positioned 3' (or downstream) to the nucleic acid sequence of interest, and vis versa.

As referred to herein as RAG catalyzed recombination is meant that the RAG complex catalyzes two consecutive reactions, nicking (strand cleavage) and hairpin formation (strand transfer), without dissociation. First, it binds either a 12-RSS substrate or a 23-RSS substrate and introduces a nick precisely at the junction between the coding segment and the RSS. Interactions with both the conserved heptamer and nonamer are required for optimal RAG activity because considerable sequence variation in endogenous RSSs substantially affects RAG binding affinity and recombination frequency. When a 12-RSS and a 23-RSS are bound to the same RAG, a synaptic, paired complex (PC) is formed. Next, upon PC formation, the free 3'-hydroxyl released from the nicking step attacks the opposing strand to create a hairpin coding segment and a blunt signal end, generating the cleaved signal complex (CSC). Dissociation of gene segment hairpins results in a signal end complex (SEC). Proteins in the classical nonhomologous end joining (NHEJ) DNA repair pathway are recruited to the RAG complex to process and join the coding segments. High-mobility group (HMG) proteins such as HMGB1 have been shown to stimulate RAG's activity in DNA binding, nicking, and hairpin formation, presumably by inducing RSS bending.

Thus, it should be understood that in some embodiments, the mammalian target cells in addition to RAG proteins, may further express any additional protein or component that participates in the V(D)J targeted insertion provided by the methods of the invention. More specifically, in some embodiments the mammalian target cells may express in addition to RAG proteins any other protein that participate in any of the stages of the V(D)J targeted insertion described herein, to name but a few, the high-mobility group protein 1 (HMGB1) proteins, DNA dependent protein kinase (DNA-PK), the Ku dimeric protein complex, Arthemis proteins and any further relevant proteins. Still further, RAG complex as referred to herein relates in some embodiments, to RAG-1 and RAG-2 proteins. RAG-1 contains about 1000 and RAG-2 contains about 500 amino acid residues. The enzymatic activity of the RAG proteins is concentrated largely in a core region that retains most of the DNA cleavage activity. The RAG-1 core contains the DDE motif that forms the major active site for DNA cleavage. These residues are critical for nicking the DNA strand and for forming the DNA hairpin. RAG-1 comprises a nonamer-binding region (NBR) that specifically binds the conserved nonamer (9 nucleotides) of the RSS and a central domain of RAG-1 binds specifically to the RSS heptamer. The core region of RAG-2 is predicted to form a six-bladed beta-propeller structure that appears less specific than RAG-1 for its target.

In some specific embodiments, RAG-1 as used herein refers to the human RAG-1 that comprises the amino acid sequence as disclosed by AAH37344.1. In yet some further specific embodiments, the human RAG-1 comprises the amino acid sequence as denoted by SEQ ID NO. 1. In yet some further embodiments, the human RAG-1 is encoded by the nucleic acid sequence as denoted by SEQ ID NO. 2. In some further embodiments, the invention further encompasses in some embodiments thereof the mouse RAG-1 as disclosed by NP_033045.2, and as the amino acid sequence denoted by SEQ ID NO. 3. In yet some further embodiments, the mouse RAG-1 is encoded by the nucleic acid sequence as denoted by SEQ ID NO. 4.

In yet some further specific embodiments, RAG-2 as used herein refers to the human RAG-2 that comprises the amino acid sequence as disclosed by NP_001230715.1. In yet some further specific embodiments, the human RAG-2 comprises the amino acid sequence as denoted by SEQ ID NO. 5. In yet some further embodiments, the human RAG-2 is encoded by the nucleic acid sequence as denoted by SEQ ID NO. 6. The invention further encompasses in some embodiments thereof the mouse RAG-2 as disclosed by NP_033046.1, and as denoted by SEQ ID NO. 7. In yet some further embodiments, the mouse RAG-2 is encoded by the nucleic acid sequence as denoted by SEQ ID NO. 8.

As indicated above, the invention provides methods for targeted insertion of a nucleic acid sequence of interest into a target locus. As used herein, a "target locus" is a region of DNA into which a nucleic acid sequence of interest is integrated, inserted and recombined within e.g. a region of DNA in a target cell. etc. In some specific embodiments the target locus is within the chromosomal DNA of the target cell. As used herein, a "target gene" or "endogenous gene" or "gene at a target locus" is a gene that naturally exists at a locus of integration, i.e. the gene that is endogenous to the target locus. Specific target loci relevant in connection with the present invention, will be described in more detail herein after. In yet some further specific non-limiting embodiments the target loci applicable in the present invention may comprise at least one RSS, specifically, at least one RSS flanking the target site. It should be noted that in some embodiments, the at least one RSS that flank the target site may follow the role of 12/23. More specifically, in some embodiments, where the nucleic acid sequence provided by the cassette of the invention is flanked by at least one 12-RSS, the target site may be flanked by at least one 23-RSS, and vice versa. Still further, as will be elaborated in more detail herein after, in some embodiments, an appropriate target loci may be the loci coding the TCR chains (alpha, beta, gamma and delta) and the loci coding the antibody chains (IgH, IgK, IgL).

The method of the invention involves the step of contacting the nucleic acid cassette provided by the method of the invention with the target cells. The term "contacting" means to bring, put, incubate or mix together. More specifically, in the context of the present invention, the term "contacting" includes all measures or steps, which allow the positioning of the nucleic acid cassettes of the present invention such that they are in direct or indirect contact with the target cell/s.

To induced DNA integration either in vitro or in vivo, the nucleic acid cassette of the invention may be provided to and/or contacted with the target cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The nucleic acid cassette may be provided to the target cells one or more times, e.g. one time, twice, three times, or more than three times, and the cells allowed to incubate with the nucleic acid cassette for some amount of time following each contacting event e.g. 16-24 hours.

The methods of the invention involve the provision of a nucleic acid cassette. The term "nucleic acid cassette" refers to a polynucleotide sequence comprising at least one regulatory sequence operably linked to a sequence encoding a nucleic acid sequence of interest that may be a protein-encoding or non-coding sequence. In some embodiments, the nucleic acid cassettes contain at least one nucleic acid sequence/s of interest, e.g., a polynucleotide(s) of interest. In other embodiments, the nucleic acid cassette may contain one or more genetic elements e.g. expression control sequences and at least one nucleic acid sequence/s of interest. In some embodiments, the nucleic acid cassettes of the invention may be comprised within a vector. Still further, vectors may comprise one, two, three, four, five or more nucleic acid cassettes. The nucleic acid cassette may be positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. The cassette may have its 3' and 5' ends adapted for ready insertion into a vector, e.g., it may possess restriction endonuclease sites at each end.

As indicated above, the RSS comprised within the nucleic acid cassette provided by the methods of the invention, may be required for RAG-mediated recombination. More specifically, "mediated" as used herein encompasses any process, specifically RAG-mediated recombination that may be either directly or indirectly caused by, facilitated, enhanced, associated with and/or performed by RAG complex.

In some specific embodiments, the nucleic acid cassette used by the method of the invention, or alternatively, the nucleic acid sequence of interest comprised therein, or both, may be flanked on both the 5' and 3' ends thereof by RSS.

In yet some further specific embodiments, the RSS in the cassette used by the method of the invention may be at least one of 12 RSS, 23 RSS and 22 RSS. In some particular and non-limiting embodiments, RSS applicable in the present invention may by any of the RSSs as denoted by nucleic acid sequence of SEQ ID NO. 36, 37, 38, 39, 40 and 41.

In some embodiments, the RSS used by the methods and cassettes of the invention may be naturally occurring. In yet some further embodiments, the RSS used by the methods and cassettes of the invention may be selected by a screen, rationally optimized, selected based on compatibility or incompatibility with other RSSs.

In certain embodiments, the cassette provided by the method of the invention may further comprise at least one genetic element. In more specific embodiments such genetic element may be at least one of: an internal ribosome entry site (IRES), a 2A peptide coding sequence, a promoter or functional fragments thereof, a splice donor, a splice acceptor, a degron, a 3 frame stop, a protein stabilizing sequence, a signal peptide, a stop codon, a polyadenylation site, a transcription enhancer, a switch region, an mRNA stabilizing sequence and a protein stabilizing sequence.

It should be noted that in some embodiments, each of the indicated genetic elements may be located either 5' or 3', or both, at the 5' and 3' (or in other words upstream and/or downstream), to the nucleic acid sequence of interest in the cassette provided by the methods of the invention. It should be noted that the terms used herein "5'" or "upstream" and "3'" or "downstream" both refer to a relative position in DNA or RNA. Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the DNA or RNA molecule and downstream is toward the 3' end. When considering double-stranded DNA, upstream is toward the 5' end of the protein coding strand for the gene in question and downstream is toward the 3' end. Due to the anti-parallel nature of DNA, this means the 3' end of the mRNA template strand is upstream of the gene and the 5' end is downstream. As used herein, the term "5'" refers to the part of the strand that is closer to the 5' end or 5' terminus, i.e. to the extremity of the DNA or RNA strand that has a phosphate group attached to the fifth carbon in the sugar-ring of the deoxyribose or ribose at its terminus. Furthermore, the term "3'" refers to the part of the strand that is closer to the 3' end or 3' terminus, i.e. to the extremity of the DNA or RNA strand that has a hydroxyl group linked to the 3rd carbon in the sugar-ring of the deoxyribose or ribose at its terminus.

As noted above, in some embodiments, the cassettes used by the methods of the invention may further comprise at least one IRES sequence.

By internal ribosome entry sequences (IRES) sequence is meant, a nucleotide sequence that allows for translation initiation in an end-independent manner, as part of the protein synthesis. IRES are able to recruit the eukaryotic ribosome to the mRNA and to provide two separate places where a ribosome may initiate translation on a single mRNA. IRES elements enable to create multigene, or polycistronic, messages since they are able to bypass the ribosome scanning model of 5' methylated Cap dependent translation and begin translation at internal sites. Multiple open reading frames can be transcribed together, each separated by an IRES, creating polycistronic messages. By virtue of the IRES element, each open reading frame is accessible to ribosomes for efficient translation.

It should be noted that in some embodiments, the IRES sequence may be located 5' to the nucleic acid sequence of interest. In some specific and non-limiting embodiments, an appropriate IRES that may be used by the invention may be the encephalomyocarditis virus (ECMV) IRES. In some particular and non-limiting embodiments, an ECMV IRES applicable in the present invention may comprise the nucleic acid sequence as denoted by SEQ ID NO. 27.

In yet some further embodiments, the cassette provided by the methods of the invention may further comprise at least one 2A peptide sequence. By an "internal ribosome entry site," or "IRES" it is meant a nucleotide sequence that allows for the initiation of protein translation in the middle of a messenger RNA (mRNA) sequence. More specifically, a 2A peptide sequence or a CHYSEL site causes a eukaryotic ribosome to release the growing polypeptide chain, but continue translating, thereby giving rise to two separate polypeptides from a single translating ribosome. An expression cassette using a 2A peptide may be therefore used for two or more nucleic acid sequences of interest. In some embodiments, this sequence may be used to separate the coding region of two or more polypeptides encoded by two or more nucleic acid sequences of interest. As a non-limiting example, the sequence encoding the 2A peptide may be between a first coding region and a second coding region. In other embodiments, the 2A peptide may be used in the polynucleotides of the present invention to produce two, three, four, five, six, seven, eight, nine, ten or more proteins, or any other product of the nucleic acid sequence of interest provided by the invention. In certain embodiments, non-limiting example for 2A-peptide that may be used by the invention may be the Picornaviruse 2A peptide (P2A) In some particular and non-limiting embodiments, a P2A peptide applicable in the present invention may comprise the nucleic acid sequence as denoted by SEQ ID NO. 28.

Still further, in some embodiments, the nucleic acid cassette provide by the method of the invention may further comprise at least one promoter or any functional fragments thereof. As used herein, a "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

In some embodiments, promoters applicable in the present invention may be either inducible or constitutive. In yet some further embodiments, a functional fragment of a promoter applicable in the methods and cassettes of the invention may be a minimal promoter. The term "minimal promoter" includes partial promoter sequences that define the start site of transcription for the linked sequence to be transcribed which by itself is not capable of initiating transcription. Thus, the activity of such a minimal promoter is dependent upon the binding of a transcriptional activator to an operatively linked regulatory sequence, e.g., enhancer. In certain embodiments a minimal promoter may be included in the cassettes of the invention. In some specific embodiment, the minimal promoter may be a Variant of IGH minimal promoter. In some particular embodiments such minimal promoter may comprise the nucleic acid sequence as denoted by SEQ ID NO: 34. In yet some alternative embodiments, a minimal promoter applicable in the present invention may be an IgK Minimal Promoter. In more specific embodiments such minimal promoter may comprise the nucleic acid sequence as denoted by SEQ ID NO: 35.

A "constitutive promoter" refers to a promoter that allows for continual transcription of the coding sequence or gene under its control.

In yet some further embodiments, a promoter suitable in the cassette of the invention may be an inducible promoter. An "inducible promoter" refers to a regulatory region that is operably linked to one or more genes, wherein expression of the gene(s) is increased in the presence of an inducer of said regulatory region. An "inducible promoter" refers to a promoter that initiates increased levels of transcription of the coding sequence or gene under its control in response to a stimulus or an exogenous environmental condition.

It should be appreciated that the promoters suitable for the present invention may be either endogenous or heterologous. The phrase "endogenous promoter" includes a promoter that is naturally associated, e.g., in a wild-type organism, with an endogenous gene. Thus, in some specific embodiments, the cassette of the invention may comprise or operably liked to an endogenous promoter, for example, the endogenous promoter of the Ig heavy chain, Ig light chain or the TCR beta or alpha chains. It should be appreciated that such endogenous promoter may be either ectopically added or may be used in its original endogenous location.

In yet some further embodiments, the cassette of the invention may comprise heterologous promoter. The term "heterologous" includes a promoter from a different source or gene. It should be understood that in some embodiments, a promoter comprised within the nucleic acid cassette of the invention may be located 5' to the nucleic acid sequence of interest. In some embodiments, relevant promoters that may be used by the methods and cassettes of the invention may include but are not limited to CMV promoter, SFFV promoter, EF1alpha promoter, AAT promoter, BgH promoter and any appropriate promoter.

In some embodiments, the targeted cassettes of the invention may include 2A peptide or an IRES sequence upstream to the receptor/Ab gene in order to avoid formation of protein fusions with preceding segments while still utilizing the strong endogenous promoter. The IRES may be preceded by a 3-frame stop to prevent ongoing translation. In some embodiments, the vectors may encode several peptides (e.g. two Ab chains) and these are separated by 2A peptides.

In yet some further embodiments, the cassettes provided by the invention and by the methods and compositions of the invention may further comprise at least one degron sequence. Degrons are readily understood by one of ordinary skill in the art to be amino acid sequences that control the stability of the protein of which they are part. In some embodiments, a suitable degron comprised within the nucleic acid cassette of the invention may be constitutive. In yet some further embodiments, the degron may exerts its influence on protein in an inducible manner. In some embodiments, the degron sequence may be located 5' to the nucleic acid sequence of interest.

In yet some further embodiments, the nucleic acid cassette provided by the invention and by the methods and compositions of the invention may comprise at least one signal peptide. "Signal peptide", as used herein, shall mean a peptide chain (of about 3-60 amino acids long) that directs the post-translational transport of a protein to the endoplasmic reticulum and may be cleaved off.

In some embodiments, the signal peptide may be located 5' to the nucleic acid sequence of interest.

In some further embodiments, the nucleic acid cassette provided by the invention and by the methods and compositions of the invention may comprise at least one mRNA stabilizing sequence. As used herein, a mRNA stabilizing sequence refers to a nucleic acid sequence that enables to extend the life-time of a mRNA strand. Non limiting examples of mRNA stabilizing elements may include Polyadenylation, 3' untranslated regions (3'-UT) such as histone mRNA 3'-terminal stem-loop, AU-rich elements (AUREs), Iron-responsive element and Long-range stem loop of insulin-like growth factor II (IGF II), mRNA cap.

In some embodiments, the mRNA stabilizing sequence may be located 3' to the nucleic acid sequence of interest.

In yet some further embodiments, the cassette provided by the invention and by the methods and compositions of the invention may comprise at least one stop codon. A stop codon (or termination codon) is a nucleotide triplet within messenger RNA that signals a termination of translation into proteins. Stop codons signal the termination of this process by binding release factors, which cause the ribosomal subunits to disassociate, releasing the amino acid chain. There are three different stop codons in RNA; UAG ("amber"), UAA ("ochre"), UGA ("opal"), in DNA; TAG ("amber"), TAA ("ochre"), TGA ("opal" or "umber"). It should be noted that in some embodiments, the stop codon may be located 3' to the nucleic acid sequence of interest.

In yet some further embodiments, the cassette provided by the invention and by the methods and compositions of the invention may comprise at least one 3-frame stop codon sequence. More specifically, the cassette may comprise protein translation stop codons in each frame of translation, so that translation from the transcripts of any nucleic acid sequence of interest is halted at the point of insertion. Each translation stop sequence (known henceforth as a "3 frame stop codon sequence") carries stop codons in all 3 frames of translation. In some embodiments, the 3 frame stop codon sequence may be located 5' to the nucleic acid sequence of interest.

Still further, in certain embodiments, the cassette provided by the invention and by the methods and compositions of the invention may comprise a nucleic acid sequence encoding at least one protein stabilizing sequence. A protein stabilizing sequence relates to an amino acid sequence useful for stabilization of otherwise unstable proteins, particularly proteolytically sensitive proteins. The stabilization sequence may include a limited number of amino acids ranging from about ten to about 50 residues. The amino acids is such that the secondary and tertiary structure assumes the form of an outwardly directed, properly aligned hydrophobic face and a positively charged polar face. Non-limiting example of protein stabilizing sequence useful in the present invention may comprise the amino acid sequence as denoted by SEQ ID NO: 9. In some embodiments, the protein stabilizing sequence may be located 5' to the nucleic acid sequence of interest.

Still further, in some embodiments, the cassette provided by the invention and by the methods and compositions of the invention may comprise at least one polyadenylation sequence. Polyadenylation is the addition of a poly(A) tail to a messenger RNA consisting of multiple adenosine monophosphates. In eukaryotes, polyadenylation is part of the process that produces mature messenger RNA (mRNA) for translation. The process of polyadenylation begins as the transcription of a gene terminates. The 3'-most segment of the newly made pre-mRNA is first cleaved off by a set of proteins; these proteins then synthesize the poly(A) tail at the RNA's 3' end. The polyadenylation signal varies between groups of eukaryotes. Most human polyadenylation sites contain the AAUAAA sequence. In some embodiments, the polyadenylation sequence may be located 3' to the nucleic acid sequence of interest.

In certain embodiments, the cassette provided by the invention and by the methods and compositions of the invention may comprise at least one splice donor site. In yet some further embodiments, the cassette provided by the methods of the invention may comprise at least one splice acceptor site. More specifically, splicing is the editing of the nascent precursor messenger RNA (pre-mRNA) transcript. After splicing, introns are removed and exons are joined together. Introns often reside within the sequence of eukaryotic protein-coding genes. Within the intron, a donor site (5' end of the intron), a branch site (near the 3' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. Upstream (5'-ward) from the AG there is a region high in pyrimidines (C and U), or polypyrimidine tract. Further upstream from the polypyrimidine tract is the branch point, which includes an adenine nucleotide involved in lariat formation. In some embodiments, a splice donor (SD) may be provided downstream of the receptor/Ab gene to facilitate utilization of the endogenous C segment(s) upon integration, transcription and splicing. In particular, the SD is required to allow class switching of targeted Abs. Thus, in some embodiments, the SD may be located 3' to the nucleic acid sequence of interest. In some specific and non-limiting embodiments, a splice acceptor (SA) applicable in the present invention may be the SA 97.66. In some specific embodiments such SA may comprise the nucleic acid sequence as denoted by SEQ ID NO: 26. In yet some further embodiments, a splice acceptor (SA) used by the invention may be the SA EF1a. More specifically, such SA may comprise the nucleic acid sequence as denoted by SEQ ID NO: 31. In some further embodiments, a splice donor (SD) that may be used by the invention may be the SD mIGHJ1/J4. In more specific embodiments, such SD may comprise the nucleic acid sequence as denoted by SEQ ID NO: 32. In yet some further embodiments a splice donor used by the invention may be the SD IgHJ3 SD 98.84. In more specific embodiments, such SD may comprise the nucleic acid sequence as denoted by SEQ ID NO: 33.

Still further, in some embodiments, the cassette provided by the invention and by the methods and compositions of the invention may comprise at least one enhancer. A transcription enhancer is a short (50-1500 bp) region of DNA that can be bound by proteins (activators) to increase the likelihood that transcription of a particular gene will occur. These proteins are usually referred to as transcription factors. Enhancers are generally cis-acting, but can also be trans-acting (acting away from the gene) and can be located up to 1 Million bp (1,000,000 bp) away from the gene and can be upstream or downstream from the start site, and either in the forward or backward direction. There are hundreds of thousands of enhancers in the human genome. The invention thus encompasses in some embodiments thereof the use of any suitable enhancer. In some embodiments, the enhancer sequence may be located 3' to the nucleic acid sequence of interest.

It should be noted that the polynucleotide of the cassette of the invention may also comprise sequences, e.g. restriction sites, nucleotide polymorphisms, selectable markers etc., which may be used to assess for successful insertion of the gene of interest at the cleavage site. In addition, the V(D)J targeting cassette of the invention may also comprise a vector backbone containing sequences that are not homologous to the DNA region of interest and that are not intended for insertion into the DNA region of interest.

In certain embodiments, the cassette provided by the methods of the invention may comprise two or more nucleic acid sequences of interest separated by at least one genetic element, specifically, any of the gene elements disclosed above. In more specific embodiments such genetic element may be at least one of: an IRES, a 2A peptide coding sequence and a promoter and any functional fragments thereof. Thus, in some embodiments the cassettes of the invention may comprise at least two, three, four, five, six, seven, eight, nine, ten or more, fifteen, twenty, twenty five, thirty, thirty five, forty, forty five, fifty, fifty five, sixty, sixty five, seventy, seventy five, eighty, eighty five, ninety, ninety five, hundred or more nucleic acid sequences of interest separated by at least one genetic element.

As discussed above, more than one nucleic acid sequence of interest may be integrated by the V(D)J targeting methods of the invention, for example, two or more genes of interest may be integrated, three or more genes may be integrated, four or more genes may be integrated, e.g. five or more, six, seven, eight, nine, ten or more genes may be integrated into the target locus. In such instances, multiple 2A peptides or IRESs may be used to create a bicistronic or multicistronic V(D)J targeting cassette.

Alternatively, additional coding sequences of interest may be provided on the V(D)J targeting cassette under the control of a promoter distinct from that of the gene at the target locus.

In yet some further embodiments, the nucleic acid sequence of interest may be a protein coding sequence or a non-coding sequence.

A "coding sequence", as used herein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxyl) terminus.

In yet some further embodiments, the nucleic acid sequence of interest may be a non-coding gene. Such gene may be transcribed in some embodiment into a non-coding RNA that will be described in more detail herein after.

In certain embodiments, the nucleic acid sequence of interest may be a protein coding nucleic acid sequence. In more specific embodiments, the nucleic acid sequence of interest may encode at least one of, a therapeutic protein or peptide, a prophylactic protein, a tolerizing protein, an immunizing protein, a toxic protein, an inducible suicide protein, a marker protein, an imaging protein and a fusion or chimeric protein.

More specifically, in some embodiments, the nucleic acid sequence of interest may encode a therapeutic and/or prophylactic protein. In some instances, the therapeutic protein alters the activity or function of the cell in which the therapeutic protein is expressed. In other words, the therapeutic protein has a cell-intrinsic effect. For example, the therapeutic and/or prophylactic protein may be an intracellular protein, transmembrane protein or secreted protein that, when expressed in a cell, will substitute for, or "complement", a mutant protein in the cell. In other instances, the therapeutic and/or prophylactic protein alters the activity of cells other than cells in which the agent is expressed. In other words, the therapeutic and/or prophylactic protein has a cell-extrinsic effect. For example, the integrated gene of interest may encode a cytokine, chemokine, growth factor, hormone, antibody, or cell surface receptor or any chimeric or fusion protein thereof that modulates the activity of the target cell or of other cells. In yet some further embodiments, any of the proteins disclosed above may be used for the treatment and/or prophylaxis of a pathologic disorder and therefore may be referred to herein as therapeutic and/or prophylactic proteins.

In yet some further embodiments, the protein encoded by the nucleic acid sequence comprised within the cassette provided by the invention and by the methods and compositions of the invention may be an immunizing protein. An "immunizing protein" refers to a protein that elicits immunization, a process by which a subject's immune system becomes fortified against an agent (known as the immunogen). Immunizing proteins orchestrate an immune response, and also develop the ability to quickly respond to a subsequent encounter because of immunological memory: a function of the adaptive immune system.

In certain embodiments, the protein encoded by the nucleic acid sequence comprised within the cassette provided by the invention and by the methods and compositions of the invention may be a tolerizing protein. More specifically, a protein that may induce tolerization in a subject. In yet some specific embodiments, such tolerizing protein may be any peptide in the context of coagulation disorders (factor 9, factor 8, factor 7), type I diabetes (GAD, insulin, proinsulin, HSP60, ECDISP) and Rheumatoid arthritis (DNAJ).

In some embodiments, the protein encoded by the nucleic acid sequence of interest may be a suicide gene product.

As used herein, the term "suicide gene" refers to a class of genes that produce proteins that promote the death of cells in which they expressed. Suicide genes that can be employed in the nucleic acid cassette provided by the methods of the present disclosure include the caspases, CASP3, CASP8, CASP9, BAX, DFF40 and Fas. Further non-limiting examples of suicide genes include genes that encode a peptide or polypeptide that is cytotoxic either alone or in the presence of a cofactor, e.g. a toxin such as abrin, ricin A, *pseudomonas* exotoxin, cholera toxin, diphtheria toxin, Herpes Simplex Thymidine Kinase (HSV-TK) and cytidine deaminase and genes that target a cell for ADCC or CDC-dependent death, e.g. CD20. It should be noted that in some embodiments a suicide gene may be a toxic gene. In some embodiments, a suicide gene may be added to the cassette which may be inducible i.e. which expression may be controlled at wish. In particular embodiments, an upstream caspase gene fused to an inducible dimerization domain (for example iCasp9) may be added to the cassette, as the default expression of iCasp9 is as an inactive monomeric caspase. In some particular and non-limiting embodiments, VDJ targeting in accordance with the invention may be employed to target the iCasp9 that comprises the nucleic acid sequence as denoted by SEQ ID NO. 17. According to the present invention, the induction of iCasp9 may depend on the administration of the small molecule dimerizer, specifically, the drug AP1903 (e.g., Drug Bank accession number DB04974) and dimerization results in rapid induction of apoptosis.

In yet some further embodiments, the protein encoded by the nucleic acid sequence of interest may be a marker protein. A marker protein may be a cell membrane-protein that serves as an identifier of the cell. A marker protein refers to a polypeptide that can determine whether or not the targeted nucleic acid cassette is expressed, therefore enabling detection. A marker protein type is not particularly limited, provided that it can be detected by a method known in the art. Examples thereof include a fluorescent protein, a pigment synthetic protein, a photoprotein, an excretory-secretory protein, and a protein that controls an external configuration. The marker proteins may enable visual detection under particular conditions without changing an external configuration.

In certain embodiments, the protein encoded by the nucleic acid sequence of interest may be an imaging protein. More specifically, the above-described marker protein may also be an "imaging protein", i.e. a protein that is conjugated to a detectable label, which can be any molecule or agent that can emit a signal that is detectable by imaging. In some embodiments, the subject methods and compositions may be used to follow cells of interest, e.g. cells comprising an integrated nucleic acid sequence of interest. As such, the gene of interest (or one of the genes of interest) to be integrated may encode for a imaging marker. By an "imaging marker" it is meant a non-cytotoxic agent that can be used to locate and, optionally, visualize cells, e.g. cells that have been targeted by the cassettes, methods, vectors and compositions of the subject application. An imaging moiety may require the addition of a substrate for detection, e.g. horseradish peroxidase (HRP), β-galactosidase, luciferase, and the like. Alternatively, an imaging moiety may provide a detectable signal that does not require the addition of a substrate for detection, e.g. a fluorophore or chromophore dye, e.g. Alexa Fluor 488® or Alexa Fluor 647®, or a protein that comprises a fluorophore or chromophore, e.g. a fluorescent protein. As used herein, a fluorescent protein (FP) refers to a protein that possesses the ability to fluoresce (i.e., to absorb energy at one wavelength and emit it at another wavelength). For example, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein and variants thereof.

As some further examples, the subject methods and compositions may be used to isolate cells of interest, e.g. cells comprising an integrated nucleic acid sequence of interest. Towards this end, the nucleic acid sequence of interest (or at least one of the nucleic acid sequences of interest) to be integrated may encode for a selectable marker. By a "selectable marker" it is meant an agent that can be used to select cells, e.g. cells that have been targeted by compositions of the subject application. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the nucleic acid sequence of interest. Any convenient selectable marker may be employed, for example, a drug selectable marker, e.g. a marker that prevents cell death in the presence of drug, a marker that promotes cell death in the presence of drug, an imaging marker, etc.; an imaging marker that may be selected for using imaging technology, e.g. fluorescence activated cell sorting; a polypeptide or peptide that may be selected for using affinity separation techniques, e.g. fluorescence activated cell sorting, magnetic separation, affinity chromatography, "panning" with an affinity reagent attached to a solid matrix, etc.; and the like.

In yet some alternative embodiments, the nucleic acid sequence of interest may be a non-coding sequence, specifically, this sequence may encode, in some non-limiting embodiments, an RNA molecule that is not translated into a protein. In yet some further specific embodiments, the nucleic acid sequence of interest may encode at least one small non-coding RNA molecule.

In yet some further embodiments, the small non-coding RNA molecule may be a molecule that control the expression of proteins, for example, an RNA molecule that participate in silencing of a target nucleic acid sequence. Suitable targets for such RNA silencing may include but are not limited to genes encoding any one of a TCR chain, a BCR chain, an immune checkpoint gene, an apoptotic gene or any gene involved in cell cycle, differentiation and survival.

In some specific embodiments, the nucleic acid sequence of the invention may encode an RNA silencing agent. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene or RNA sequence. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In some embodiments, the RNA silencing agent is capable of inducing RNA interference. In other embodiments, the RNA silencing agent is capable of mediating translational repression. More specifically, the nucleic acid sequence of interest according to the invention may encode an "antisense RNA", which is a single strand RNA (ssRNA) molecule that is complementary to an mRNA strand of a specific target gene product. Antisense RNA may inhibit the translation of a complementary mRNA by base-pairing to it and physically obstructing the translation machinery. By "complementary" it is meant the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes.

In yet some specific embodiments, the nucleic acid sequence of the invention may encode an RNA, specifically, dsRNA molecule participating in RNA interference. RNA interference (RNAi), as indicated above, is a general conserved eukaryotic pathway which down regulates gene expression in a sequence specific manner. It is the process of sequence-specific, post-transcriptional gene silencing in animals and plants, initiated by siRNA that is homologous in its duplex region to the sequence of the silenced gene. Gene silencing is induced and maintained by the presence of partly or perfectly double-stranded RNA (dsRNA). The silenced genes may be endogenous or exogenous to the organism, integrated into a chromosome or present in a transfection vector that is not integrated into the genome. The expression of the gene is either completely or partially inhibited.

More specifically, the dsRNA encoded by the nucleic acid sequence of interest encompassed by the invention may be selected from the group consisting of small interfering RNA (siRNA), MicroRNA (miRNA), short hairpin RNA (shRNA), PIWI interacting RNAs (piRNAs). As known in the art RNAi is a multistep process. In a first step, there is cleavage of large dsRNAs into 21-23 ribonucleotides-long double-stranded effector molecules called "small interfering RNAs" or "short interfering RNAs" (siRNAs). These siRNAs duplexes then associate with an endonuclease-containing complex, known as RNA-induced silencing complex (RISC). The RISC specifically recognizes and cleaves the endogenous mRNAs containing a sequence complementary to one of the siRNA strands. One of the strands of the double-stranded siRNA molecule comprises a nucleotide sequence that is complementary to a nucleotide sequence of the target gene, or a portion thereof, and the second strand of the double-stranded siRNA molecule comprises a nucleotide sequence substantially similar to the nucleotide sequence of the target gene, or a portion thereof.

In more particular embodiments, siRNAs comprise a duplex, or double-stranded region, of about 18-25 nucleotides long. Often, siRNAs contain from about two to four unpaired nucleotides at the 3' end of each strand. At least a portion of one strand of the duplex or double-stranded region of a siRNA is substantially homologous to or substantially complementary to a target sequence within the gene product molecule as herein defined.

The strands of a double-stranded interfering RNA (e.g., siRNA) may be connected to form a hairpin or stem-loop structure (e.g., shRNA). Thus, the RNA silencing agent encoded by the nucleic acid sequence of interest according to the present invention may also be a short hairpin RNA (shRNA). The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including about 3 to 23. Some of the nucleotides in the loop can be involved in base-pair interactions with other nucleotides in the loop. According to other embodiments the RNA silencing agent encoded by the nucleic acid if interest in accordance with the invention may be a micro-RNA (miRNA). miRNAs are small RNAs made from genes encoding primary transcripts of various sizes. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target).

The pre-miRNA is a substrate for a form of dicer that removes the miRNA duplex from the precursor, after which, similarly to siRNAs, the duplex can be taken into the RISC complex.

In yet some specific embodiments, the nucleic acid sequence of interest may encode at least one of a receptor and an antibody or any fragment/s or chimera/s thereof.

In some particular embodiments, the nucleic acid sequence of interest comprised within the cassette of the invention, used and provided by the methods and compositions of the invention may encode at least one receptor. A receptor molecule as used herein refer to a molecular structure or site, specifically a protein on the surface or interior of a cell that binds with ligand substances such as hormones, antigens, drugs, or neurotransmitters. In more specific embodiments such receptor may be at least one of a T cell receptor (TCR), chimeric antigen receptor (CAR) and a B cell receptor (BCR), or any combinations thereof. In some embodiments, the nucleic acid sequence of interest may encode a receptor that may be a naturally occurring receptor, receptor selected by a screen or rationally designed receptor.

In yet some further embodiments, the protein encoded by the nucleic acid sequence comprised within the cassette provided by the methods of the invention may be a T-cell receptor (TCR). The TCR is a disulfide-linked membrane-anchored heterodimeric protein normally consisting of the highly variable alpha (α) and beta (β) chains expressed as part of a complex with the invariant CD3 chain molecules. T cells expressing this receptor are referred to as α:β (or αβ) T cells, though a minority of T cells express an alternate receptor, formed by variable gamma (γ) and delta (δ) chains, referred as γδ T cells. Each chain is composed of two extracellular domains: Variable (V) region and a Constant (C) region. The variable domain of both the TCR α-chain and β-chain each have three hypervariable or complementarity determining regions (CDRs), as well as framework regions (FRs) and a constant region. The sequence diversity of a beta T cells is largely determined by the amino acid sequence of the third complementarity-determining region (CDR3) loops of the α and β chain variable domains, which diversity is a result of V(D)J recombination. In some embodiments, a V(D)J targeting cassettes in accordance with the invention that encode a TCR may be particularly useful in targeting insertion into a target locus in T cells. In some particular embodiments, a BCR that may be used in the invention may be the ESO-1-specific TCR. In more specific embodiments, such TCR may comprise the nucleic acid as denoted by SEQ ID NO: 12.

In some further embodiments, the protein encoded by the nucleic acid sequence comprised within the cassette provided by the methods of the invention may be a B-cell receptor (BCR). The B-cell receptor or BCR is a transmembrane receptor protein located on the outer surface of B cells. The B-cell receptor is composed of two elements, specifically, (i) a membrane-bound immunoglobulin molecule of one isotype (IgD, IgM, IgA, IgG, or IgE) with the exception of the presence of an integral membrane domain, these are identical to their secreted forms; and (ii) a signal transduction moiety composed of a heterodimer called Ig-α/Ig-β (CD79), bound together by disulfide bridges. Each member of the dimer spans the plasma membrane and has a cytoplasmic tail bearing an immunoreceptor tyrosine-based activation motif (ITAM). It should be appreciated that in some embodiments, a cassette encoding a BCR may be particularly useful in targeting insertion into a target locus in B cells. In some particular embodiments, a BCR that may be used in the invention may be the anti-polio BCR. In more specific embodiments, such BCR may comprise the nucleic acid as denoted by SEQ ID NO: 23. In yet some further particular embodiments, a BCR that may be used by the invention may be the anti-Respiratory syncytial virus (RSV) BCR. In some specific embodiments, such BCR may comprise the nucleic acid as denoted by SEQ ID NO: 24.

It should be noted that "receptor" as used herein also encompasses any variant, chimeric or fusion protein of any of the receptors described herein, specifically, TCR or BCR chimeric or fusion proteins. Cancer immunotherapy aims to augments immune mechanisms to fight malignancies. In particular, adoptive T cell transfer entails the activation and expansion of T cells that target tumor associated antigens (TAA). Naturally occurring T cell receptors (TCRs) often have low affinity against TAAs. However, T cells can be engineered to express highly potent TCRs, which can recognize fragments of both intracellular and cell surface proteins when presented in a major histocompatibility complex (MHC) context. Alternatively, T cells can be engineered to express chimeric antigen receptors (CARs), which have a high TAA affinity. As used herein, the term "fusion or chimeric protein" refers to a recombinant protein in which two or more proteins or domains responsible for a specific function within a protein are linked so that each protein or domain is responsible for its intrinsic function. A linker having a flexible structure may conventionally be inserted between the two or more proteins or domains.

In some further embodiments, the protein encoded by the nucleic acid sequence comprised within the cassette provided by the methods of the invention may be a Chimeric antigen receptor (CAR). CAR, as used herein, relates to artificial T cell receptors (also known as chimeric T cell receptors, chimeric immuno-receptors). These are engineered receptors, which graft an arbitrary specificity onto an immune effector cell. Typically, these receptors are used to graft the specificity of a monoclonal antibody onto a T cell.

The initial design (also referred to a first generation) joined an antibody-derived scFv to the CD33 intracellular signaling domain of the T-cell receptor through hinge and transmembrane domains.

Second generation CARs add intracellular signaling domains from various costimulatory protein receptors (e.g., CD28, 41BB, ICOS) to the cytoplasmic tail of the CAR to provide additional signals to the T cell. More recent, third generation CARs combine multiple signaling domains, such as CD27, CD28, 4-1BB, ICOS, or OX40, to augment potency.

CD19 is a B-cell surface protein expressed throughout B-cell development; therefore, it is expressed on nearly all B-cell malignancies, including chronic lymphocytic leukemia (CLL), ALL, and many non-Hodgkin lymphomas. This near-universal expression and specificity for a single cell lineage has made CD19 an attractive target for CAR-modified T-cell therapies. Additional B-cell-specific cell-surface molecules, such as CD22, may hold similar promise and are under active investigation, and may therefore be also applicable in the present invention.

Thus, in some particular and non-limiting embodiments, VDJ targeting may be employed to target an anti CD19 CAR coding nucleic acid sequence which are highly effective in treating B cell malignancies. In yet some further specific embodiments, VDJ targeting according to the invention may be employed to target the nucleic acid sequence that encodes the anti CD19 CAR, specifically, such anti CD19 CAR may comprise in some embodiments, the amino acid sequence as denoted by SEQ ID NO 10 or any homologs, variants or derivatives thereof. Thus, in some embodiments, the cassettes provided by the invention and used by the methods and compositions discussed herein may comprise as at least one nucleic acid sequence of interest, a nucleic acid sequence encoding the polypeptide as denoted by SEQ ID NO. 10.

In yet some further specific embodiments, VDJ targeting in accordance with the invention may be employed to insert an anti-Tn-MUC1 CAR coding nucleic acid sequence which targets a highly cancer specific glycoform. Aberrant expression of Tn glycoforms (GalNAc-Ser/Thr) have in particular been found on the cell membrane mucin MUC1, which is a large protein with tandem repeated sequences carrying O-glycans overexpressed in most adenocarcinomas. In health, the Tn antigen is not expressed and humans have natural anti-Tn IgM antibodies. However, exposure of Tn in cancer cells may lead to loss of immunological tolerance to Tn-glycopeptide epitopes, induction of IgG antibodies and immunopathology. In some particular and non-limiting embodiments, the CAR-ANTI-Tn-MUC1 may be encoded a nucleic acid sequence comprising the nucleic acid sequence as denoted by SEQ ID NO. 11. Thus, in some embodiments, the VDJ targeting according to the invention may be employed to target the nucleic acid sequence as denoted by SEQ ID NO. 11 that encodes the CAR-ANTI-Tn-MUC1, or any homologs, variants or derivatives thereof. Thus, in some embodiments, the cassettes provided by the invention and used by the methods and compositions discussed herein may comprise as at least one nucleic acid sequence of interest, a nucleic acid sequence encoding the polypeptide as denoted by SEQ ID NO. 11. In some embodiments, VDJ targeting may be employed for targeted insertion of an NY-ESO-1-specific TCR construct. NY-ESO-1 (also known as CTAG-1B) is an immunogenic cancer testis antigen (CTA) associated with spontaneous and vaccine-induced immunity that can lead to clinical cancer responses. Up to 60% of advanced myelomas have been reported to express NY-ESO-1, a feature correlated to tumor proliferation and high risk features. Thus, in certain specific embodiments, VDJ targeting according to the invention may be employed to target the nucleic acid sequence that encodes the anti-NY-ESO-1-TCR. In more specific embodiments, the NY-ESO-1-TCR may comprise the amino acid sequence as denoted by SEQ ID NO 12. Thus, in some embodiments, the cassettes provided by the invention and used by the methods and compositions discussed herein may comprise as at least one nucleic acid sequence of interest, a nucleic acid sequence encoding the polypeptide as denoted by SEQ ID NO. 12.

The nucleic acid sequence of interest comprised within the cassette provide by the invention may encode a protein or polypeptide as described herein above (e.g., receptors or antibodies). The term "polypeptide" as used herein refers to amino acid residues, connected by peptide bonds. A polypeptide sequence is generally reported from the N-terminal end containing free amino group to the C-terminal end containing free carboxyl group and may include any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man. More specifically, "Amino acid sequence" or "peptide sequence" is the order in which amino acid residues connected by peptide bonds, lie in the chain in peptides and proteins. The sequence is generally reported from the N-terminal end containing free amino group to the C-terminal end containing amide. Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, manosylation, amidation, carboxylation, sulfhydryl bond formation, cleavage and the like.

It should be appreciated that the invention encompasses the use of any variant or derivative of the polypeptides of the invention and any polypeptides that are substantially identical or homologue to the polypeptides encoded by the nucleic acid sequence of the invention. The term "derivative" is used to define amino acid sequences (polypeptide), with any insertions, deletions, substitutions and modifications to the amino acid sequences (polypeptide) that do not alter the activity of the original polypeptides. By the term "derivative" it is also referred to homologues, variants and analogues thereof. Proteins orthologs or homologues having a sequence homology or identity to the proteins of interest in accordance with the invention, specifically, receptors, chimeras and antibodies described herein, may share at least 50%, at least 60% and specifically 65%, 70%, 75%, 80%, 85%, 90%, 91%, 92%, 93%, 94%, 95%, 96%, 97%, 98%, 99%, or higher, specifically as compared to the entire sequence of the proteins of interest in accordance with the invention, for example, any of the proteins that comprise the amino acid sequence as denoted by SEQ ID NO. 10, 11 and 12, as well as the BCRs sequences as denoted by SEQ ID NO. 23 and 24 and the antibodies sequences described herein after, specifically the sequences as denoted by SEQ ID NO. 13, 14, 15 and 16. Specifically, homologs that comprise or consists of an amino acid sequence that is identical in at least 50%, at least 60% and specifically 65%, 70%, 75%, 80%, 85%, 90%, 91%, 92%, 93%, 94%, 95%, 96%, 97%, 98%, 99%, or higher to SEQ ID NO. 10, 11, 12, 13, 14, 15, 16, 23, 24 specifically, the entire sequence as denoted by SEQ ID NO. 10, 11, 12, 13, 14, 15, 16, 23, 24.

In some embodiments, derivatives refer to polypeptides, which differ from the polypeptides specifically defined in the present invention by insertions, deletions or substitutions of amino acid residues. It should be appreciated that by the terms "insertion/s", "deletion/s" or "substitution/s", as used herein it is meant any addition, deletion or replacement, respectively, of amino acid residues to the polypeptides disclosed by the invention, of between 1 to 50 amino acid residues, between 20 to 1 amino acid residues, and specifically, between 1 to 10 amino acid residues. More particularly, insertion/s, deletion/s or substitution/s may be of any one of 1, 2, 3, 4, 5, 6, 7, 8, 9, or 10 amino acids. It should be noted that the insertion/s, deletion/s or substitution/s encompassed by the invention may occur in any position of the modified peptide, as well as in any of the N' or C' termini thereof. With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Thus, in some embodiments, the invention encompasses targeting of any nucleic acid sequence of interest that encodes any of the specified polypeptides (e.g., receptors, chimeric receptors and antibodies), or any derivatives thereof, specifically a derivative that comprise at least 1, 2, 3, 4, 5, 6, 7, 8, 9, 10 or more conservative substitutions to the amino acid sequences as denoted by any one of SEQ ID NO. 10, 11, 12, 13, 14, 15, 16, 23, 24. More specifically, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

Variants of the polypeptides of the invention may have at least 80% sequence similarity or identity, often at least 85% sequence similarity or identity, 90% sequence similarity or identity, or at least 95%, 96%, 97%, 98%, or 99% sequence similarity or identity at the amino acid level, with the protein of interest, such as the various polypeptides of the invention.

In yet some alternative embodiments, the nucleic acid sequence of interest comprised within the cassette of the invention may encode at least one antibody or any antibody binding domains, fragments or portions thereof. In more specific embodiments, such antibody may be at least one of a full length antibody, antibody fragment, single-chain variable fragment (scFv), bi-specific antibody, tri-specific antibody, Bi-specific T-cell engagers (BiTE) and variable new antigen receptor antibody (V-NAR).

In some embodiments, the nucleic acid sequence of interest may encode an antibody that may be a naturally occurring antibody, antibody or fragments thereof selected by a screen or rationally designed antibody.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen or antigen-binding scaffolds. The antigen binding domains in accordance with the invention may recognize and bind a specific antigen or epitope. It should be therefore noted that the term "binding specificity", "specifically binds to an antigen", "specifically immuno-reactive with", "specifically directed against" or "specifically recognizes", when referring to an antigen or particular epitope, refers to a binding reaction which is determinative of the presence of the epitope in a heterogeneous population of proteins and other biologics. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. Still further, as indicated above, an "antigen-binding domain" can comprise or consist of an antibody or antigen-binding fragment of an antibody. The term "antibody" as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The antibody suitable for the invention may also be a bi-specific antibody (such as Bi-specific T-cell engagers-BiTEs) or a tri-specific antibody.

The antibody suitable for the invention may also be a variable new antigen receptor antibody (V-NAR). VNARs are a class of small, immunoglobulin-like molecules from the shark immune system. Humanized versions of VNARs could be used to bind protein epitopes that are difficult to access using traditional antibodies.

Still further, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

It should be noted that in some specific embodiments, the receptor or antibody encoded by the nucleic acid sequence of interest of the cassette of the invention may be directed at or specific for a tumor associated antigen (TAA).

Tumor or cancer associated antigen, as used herein may be an antigen that is specifically expressed, over expressed or differentially expressed in tumor cells. In yet some further embodiments, TAA can stimulate tumor-specific T-cell immune responses. Exemplary tumor antigens that may be applicable in the present invention, include, but are not limited to, RAGE-1, tyrosinase, MAGE-1, MAGE-2, NY-ESO-1, Melan-A/MART-1, glycoprotein (gp) 75, gp100, MUC1, beta-catenin, PRAME, MUM-1, WT-1, CEA, PR-1 CD45, glypican-3, IGF2B3, Kallikrein4, KIF20A, Lengsin, Meloe, MUC5AC, survivin, CLPP, Cyclin-A1, SSX2, XAGE1b/GAGED2a, MAGE-A3, MAGE-A6, LAGE-1, CAMEL, hTRT and Eph. and TRP-1. Still further, TAA may be recognized by CD8+ T cells as well as CD4+ T cells. Non limiting examples of TAA recognized by CD8+ T cells may be CSNK1A1, GAS7, HAUS3, PLEKHM2, PPP1R3B, MATN2, CDK2, SRPX (P55L), WDR46 (T227I), AHNAK (S4460F), COL18A1 (S126F), ERBB2 (H197Y), TEAD1 (L209F), NSDHL (A290V), GANAB (S184F), TRIP12 (F1544S), TKT (R438W), CDKN2A (E153K), TMEM48 (F169L), AKAP13 (Q285K), SEC24A (P469L), OR8B3 (T1901), EXOC8 (Q656P), MRPS5 (P59L), PABPC1 (R520Q), MLL2, ASTN1, CDK4, GNL3L, SMARCD3, MAGE-A6, MED13, PAS5A WDR46, HELZ2, AFMID, CENPL, PRDX3, FLNA, KIF16B, SON, MTFR2 (D626Y), CHTF18 (L769V), MYADM (R30W), NUP98 (A359D), KRAS (G12D), CASP8 (F67V), TUBGCP2 (P293L), RNF213 (N1702S), SKIV2L (R653H), H3F3B (A48T), AP15 (R243Q), RNF10 (E572K), PHLPP1 (G566E) and ZFYVE27 (R6H). Non limiting examples of TAA recognized by CD4+ T cells may be ERBB2IP (E805G), CIRH1A (P333L), GART (V551A), ASAP1 (P941L), RND3 (P49S), LEMD2 (P495L), TNIK (S502F), RPS12 (V1041), ZC3H18 (G269R), GPD2 (E426K), PLEC (E1179K), XPO7 (P274S), AKAP2 (Q418K) and ITGB4 (S10021). Non-limiting examples of MHC class II-restricted antigens may be Tyrosinase, gp100, MART-1, MAGE-A1, MAGE-A2, MAGE-A3, MAGE-A6, LAGE-1, CAMEL, NY-ESO-1, hTRT and Eph.

Cancer antigen and tumor antigen are used interchangeably herein. The antigens may be related to cancers that include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenstrom; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sezary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrom macroglobulinemia and Wilms tumor (kidney cancer). In some particular embodiments, antibodies applicable in the methods, encoded by the cassettes and compositions of the invention may include but are not limited to the 3BNC117 antibody, an anti-TNFα antibody, specifically, the Adalimumab (Humira™) antibody, anti MUC1 glycoform antibody, specifically, the PankoMab-GEX. In some particular and non-limiting embodiments such specific antibodies may comprise the amino acid sequence as denoted by SEQ ID NOs. 13, 14 and 15 and 16, respectively or any homolog, variant or derivative thereof as disclosed herein before. Thus, in some embodiments, the cassettes provided by the invention and used by the methods and compositions described herein may comprise as an at least one nucleic acid sequence of interest, a nucleic acid sequence encoding the antibodies that comprise an amino acid sequence as denoted by any one of SEQ ID NOs. 13, 14 and 15 and 16.

In some particular embodiments, the nucleic acid cassette may comprise a nucleic acid sequence encoding a secreted antibody directed against and specific for an autoantigen and in addition, a BCR directed against and specific for a foreign antigen. In yet some further specific embodiments, the antibody and the BCR encoding sequences are separated by at least one of, IRES, a 2A peptide coding sequence and/or a promoter.

An "autoantigen" as used herein, refers to an endogenous antigen that despite being a normal tissue constituent, evokes an immune response by the host.

The term "foreign antigen" refers to any antigens and epitopes that are not naturally a part or a component of the subject but instead, may be in some embodiments a part of an organism or pathogen that infects the subject and causes a disease or disorder. Therefore, foreign antigens may be any infectious agent such as a bacterium, a prion, a parasitic agent, a eukaryotic unicellular or multicellular infectious agent, a fungus or a virus. The virus may be any virus, such as poliovirus, poxvirus, smallpox virus, herpes virus, retrovirus, HIV, measles virus, rubella virus, rhinovirus, yellow fever virus, dengue virus, hepatitis viruses A, B, or C, rabies virus, rhabdovirus or any other virus.

In the context of the invention, a foreign antigen may be used as a "foreign inducer" to induce secretion of an autoantibody. In some specific embodiments, as disclosed by the following examples, specifically Example 5, the targeting cassette of the invention may separately encode a secreted antibody directed against a disease associated autoantigen and a BCR directed against the foreign inducer. The targeted B cell differentiates to Antibody-secreting plasma cells only upon administration of the foreign inducer.

In some embodiments, the foreign inducer of BCR activation may be an antigen of a known vaccine. A prominent example may be the Polio vaccine, a safe, cheap, that is rarely encountered through the natural life course, thus diminishing the risk of spurious activation. There are two types of Polio vaccines: one that uses inactivated poliovirus and is given by injection (IPV), and one that uses weakened poliovirus which is orally administered (OPV). It should be appreciated that both types may be applicable in the present invention.

In yet some other specific embodiments applicable in the present invention, an autoantigen may be Her2 (=Neo=Erbb2) and the BCR may be Pertuzumab or Trastuzumab (with the added transmembrane domain from IgH).

In certain embodiments, the target genomic locus targeted by the method of the invention may be at least one of Immunoglobulin heavy chain locus, Immunoglobulin κ chain locus, Immunoglobulin λ chain locus, TCRβ chain locus, TCRα chain locus, TCRγ chain and the TCRδ chain locus. More specifically, in some embodiments, such target locus is a locus where a natural V(D)J recombination occurs naturally, specifically, V(D)J recombination mediated by RAG complex.

It should be noted that "target genomic locus" is the site of modification of an endogenous chromosomal locus by the insertion into, integration into, deletion of, or replacement of the endogenous sequence via V(D)J recombination using the cassette of the invention.

T cell receptors are composed of an alpha chain and a beta chain. More specifically, TCRβ chain locus, TCRα chain locus, TCRγ chain locus and the TCRδ chain locus refers to the chromosomal position of the TCRβ chain coding gene (on chromosome 7), of the TCRα chain coding gene (on chromosome 14), of the TCRγ chain coding gene (on chromosome 7) and of the TCRδ chain coding gene (on chromosome 14), respectively. The κ segments are on human chromosome 2 and the λ segments are on human chromosome 22. As noted herein before, the T cell receptor genes are similar to immunoglobulin genes since they contain multiple V, D and J gene segments in their beta chains (and V and J gene segments in their alpha chains) that are rearranged during the development of the lymphocyte to provide a unique antigen receptor. The TCR comprises 50 Vα, 50 Jα, 20 Vβ, 13 Jβ, 2 Dβ gene segments (100 α, 35 β), and a smaller number of γδ gene segments. Thus, the target genomic locus may be located at any of these specific segments. A typical antibody is composed of two immunoglobulin (Ig) heavy chains and two Ig light chains. In humans, antibodies are encoded by three independent gene loci, namely the immunoglobulin heavy locus (IgH) on chromosome 14, containing the gene segments for the immunoglobulin heavy chain, the immunoglobulin kappa (κ) locus (IgK) on chromosome 2, containing the gene segments for part of the immunoglobulin light chain and the immunoglobulin lambda (λ) locus (IgL) on chromosome 22, containing the gene segments for the immunoglobulin light chain.

The antibody and BCR heavy chains comprises 51 Variable (V) gene segments, 27 Diversity (D) gene segments, 6 Joining (J) gene segments. The antibody and BCR light chains comprises 40 Vκ, 31 Vλ, 5 Jκ, 4 Jλ gene segments.

In yet some further embodiments, the cassette provided by the methods of the invention may be comprised within a nucleic acid vector. In more specific embodiments, such vector may be any one of a viral vector, a non-viral vector and a naked DNA vector.

Vectors, as used herein, are nucleic acid molecules of particular sequence can be incorporated into a vector that is then introduced into a host cell, thereby producing a transformed host cell. A vector may include nucleic acid sequences that permit it to replicate in a host cell, such as an origin of replication. A vector may also include one or more selectable marker genes and other genetic elements known in the art, including promoter elements that direct nucleic acid expression. Many vectors, e.g. plasmids, cosmids, minicircles, phage, viruses, etc., useful for transferring nucleic acids into target cells may be applicable in the present invention. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as AAV, MMLV, HIV-1, ALV, etc.

Vectors may be provided directly to the subject cells. In other words, the cells are contacted with vectors comprising the cassettes of the invention that comprise the nucleic acid sequence of interest such that the vectors are taken up by the cells. Methods for contacting cells with nucleic acid vectors that are plasmids, such as electroporation, calcium chloride transfection, and lipofection, are well known in the art. DNA can be introduced as naked nucleic acid, as nucleic acid complexed with an agent such as a liposome or poloxamer, or can be delivered by viruses (e.g., adenovirus, AAV).

More specifically, in some embodiments, the vector may be a viral vector. In yet some particular embodiments, such viral vector may be any one of recombinant adeno associated vectors (rAAV), single stranded AAV (ssAAV), self-complementary rAAV (scAAV), Simian vacuolating virus 40 (SV40) vector, Adenovirus vector, helper-dependent Adenoviral vector, retroviral vector and lentiviral vector.

As indicated above, in some embodiments, viral vectors may be applicable in the present invention. The term "viral vector" refers to a replication competent or replication-deficient viral particle which are capable of transferring nucleic acid molecules into a host.

The term "virus" refers to any of the obligate intracellular parasites having no protein-synthesizing or energy-generating mechanism. The viral genome may be RNA or DNA contained with a coated structure of protein of a lipid membrane. Examples of viruses useful in the practice of the present invention include baculoviridiae, parvoviridiae, picornoviridiae, herepesviridiae, poxviridiae, adenoviridiae, picotmaviridiae. The term recombinant virus includes chimeric (or even multimeric) viruses, i.e. vectors constructed using complementary coding sequences from more than one viral subtype.

In some embodiments, the cassette of the invention may be comprised within an Adeno-associated virus (AAV). The term "adenovirus" is synonymous with the term "adenoviral vector". AAV is a single-stranded DNA virus with a small (~20 nm) protein capsule that belongs to the family of parvoviridae, and specifically refers to viruses of the genus adenoviridiae. The term adenoviridiae refers collectively to animal adenoviruses of the genus mastadenovirus including but not limited to human, bovine, ovine, equine, canine, porcine, murine and simian adenovirus subgenera. In particular, human adenoviruses includes the A-F subgenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad IIP), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91.

Due to its inability to replicate in the absence of helper-virus coinfections (typically Adenovirus or Herpesvirus infections) AAV is often referred to as dependovirus. AAV infections produce only mild immune responses and are considered to be nonpathogenic, a fact that is also reflected by lowered biosafety level requirements for the work with recombinant AAVs (rAAV) compared to other popular viral vector systems. Due to its low immunogenicity and the absence of cytotoxic responses AAV-based expression systems offer the possibility to express genes of interest for months in quiescent cells.

Production systems for rAAV vectors typically consist of a DNA-based vector containing a transgene expression cassette, which is flanked by inverted terminal repeats. Construct sizes are limited to approximately 4.7-5.0 kb, which corresponds to the length of the wild-type AAV genome. rAAVs are produced in cell lines. The expression vector is cotransfected with a helper plasmid that mediates expression of the AAV rep genes which are important for virus replication and cap genes that encode the proteins forming the capsid. Recombinant adeno-associated viral vectors can transduce dividing and non-dividing cells, and different rAAV serotypes may transduce diverse cell types. These single-stranded DNA viral vectors have high transduction rates and have a unique property of stimulating endogenous Homologous Recombination without causing double strand DNA breaks in the host genome.

It should be appreciated that many intermediate steps of the wild-type infection cycle of AAV depend on specific interactions of the capsid proteins with the infected cell. These interactions are crucial determinants of efficient transduction and expression of genes of interest when rAAV is used as gene delivery tool. Indeed, significant differences in transduction efficacy of various serotypes for particular tissues and cell types have been described. Thus, in some embodiments AAV serotype 6 may be suitable for the methods of the invention. In yet some further embodiments, AAV serotype 8 may be suitable for the methods of the invention. In some embodiments, the AAV serotype 6 may be encoded by the nucleic acid sequence as denoted by GenBank accession number AF028704.1. In some specific embodiments, the AAV serotype 6 may be encoded by the nucleic acids sequence as denoted by SEQ ID NO: 29. In some embodiments, the AAV serotype 8 may be encoded by the nucleic acid sequence as denoted by GenBank accession number NC_006261.1. In some specific embodiments, the AAV serotype 8 may be encoded by the nucleic acids sequence as denoted by SEQ ID NO: 30.

It is believed that a rate-limiting step for the AAV-mediated expression of transgenes is the formation of double-stranded DNA. Recent reports demonstrated the usage of rAAV constructs with a self-complementing structure (scAAV) in which the two halves of the single-stranded AAV genome can form an intra-molecular double-strand. This approach reduces the effective genome size usable for gene delivery to about 2.3 kB, but leads to significantly shortened onsets of expression in comparison with conventional single-stranded AAV expression constructs (SSAAV). Thus, in some embodiments, ssAAV may be applicable as a viral vector by the methods of the invention.

In yet some further embodiments, HDAd vectors may be suitable for the methods of the invention. The Helper-Dependent Adenoviral (HDAd) vectors HDAds have innovative features including the complete absence of viral coding sequences and the ability to mediate high level transgene expression with negligible chronic toxicity. HDAds are constructed by removing all viral sequences from the adenoviral vector genome except the packaging sequence and inverted terminal repeats, thereby eliminating the issue of residual viral gene expression associated with early generation adenoviral vectors. HDAds can mediate high efficiency transduction, do not integrate in the host genome, and have a large cloning capacity of up to 37 kb, which allows for the delivery of multiple transgenes or entire genomic loci, or large cis-acting elements to enhance or regulate tissue-specific transgene expression. One of the most attractive features of HDAd vectors is the long term expression of the transgene.

Still further, in some embodiments, SV40 may be used as a suitable vector by the methods of the invention. SV40 vectors (SV40) are vectors originating from modifications brought to Simian virus-40 an icosahedral papovavirus. Recombinant SV40 vectors are good candidates for gene transfer, as they display some unique features: SV40 is a well-known virus, non-replicative vectors are easy-to-make, and can be produced in titers of 10(12) IU/ml. They also efficiently transduce both resting and dividing cells, deliver persistent transgene expression to a wide range of cell types, and are non-immunogenic. Present disadvantages of rSV40 vectors for gene therapy are a small cloning capacity and the possible risks related to random integration of the viral genome into the host genome.

In certain embodiments, an appropriate vector that may be used by the invention may be a retroviral vector. A retroviral vector consists of proviral sequences that can accommodate the gene of interest, to allow incorporation of both into the target cells. The vector may also contain viral and cellular gene promoters, to enhance expression of the gene of interest in the target cells.

Retroviral vectors stably integrate into the dividing target cell genome so that the introduced gene is passed on and expressed in all daughter cells. They contain a reverse transcriptase that allows integration into the host genome.

In yet some alternative embodiments, lentiviral vectors may be used in the present invention. Lentiviral vectors are derived from lentiviruses which are a subclass of Retroviruses. Commonly used retroviral vectors are "defective", i.e. unable to produce viral proteins required for productive infection. Rather, replication of the vector requires growth in a packaging cell line. To generate viral particles comprising the cassette with the nucleic acids sequence of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the cassette of the invention that contains the nucleic acids sequence of interest into packaging cell lines and of collecting the viral particles that are generated by the packaging lines are well known in the art.

In some alternative embodiments, the vector may be a non-viral vector. More specifically, such vector may be in some embodiments any one of plasmid, minicircle and linear DNA.

Nonviral vectors, in accordance with the invention, refer to all the physical and chemical systems except viral systems and generally include either chemical methods, such as cationic liposomes and polymers, or physical methods, such as gene gun, electroporation, particle bombardment, ultrasound utilization, and magnetofection. Efficiency of this system is less than viral systems in gene transduction, but their cost-effectiveness, availability, and more importantly reduced induction of immune system and no limitation in size of transgenic DNA compared with viral system have made them attractive also for gene delivery.

For example, physical methods applied for in vitro and in vivo gene delivery are based on making transient penetration in cell membrane by mechanical, electrical, ultrasonic, hydrodynamic, or laser-based energy so that DNA entrance into the targeted cells is facilitated.

In more specific embodiments, the vector may be a naked DNA vector. More specifically, such vector may be for example, a plasmid, minicircle or linear DNA.

Naked DNA alone may facilitate transfer of a gene (2-19 kb) into skin, thymus, cardiac muscle, and especially skeletal muscle and liver cells when directly injected. It enables also long-term expression. Although naked DNA injection is a safe and simple method, its efficiency for gene delivery is quite low.

Minicircles are modified plasmid in which a bacterial origin of replication (ori) was removed, and therefore they cannot replicate in bacteria.

Linear DNA or Doggybone™ are double-stranded, linear DNA construct that solely encodes an antigen expression cassette, comprising antigen, promoter, poly A tail and telomeric ends.

It should be appreciated that all DNA vectors disclosed herein, may be also applicable in the methods, cassettes and compositions of the invention.

Still further, it must be appreciated that the invention further provides any vectors or vehicles that comprise any of the nucleic acid cassettes disclosed by the invention, as well as any host cell expressing the nucleic acid cassettes disclosed by the invention.

In some specific embodiments, the cassette of the invention introduces the nucleic acid of interest in a target locus of a mammalian cell that is considered herein as a host cell. The term "host cell" includes a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell". It should be noted that the host cell of the invention express at least one of RAG proteins.

In yet some further embodiments, the method of the invention is directed at targeted insertion of a nucleic acid sequence of interest in a target locus of a mammalian cell. In some specific embodiments, the mammalian cells may be any one of a naturally RAG expressing cell, stably RAG expressing cell, inducibly RAG expressing cell and a cell transfected with RAG expression vector/s. It should be noted that RAG expressing cells in some embodiments may be cells that actively undergo RAG mediated VDJ recombination. However, it should be understood that "RAG expressing cells" targeted by the methods of the invention may also encompass in some embodiments cells that have already underwent VDJ recombination but still express RAG. More specifically, in some embodiments, such cells no longer undergo VDJ recombination at the V locus, but are still permissive for VDJ targeting at their D and J loci. In some embodiments, such integration may allow expression if the transgene is preceded by at least one of a promoter of any fragments thereof (e.g., a minimal promoter) and/or a splice acceptor.

In more specific embodiments, the target cell may be an immune cell, specifically hematopoietic cell. In yet some further specific embodiments, such hematopoietic cell may be of the lymphoid lineage, specifically, a lymphocyte. "Lymphocytes" are mononuclear nonphagocytic leukocytes found in the blood, lymph, and lymphoid tissues. They are divided on the basis of ontogeny and function into two classes, B and T lymphocytes, responsible for humoral and cellular immunity, respectively. Most are small lymphocytes 7-10 μm in diameter with a round or slightly indented heterochromatic nucleus that almost fills the entire cell and a thin rim of basophilic cytoplasm that contains few granules. When "activated" by contact with antigen, small lymphocytes begin macromolecular synthesis, the cytoplasm enlarges until the cells are 10-30 μm in diameter, and the nucleus becomes less completely heterochromatic; they are then referred to as large lymphocytes or lymphoblasts. These cells then proliferate and differentiate into B and T memory cells and into the various effector cell types: B cells into plasma cells and T cells into helper, cytotoxic, and suppressor cells. In yet more specific embodiments, such cell may be any one of a lymphocyte progenitor, ex vivo differentiating lymphocytes, hematopoietic stem and progenitor cells (HSPCs) and Induced pluripotent stem cells (iPSCs).

It should be appreciated that in some embodiments, the target cells may be pluripotent cells, specifically, hematopoietic pluripotent cells. The term "pluripotent" refers to cells with the ability to give rise to progeny that can undergo differentiation, under the appropriate conditions, into cell types that collectively demonstrate characteristics associated with different cell lineages.

In more specific embodiments, cells suitable in the present invention may be iPSCs. As used herein, "induced pluripotent stem cells" or "iPSCs" refers to a type of pluripotent stem cell artificially derived from a non-pluripotent cell, typically an adult somatic cell, by inducing a "forced" expression of certain genes.

Still further, in some embodiments, cells suitable in the present application may be immobilized HSP. Hematopoietic stem cells (HSCs) normally reside in the bone marrow but can be forced into the blood, a process termed bone marrow mobilization used to harvest large numbers of HSCs in peripheral blood. One mobilizing agent of choice in accordance with the invention may be granulocyte colony-stimulating factor (G-CSF). The resulting HSCs are further referred as mobilized HSCs.

More specifically, hematopoietic stem cells (HSCs) originate from the bone marrow. They first differentiate into multipotent progenitor (MPP) cells, and then may differentiate to common lymphoid progenitor (CLP) cells.

A "committed lymphoid progenitor cell" refers to an oligopotent or unipotent progenitor cell capable of differentiating into any of the terminally differentiated cells of the lymphoid lineage, such as T cell, B cell, NK cell, or lymphoid dendritic cells. Different cell populations of lymphoid progenitors are distinguishable from other cells by their differentiation potential, and the presence of a characteristic set of cell markers. Encompassed within the lymphoid progenitor cells are the "common lymphoid progenitor cells (CLP)", which are oligopotent cells characterized by a capacity to give rise to B-cell progenitors (BCP), T-cell progenitors (TCP), NK cell progenitors, and dendritic cells. These progenitor cells have little or no self-renewing capacity, but are capable of giving rise to T lymphocytes, B lymphocytes, NK cells, and lymphoid dendritic cells.

More specifically, in some embodiments, the lymphocyte progenitor may be any one of a T cell progenitor, a B cell progenitor and an NK cell progenitor.

A "T cell" or "T lymphocyte" as used herein is characterized by the presence of a T-cell receptor (TCR) on the cell surface. It should be noted that T-cells include helper T cells ("effector T cells" or "Th cells"), cytotoxic T cells ("Tc," "CTL" or "killer T cell"), memory T cells, and regulatory T cells as well as Natural killer T cells, Mucosal associated invariants and Gamma delta T cells.

More specifically, Thymocytes are hematopoietic progenitor cells present in the thymus. Thymopoiesis is the process in the thymus by which thymocytes differentiate into mature T lymphocytes. The thymus provides an inductive environment, which allows for the development and selection of physiologically useful T cells. The processes of beta-selection, positive selection, and negative selection shape the population of thymocytes into a peripheral pool of T cells that are able to respond to foreign pathogens and are immunologically tolerant towards self-antigens.

Thymocytes are classified into a number of distinct maturational stages based on the expression of cell surface markers. The earliest thymocyte stage is the double negative (DN) stage (negative for both CD4 and CD8), which more recently has been better described as Lineage-negative, and which can be divided into four sub-stages. The next major stage is the double positive (DP) stage (positive for both CD4 and CD8). The final stage in maturation is the single positive (SP) stage (positive for either CD4 or CD8).

More specifically, the maturational stages of thymocytes may include the following substages: Double negative 1 (DN1) or ETP (Early T lineage Progenitor) is characterized by CD44+CD25−CD117+ defining surface markers, thymocytes are located in the cortex and proliferation, loss of B and myeloid potentials are observed; Double negative 2 (DN2) is characterized by CD44+CD25+CD117+ defining surface markers and thymocytes are located in the cortex; Double negative 3 (DN3) is characterized by CD44−CD25+ defining surface markers, thymocytes are located in the cortex and TCR-beta rearrangement and beta selection are observed; Double negative 4 (DN4) is characterized by CD44−CD25− defining surface markers and thymocytes are located in the cortex; Double positive is characterized by CD4+CD8+ defining surface markers, thymocytes are located in the cortex and TCR-alpha rearrangement, positive selection, negative selection are observed; Single positive is characterized by CD4+CD8− or CD4−CD8+ defining surface markers, thymocytes are located in the medulla and Negative selection is observed.

In human, circulating CD34+ hematopoietic stem cells (HSC) reside in bone marrow. They produce precursors of T lymphocytes, which seed the thymus (thus becoming thymocytes) and differentiate under influence of the Notch and its ligands. Early, double negative thymocytes express (and can be identified by) CD2, CD5 and CD7. Still during the double negative stage, CD34 expression stops and CD1 is expressed. Expression of both CD4 and CD8 makes them double positive, and matures into either CD4+ or CD8+ cells.

Still further, in some embodiments, the hematopoietic cell applicable in the methods and compositions of the invention may be a B cell progenitor. B cells develop from HSCs that originate from bone marrow. Their development into B cells occurs in several stages, each marked by various gene expression patterns and immunoglobulin H chain and L chain gene loci arrangements, the latter due to B cells undergoing V(D)J recombination as they develop.

To ensure proper development, B cells undergo two types of selection while developing in the bone marrow. Positive selection occurs through antigen-independent signaling involving both the pre-BCR and the BCR. If these receptors do not bind to their ligand, B cells do not receive the proper signals and cease to develop. Negative selection occurs through the binding of self-antigen with the BCR; if the BCR can bind strongly to self-antigen, then the B cell undergoes one of four fates: clonal deletion, receptor editing, anergy, or ignorance (B cell ignores signal and continues development). This negative selection process leads to a state of central tolerance, in which the mature B cells does not bind with self-antigens present in the bone marrow.

To complete development, immature B cells migrate from the bone marrow to the spleen as well as pass through two transitional stages: T1 and T2. Throughout their migration to the spleen and after spleen entry, they are considered T1 B cells. Within the spleen, T1 B cells transition to T2 B cells. T2 B cells differentiate into either follicular (FO) B cells or marginal zone (MZ) B cells depending on signals received through the BCR and other receptors. Once differentiated, they are now considered mature B cells, or naive B cells.

While immature and during the T1 phase, B cells express BCR of class IgH, but BCR expression changes to the classes IgM and IgD after transition into the T2 phase and while mature up to activation.

It should be appreciated that in some specific embodiments, the targeted insertion of at least one nucleic acid sequence of interest into a target genomic locus in a target cell may be performed by the method of the invention in a mammalian subject. It is to be understood that the invention therefore provides in some aspects thereof any host cell transfected, transformed or transduced by any of the vectors or vehicles of the invention that comprise any of the nucleic acid cassettes disclosed herein. Such cell may be any of the cells, specifically the hematopoietic cells disclosed by the invention.

In a second aspect, the invention relates to a method for targeted insertion of at least one nucleic acid sequence of interest into a target genomic locus of a cell in a mammalian subject. More specifically, the method may comprise the step of administering to the subject an effective amount of at least one nucleic acid cassette comprising the nucleic acid sequence of interest and at least one RSS. Alternatively, a vector comprising the cassette of the invention may be administered to the subject. It should be noted that the nucleic acid cassette administered by the method of the invention enables the insertion of a nucleic acid sequence of interest into a target genomic locus. More specifically, such insertion may be facilitated, mediated and/or performed by RAG-catalyzed recombination between at least one genomic RSS flanking the target genomic locus and at least one RSS comprised within the nucleic acid cassette.

In some specific embodiments the nucleic acid cassette may be flanked on both the 5' and 3' ends thereof by RSS.

In more specific embodiments, the RSS comprised within the cassette administered by the method of the invention may be at least one of 12 RSS, 23 RSS and 22 RSS. In some particular and non-limiting embodiments, RSS applicable in the present invention may by any of the RSSs as denoted by nucleic acid sequence of SEQ ID NO. 36, 37, 38, 39, 40 and 41.

In some embodiments, the RSS used by the methods and cassettes of the invention may be naturally occurring, selected by a screen, rationally optimized, selected based on compatibility or incompatibility with other RSSs.

In yet some further specific embodiments, the nucleic acid cassette administered by the method of the invention may further comprise at least one genetic element, said genetic element is at least one of: an IRES, a 2A peptide coding sequence, a promoter or any functional fragment thereof, a splice donor, a splice acceptor, a degron, a 3 frame stop, a protein stabilizing sequence, a signal peptide, a stop codon, a polyadenylation site, a transcription enhancer, a switch region, an mRNA stabilizing sequence and a protein stabilizing sequence.

In some specific embodiments, the cassette administered by the method of the invention may comprise two or more nucleic acid sequences of interest separated by at least one genetic element. In more specific embodiments, such genetic element may be at least one of an IRES, a 2A peptide coding sequence and a promoter.

In certain embodiments, the nucleic acid sequence of interest comprised within the cassette administered by the method of the invention may be a protein coding nucleic acid sequence or a non-coding sequence.

In some specific embodiments, where the nucleic acid sequence of interest is a protein coding gene, such protein may be at least one of: a therapeutic protein or peptide, a prophylactic protein, a tolerizing protein, an immunizing protein, a toxic protein, an inducible suicide protein, a marker protein, an imaging protein and a fusion or chimeric protein.

In yet some further alternative embodiments, the nucleic acid sequence of interest may encode at least one small non-coding RNA molecule. More specifically, such one small non-coding RNA molecule may be for example, miRNA, siRNA, shRNA or any of the one small non-coding RNA molecules described by the invention herein before. In some further embodiments, the small non-coding RNA molecule may be specifically directed against a TCR chain, a BCR chain, an immune checkpoint gene or an apoptotic gene.

In more specific embodiments, the nucleic acid sequence of interest of the cassette administered by the method of the invention may encode at least one of a receptor and an antibody or any fragment/s or chimera/s thereof.

In some particular embodiments, the nucleic acid sequence of interest may encode at least one receptor. More specifically, such receptor may be any one of: a TCR, CAR and a BCR.

In some embodiments, the nucleic acid sequence of interest may encode a receptor that may be a naturally occurring receptor, receptor selected by a screen or rationally designed receptor.

In yet some further particular embodiments, the nucleic acid sequence of interest may encode at least one antibody. More specifically, such antibody may be any one of full length antibody, antibody fragment, scFv, bi-specific antibody, tri-specific antibody, BiTE and V-NAR.

In some embodiments, the nucleic acid sequence of interest may encode an antibody that may be a naturally occurring antibody, antibody or fragments thereof selected by a screen or rationally designed antibody.

In some embodiments, the nucleic acid cassette administered by the method of the invention may comprise a nucleic acid sequence encoding a secreted antibody directed against and specific for an autoantigen. This cassette may further comprise a nucleic acid sequence encoding a BCR directed against and specific for a foreign antigen. It should be noted that in certain embodiments, these two nucleic acid sequences are separated by at least one genetic element, for example, an IRES, a 2A peptide coding sequence and a promoter.

In certain embodiments, the target genomic locus for the targeted insertion of the nucleic acid sequence of interest comprised within the cassette administered by the method of the invention may be at least one of Immunoglobulin heavy chain locus, Immunoglobulin κ chain locus, Immunoglobulin λ chain locus, TCRβ chain locus, TCRα chain locus, TCRγ chain and the TCRδ chain locus.

It should be appreciated that in certain embodiments, the nucleic acid cassette administered by the method of the invention may be comprised within a nucleic acid vector. More specifically, such vector may be any one of a viral vector, a non-viral vector and a naked DNA vector.

In more specific embodiments, the vector may be a viral vector. Specifically, suitable viral vectors may be any one of rAAV, ssAAV, scAAV, SV40 vector, Adeno virus vector, helper-dependent Adeno viral vector, retroviral vector and lentiviral vector.

In yet some further embodiments, the cassette administered by the method of the invention may be comprised within a non-viral vector. Such vector may be any one of plasmid, minicircle and linear DNA. In yet some further embodiments, the vector may be a naked DNA vector, specifically, any one of plasmid, minicircle and linear DNA.

It should be noted that in certain embodiments, the cassette administered by the method of the invention to a subject, leads to targeted insertion of the nucleic acid sequence of interest into a target locus in a cell of said mammalian subject. It should be noted that the targeted insertion may be mediated and facilitated by RAG complex. Thus, in some specific embodiments, the targeted cell/s of the subject may naturally express RAG. However, it should be noted that the invention further encompasses in some embodiments thereof, the option that the target cells of the administered subject may be either stably RAG expressing or inducibly RAG expressing. Such cells in some embodiments may be transfected with RAG expression vectors. As indicated herein before, in some embodiments, RAG expressing cells may be cells that undergo VDJ recombination. In yet some further embodiments, RAG expressing cell may further encompass cells that already underwent VDJ recombination but still express RAG.

In certain embodiments, the cell/s of the administered subject targeted by the cassette of the invention may be any one of thymocytes, HSPCs and mobilized HSPCs.

In yet some specific embodiments, the cells targeted by the cassette administered by the method of the invention may be thymocytes of any subsect. More specifically, such cells may be thymocytes of any one of the DN1, DN2, DN3, DN4, DP and SP subsets, as described herein above. In yet some further embodiments, the cells targeted by the cassette administered to the subject by the method of the invention may be splenocytes of any subsect, or any lymphocytes obtained or present in lymph nodes and bone marrow.

The subject methods and compositions may be applied to any disease, disorder, or natural cellular process that would benefit from modulating cell activity by integrating a gene of interest.

In some specific embodiments, the subject administered by the method of the invention may be a subject in need. In more particular and non-limiting embodiments, such subject may be a subject suffering of an immune-related disorder.

It should be further appreciated that the method of the invention also encompasses the option that the targeted insertion of the nucleic acid sequence of interest to cells of the subject may be performed ex vivo, to cells of the subjects (cells of autologous source) or alternatively, to cells of allogeneic source. These cells may be than administered to the subject by adoptive transfer. The term "adoptive transfer" as herein defined applies to all the therapies that consist of the transfer of components of the immune system, specifically cells that are already capable of mounting a specific immune response. Examples of adoptive transfer include both the transfer of antibodies and also, in adoptive cell transfer, specific types of cells that are capable of mediating antigen-specific tumor regression such as T cells.

A further aspect of the invention relates to a method for treating, preventing, ameliorating, inhibiting or delaying the onset of a pathologic disorder in a mammalian subject. More specifically, the method of the invention may comprise the step of administering to the treated subject an effective amount of at least one of: (a) nucleic acid cassette for targeted insertion of at least one nucleic acid sequence of interest into a target genomic locus; (b) a vector comprising said nucleic acid cassette; and (c) a cell transduced or transfected with the nucleic acid cassette, or any combinations thereof. It should be noted that the cassette administered by the method of the invention may comprise at least one nucleic acid sequence of interest and at least one RSS. It should be understood that in some embodiments, the insertion of the nucleic acid sequence of interest into the target genomic locus in cell/s of the treated subject may be facilitated, mediated and/or performed by RAG-catalyzed recombination between at least one genomic RSS flanking the target genomic locus and at least one RSS comprised within the nucleic acid cassette.

Thus, the invention provides therapeutic and prophylactic methods that are based on targeted insertion of a nucleic acid sequence of interest into a specific locus in cells of a subject in need. It should be appreciated that the methods of the invention enable whether in vivo insertion of the nucleic acid sequence of interest into cells of the treated subjects, by administering to the treated subject the nucleic acid cassette, or a vector comprising said cassette. In some alternative embodiments, the insertion of at least one nucleic acid sequence of interest into a specific locus in cells of the subject, may be performed ex vivo. In such option, the targeted insertion of the nucleic acid sequence of interest is performed in cells of an autologous or allogeneic source, that are then administered to the subject, specifically, by adoptive transfer.

In some embodiments, the subject treated by the method of the invention undergoes or may be subjected to a preceding treatment. In some specific embodiments, such preceding treatment may be at least one of HSPC mobilization, immune ablation and steroid administration.

In some embodiments, the treated patient treated by the method of the invention may be subjected to preceding treatment. In some embodiments, such treatment may be bone marrow mobilization. Bone marrow mobilization of progenitor cells is a multistage process, with initial release from their bone marrow niche followed by active migration across the bone marrow sinusoidal endothelium. The chemokine axis SDF-1α/CXCR4 is critically involved in the retention of hematopoietic stem cells within the bone marrow. At a molecular level, G-CSF acts by disrupting the SDF-1α/CXCR4 retention axis, both by reducing CXCR4 expression on HPCs and levels of SDF-1α in the bone marrow.

CXCR4 antagonists are also used as HPC-mobilizing agents, for example AMD3100, and may be applicable in the present invention.

In yet some further embodiments, the patient treated by the method of the invention may be subjected to preceding treatment that may involve immunoabalation. Treatment of some types of medical conditions, such as cancers, autoimmune diseases and the like often involves an immunoablation to remove the patient's own immune system, for example, prior to transplant of a bone marrow or other tissue graft. Immunoablation can be accomplished by total body radiation or by high dose chemotherapy. Therefore, the term "immune ablation" or "immunoablation" refers to the destruction of a patient immune resistance for a medical purpose.

Still further, in some embodiments, the patient treated by the method of the invention may be subjected to preceding treatment with steroids. In some embodiments, such treatment may be Steroid administration may be also used to inhibit the immune response. In pharmacologic (supraphysiologic) doses, steroids such as glucocorticoids are used to suppress various allergic, inflammatory, and autoimmune disorders.

In some specific embodiments, the nucleic acid cassette administered to the treated subject, may be flanked on both the 5' and 3' ends thereof by RSS.

In more specific embodiments, such RSS may be at least one of 12 RSS, 23 RSS and 22 RSS. In some particular and non-limiting embodiments, RSS applicable in the present invention may by any of the RSSs as denoted by nucleic acid sequence of SEQ ID NO. 36, 37, 38, 39, 40 and 41.

In one embodiments, the RSS used by the methods and cassettes of the invention may be naturally occurring, selected by a screen, rationally optimized, selected based on compatibility or incompatibility with other RSSs.

In yet some further embodiments, the cassette administered by the method of the invention may further comprise at least one genetic element. More specifically, in so embodiments, the genetic element may be at least one of: an IRES, a 2A peptide coding sequence, a promoter or any functional fragments thereof (e.g., a minimal promoter), a splice donor, a splice acceptor, a degron, a 3 frame stop, a protein stabilizing sequence, a signal peptide, a stop codon, a polyadenylation site, a transcription enhancer, a switch region, an mRNA stabilizing sequence and a protein stabilizing sequence.

In some particular embodiments, the cassette may comprise two or more nucleic acid sequences of interest separated by at least one genetic element, said genetic element may be at least one of: an IRES, a 2A peptide coding sequence and a promoter.

It should be noted that the nucleic acid sequence of interest inserted into a specific locus by the method of the invention may be a protein coding nucleic acid sequence or a non-coding sequence.

In some specific embodiments, such nucleic acid sequence of interest may be a protein coding nucleic acid sequence. More specifically, such gene may encode at least one of: a therapeutic protein or peptide, a prophylactic protein, a tolerizing protein, an immunizing protein, a toxic protein, an inducible suicide protein, a marker protein, an imaging protein and a fusion or chimeric protein. It should be understood that any of the proteins encoded by the nucleic acid sequence of interest described herein before in connection with other aspects of the invention are applicable for this aspect as well.

In yet some alternative or additional embodiments, the nucleic acid sequence of interest may encode at least one small non-coding RNA molecule, for example, miRNA, siRNA, shRNA and the like. In yet some further embodiments, the small non-coding RNA molecule may be specifically directed against a TCR chain, a BCR chain, an immune checkpoint gene, an apoptotic gene.

In certain embodiments, the nucleic acid sequence of interest may encode at least one of a receptor and an antibody or any fragment/s or chimera/s thereof. In more specific embodiments, the nucleic acid sequence of interest may encode at least one receptor, specifically, a TCR, CAR and a BCR or any combination thereof. In some embodiments, the nucleic acid sequence of interest may encode a receptor that may be a naturally occurring receptor, receptor selected by a screen or rationally designed receptor.

In yet some further embodiments, the nucleic acid sequence of interest may encode at least one antibody. More specifically, such antibody may be any one of full length antibody, antibody fragment, scFv, bi-specific antibody, tri-specific antibody, BiTE and V-NAR.

In some embodiments, the nucleic acid sequence of interest may encode an antibody that may be a naturally occurring antibody, antibody or fragments thereof selected by a screen or rationally designed antibody.

Still further, in some particular embodiments, the invention provides a method for engineering of inducible B-cells. More specifically, the nucleic acid cassette administered to the treated subject by the methods of the invention may comprise a nucleic acid sequence encoding a secreted antibody directed against and specific for an autoantigen and additionally, a nucleic acid sequence encoding a BCR directed against and specific for a foreign antigen. It should be noted that both nucleic acid sequences may be separated by at least one genetic element, for example, an IRES or a 2A peptide coding sequence. In certain embodiments, the method further comprises the step of administration of an effective amount of the foreign antigen (e.g., Polio vaccine for inducing B cell differentiation to plasma cells secreting Abs specific for the autoantigen) to the treated subject thereby inducing differentiation of the B cells into antibody secreting plasma cells.

In certain embodiments, the target genomic locus targeted by the cassette administered by the method of the invention may be at least one of Immunoglobulin heavy chain locus, Immunoglobulin κ chain locus, Immunoglobulin λ chain locus, TCRβ chain locus, TCRα chain locus, TCRγ chain and the TCRδ chain locus.

In some specific embodiments, for in vivo targeted insertion of the nucleic acid sequence of interest, the subject may be administered with a nucleic acid vector comprising the cassette. In more specific embodiments, such vector may be any one of a viral vector, a non-viral vector and a naked DNA vector.

In more specific embodiments, either for in vivo or for ex vivo targeted insertion, a viral vector may be used. In yet more specific embodiments, such viral vector may be any one of rAAV, ssAAV, scAAV, SV40 vector, Adeno virus vector, helper-dependent Adeno viral vector, retroviral vector and lentiviral vector.

In yet some alternative embodiments, the vector used by the method of the invention may be a non-viral vector, specifically, any one of plasmid, minicircle and linear DNA.

In yet some further embodiments, an appropriate vector for the method of the invention may be naked DNA vector, specifically, any one of plasmid, minicircle and linear DNA.

Still further, in some embodiments for in vivo targeted insertion of the nucleic acid sequence of interest, the nucleic acid cassette or any vector comprising the same used by the method of the invention, may be administered by at least one of systemic injection, intrathymic injection, bone marrow injection splenic injection and injection to lymph nodes.

More specifically, in some embodiments where engineered T cells are desired, the method of the invention intrathymic injection. Intrathymic injection is a procedure used in several T cell-associated immunological contexts to deliver cells or other substances directly into the thymus. In the context of the present invention, the nucleic acid cassette of the invention or any vector or composition thereof may be injected into the thymus, thereby specifically targeting differentiating T cells. In some embodiments, the nucleic acid cassette or the vector may be injected via intrathymic injection, in such case the target cells may be thymocytes, specifically, thymocytes of the DN1, DN2, DN3, DN4, DP and SP subsets).

In case of bone marrow injection, the target cells may be HSPCs and in case of systemic injection, the target cells may be mobilized HSPCs (where the patient is subjected to a preceding treatment of immobilization). It should be noted that both, the bone marrow injection as well as systemic injection (e.g., intravenous IV), may be specifically suitable for targeting B cells by the nucleic acid cassette of the invention. It is to be understood that other localized injection are also suitable, for example intra-lymph node injection or intra-spleen injection, and may be used to deliver a vector to the lymph node and the spleen, respectively. More specifically, in some embodiments, the subcutaneous route (SC) may be generally considered to be most appropriate for targeting to the lymph nodes. Conventional SC formulations are such as Aqueous solutions, Oily solutions, Suspensions and Simple emulsions. Specific technologies associated with SC delivery are via Modified release SC formulations such as Biodegradable in situ implants, Biodegradable microspheres, Osmotically controlled implants, Liposomes, Lipid nanoparticles. Relevant commercially available products may include but are not limited to Alzamer® Depot™, DUROS®, Stealth1 (ALZA Corporation), Atrigel® (Atrix Laboratories), SABER® (Durect Corp), ProLease (Alkermes Inc), DepoFoam® (SkyePharma Inc), SupraVail™ (Phares Drug Delivery AG).

In some embodiments, the nucleic acid sequence of interest may be inserted into a target genomic locus in cells of the treated subject that are RAG expressing, either naturally or stably RAG expressing, inducibly RAG expressing and transfected with RAG expression vectors. In some embodiments, RAG expressing cells may be cells that undergo VDJ recombination. However, it should be understood that this term may further encompasses cells that already underwent VDJ recombination but still display RAG expression.

In yet some further embodiments, where the targeted insertion of the nucleic acid sequence of interest is performed ex vivo, the treated subject may be administered with at least one cell transduced or transfected with the nucleic acid cassette.

In yet some specific embodiments, administration of the cells transfected or transformed by the nucleic acid cassette of the invention may be performed by adoptive transfer or implantation. In yet some further embodiments, the cassette may be introduced to the target cells by transfection, electroporation or in case of viral vectors, by transduction. Any suitable method known to the skilled artisan may be applicable herein.

As noted above, in more specific embodiments, the cell administered by the method of the invention may be any one of a lymphocyte progenitor, ex vivo differentiating lymphocytes, HSPCs and iPSCs.

Still further, in some embodiments, the cells may be of an autologous or allogeneic source.

In some embodiments, the cells transduced or transfected with the nucleic acid cassette provided by the invention may be cells of an autologous source. The term "autologous" when relating to the source of cells, refers to cells derived or transferred from the same subject that is to be treated by the method of the invention.

In yet some further embodiments, the cells transduced or transfected with the nucleic acid cassette used by the methods of the invention may be cells of an allogenic source.

The term "allogenic" when relating to the source of cells, refers to cells derived or transferred from a different subject, referred to herein as a donor, of the same species.

It should be noted that in certain embodiments, where adoptive transfer of cells (either of autologous or allogeneic source) that comprise the cassette of the invention is applied, the method of the invention may further comprise the preceding step of immunoabalation of the subject, as described herein before.

The methods of the invention may be in some embodiments thereof, specifically suitable for disorders associated with the immune system.

Thus, in some specific embodiments, the subject treated by the method of the invention may be a subject suffering of an immune-related disorder. An "Immune-related disorder" or "Immune-mediated disorder", as used herein encompasses any condition that is associated with the immune system of a subject, more specifically through inhibition of the immune system, or that can be treated, prevented or ameliorated by reducing degradation of a certain component of the immune response in a subject, such as the adaptive or innate immune response. An immune-related disorder may include infectious condition (e.g., viral, bacterial or fungal infections), inflammatory disease, autoimmune disorders, metabolic disorders and a proliferative disorders, specifically, cancer. In some specific embodiments wherein the immune-related disorder or condition may be a primary or a secondary immunodeficiency.

In some specific embodiments, the methods of the invention may be used for treating proliferative disorders. As used herein to describe the present invention, "proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods of the present invention may be applicable for treatment of a patient suffering from any one of non-solid and solid tumors.

Malignancy, as contemplated in the present invention may be any one of carcinomas, melanomas, lymphomas, leukemias, myeloma and sarcomas.

Carcinoma as used herein, refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges.

Melanoma as used herein, is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Further malignancies that may find utility in the present invention can comprise but are not limited to hematological malignancies (including lymphoma, leukemia and myeloproliferative disorders, as described above), hypoplastic and aplastic anemia (both virally induced and idiopathic), myelodysplastic syndromes, all types of paraneoplastic syndromes (both immune mediated and idiopathic) and solid tumors (including GI tract, colon, lung, liver, breast, prostate, pancreas and Kaposi's sarcoma. The invention may be applicable as well for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma. It should be appreciated that for treating cancer, the cassette of the invention or any compositions or methods thereof may facilitate V(D)J targeted insertion or antibody or receptor as described herein before, that are specifically directed at TAAs. It should be understood that the invention thus encompasses the treatment of any of the malignancies described in this context, specifically any malignancies described in connection with associated TAAs as described herein before in connection with other aspects of the invention In yet some further embodiments, and of particular relevance are patients' populations diagnosed with one of autoimmune disorders, also referred to as disorders of immune tolerance, when the immune system fails to properly distinguish between self and non-self-antigens.

Thus, according to some embodiments, the method of the invention may be used for the treatment of a patient suffering from any autoimmune disorder. In some specific embodiments, the methods of the invention may be used for treating an autoimmune disease such as for example, but not limited to, inflammatory bowel disease (IBD), ulcerative colitis, Crohn's disease, fatty liver disease, Lymphocytic colitis, Ischaemic colitis, Diversion colitis, Behçet's syndrome, Indeterminate colitis, rheumatoid arthritis, systemic lupus erythematosus (SLE), Graft versus Host Disease (GvHD), Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM) and NIDDM, multiple sclerosis (MS), myasthenia gravis, plexus disorders e.g. acute brachial neuritis, polyglandular deficiency syndrome, primary biliary cirrhosis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, arthritis, alopecia areata, polymyalgia rheumatica, Wegener's granulomatosis, Reiter's syndrome, ankylosing spondylitis, pemphigus, bullous pemphigoid, dermatitis herpetiformis, psoriatic arthritis, reactive arthritis, and ankylosing spondylitis, inflammatory arthritis, including juvenile idiopathic arthritis, gout and pseudo gout, as well as arthritis associated with colitis or psoriasis, Pernicious anemia, some types of myopathy and Lyme disease (Late).

In yet some other embodiments, the methods of the invention may be also applicable for treating a subject suffering from an infectious disease. More specifically, such infectious disease may be any pathological disorder caused by a pathogen.

As used herein, the term "pathogen" refers to an infectious agent that causes a disease in a subject host. Pathogenic agents include prokaryotic microorganisms, lower eukaryotic microorganisms, complex eukaryotic organisms, viruses, fungi, *Mycoplasma*, prions, parasites, for example, a parasitic protozoan, yeasts or a nematode.

In yet some further embodiments, the methods of the invention may be applicable in boosting the immune response against a pathogen that may be in further specific embodiment, a viral pathogen or a virus. The term "virus" as used herein, refers to obligate intracellular parasites of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. It should be noted that the term "viruses" is used in its broadest sense to include viruses of the families adenoviruses, papovaviruses, herpesviruses: simplex, varicella-zoster, Epstein-Barr (EBV), Cytomegalo virus (CMV), pox viruses: smallpox, vaccinia, hepatitis B (HBV), rhinoviruses, hepatitis A (HBA), poliovirus, rubella virus, hepatitis C (HBC), arboviruses, rabies virus, influenza viruses A and B, measles virus, mumps virus, human deficiency virus (HIV), HTLV I and II and Zika virus.

In some further embodiments, the methods of the invention may be applicable for immune-related disorder or condition that may be a pathologic condition caused by at least one pathogen. It should be appreciated that an infectious disease as used herein also encompasses any infectious disease caused by a pathogenic agent, specifically, a pathogen. Pathogenic agents include prokaryotic microorganisms, lower eukaryotic microorganisms, complex eukaryotic organisms, viruses, fungi, prions, parasites, yeasts, toxins and venoms. In yet some other specific embodiments, the methods and composition of the invention may be applicable for treating an infectious disease caused by bacterial pathogens. More specifically, a prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes*.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum*, are also encompassed by the invention.

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*.

More specifically, in certain embodiments the methods and compositions of the invention may be suitable for treating disorders caused by fungal pathogens. The term "fungi" (or a "fungus"), as used herein, refers to a division of eukaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei. It should be noted that "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

As noted above, the present invention also provides for the methods and compositions for the treatment of a pathological disorder caused by "parasitic protozoan", which refers to organisms formerly classified in the Kingdom "protozoa". They include organisms classified in Amoebozoa, Excavata and Chromalveolata. Examples include *Entamoeba histolytica, Plasmodium* (some of which cause malaria), and *Giardia lamblia*. The term parasite includes, but not limited to, infections caused by somatic tapeworms, blood flukes, tissue roundworms, ameba, and *Plasmodium, Trypanosoma, Leishmania*, and *Toxoplasma* species.

As used herein, the term "nematode" refers to roundworms. Roundworms have tubular digestive systems with openings at both ends. Some examples of nematodes include, but are not limited to, basal order Monhysterida, the classes Dorylaimea, Enoplea and Secernentea and the "Chromadorea" assemblage.

In yet some further specific embodiments, the present invention provides compositions and methods for use in the treatment, prevention, amelioration or delay the onset of a pathological disorder, wherein said pathological disorder is a result of a prion. As used herein, the term "prion" refers to an infectious agent composed of protein in a misfolded form. Prions are responsible for the transmissible spongiform encephalopathies in a variety of mammals, including bovine spongiform encephalopathy (BSE, also known as "mad cow disease") in cattle and Creutzfeldt-Jakob disease (CJD) in humans. All known prion diseases affect the structure of the brain or other neural tissue and all are currently untreatable and universally fatal.

It should be appreciated that an infectious disease as used herein also encompasses any pathologic condition caused by toxins and venoms.

Thus, the methods of the invention may offer a promising therapeutic modality for a variety of innate and acquired immunodeficiencies caused by immunosuppressive treatments (chemo- and radiotherapy), pathogenic infections, cancer and HSCT. More specifically, Immunodeficiency (or immune deficiency) is a state in which the immune system's ability to fight infectious disease and cancer is compromised or entirely absent. Most cases of immunodeficiency are acquired ("secondary") due to extrinsic factors that affect the patient's immune system. Examples of these extrinsic factors include viral infection, specifically, HIV, extremes of age, and environmental factors, such as nutrition. In the clinical setting, the immunosuppression by some drugs, such as steroids, can be either an adverse effect or the intended purpose of the treatment. Examples of such use are in organ transplant surgery as an anti-rejection measure and in patients suffering from an overactive immune system, as in autoimmune diseases. Immunodeficiency also decreases cancer immunosurveillance, in which the immune system scans the cells and kills neoplastic ones. Still further, Primary immunodeficiencies (PID), also termed innate immunodeficiencies, are disorders in which part of the organism immune system is missing or does not function normally. To be considered a primary immunodeficiency, the cause of the immune deficiency must not be caused by other disease, drug treatment, or environmental exposure to toxins). Most primary immune-deficiencies are genetic disorders; the majority is diagnosed in children under the age of one, although milder forms may not be recognized until adulthood. While there are over 100 recognized PIDs, most are very rare. There are several types of immunodeficiency that include, Humoral immune deficiency (including B cell deficiency or dysfunction), which generally includes symptoms of hypogammaglobulinemia (decrease of one or more types of antibodies) with presentations including repeated mild respiratory infections, and/or agammaglobulinemia (lack of all or most antibody production) and results in frequent severe infections (mostly fatal); T cell deficiency, often causes secondary disorders such as acquired immune deficiency syndrome (AIDS); Granulocyte deficiency, including decreased numbers of granulocytes (called as granulocytopenia or, if absent, agranulocytosis) such as of neutrophil granulocytes (termed neutropenia); granulocyte deficiencies also include decreased function of individual granulocytes, such as in chronic granulomatous disease; Asplenia, where there is no function of the spleen; and Complement deficiency in which the function of the complement system is deficient. Secondary immunodeficiencies occur when the immune system is compromised due to environmental factors. Such factors include but are not limited to radiotherapy as well as chemotherapy. While often used as fundamental anti-cancer treatments, these modalities are known to suppress immune function, leaving patients with an increased risk of infection; indeed, infections were found to be a leading cause of patient death during cancer treatment. Neutropenia was specifically associated with vulnerability to life-threatening infections following chemotherapy and radiotherapy. In more specific embodiments, such secondary immunodeficiency may be caused by at least one of chemotherapy, radiotherapy, biological therapy, bone marrow transplantation, gene therapy, adoptive cell transfer or any combinations thereof.

As described herein above, the invention provides in some aspects thereof therapeutic and prophylactic methods.

It is to be understood that the terms "treat", "treating", "treatment" or forms thereof, as used herein, mean preventing, ameliorating or delaying the onset of one or more clinical indications of disease activity in a subject having a pathologic disorder. Treatment refers to therapeutic treatment. Those in need of treatment are subjects suffering from a pathologic disorder. Specifically, providing a "preventive treatment" (to prevent) or a "prophylactic treatment" is acting in a protective manner, to defend against or prevent something, especially a condition or disease.

The term "treatment or prevention" as used herein, refers to the complete range of therapeutically positive effects of administrating to a subject including inhibition, reduction of, alleviation of, and relief from, an immune-related condition and illness, immune-related symptoms or undesired side effects or immune-related disorders. More specifically, treatment or prevention of relapse or recurrence of the disease, includes the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms. It should be appreciated that the terms "inhibition", "moderation", "reduction", "decrease" or "attenuation" as referred to herein, relate to the retardation, restraining or reduction of a process by any one of about 1% to 99.9%, specifically, about 1% to about 5%, about 5% to 10%, about 10% to 15%, about 15% to about 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%, 100% or more.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

The term "amelioration" as referred to herein, relates to a decrease in the symptoms, and improvement in a subject's condition brought about by the compositions and methods according to the invention, wherein said improvement may be manifested in the forms of inhibition of pathologic processes associated with the immune-related disorders described herein, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the invention described herein.

The terms "delay", "delaying the onset", "retard" and all variations thereof are intended to encompass the slowing of the progress and/or exacerbation of a disorder associated with the immune-related disorders and their symptoms slowing their progress, further exacerbation or development, so as to appear later than in the absence of the treatment according to the invention.

As indicated above, the methods and compositions provided by the present invention may be used for the treatment of a "pathological disorder", specifically, immune-related disorders as specified by the invention, which refers to a condition, in which there is a disturbance of normal functioning, any abnormal condition of the body or mind that causes discomfort, dysfunction, or distress to the person affected or those in contact with that person. It should be noted that the terms "disease", "disorder", "condition" and "illness", are equally used herein.

It should be appreciated that any of the methods and compositions described by the invention may be applicable for treating and/or ameliorating any of the disorders disclosed herein or any condition associated therewith. It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms.

The present invention relates to the treatment of subjects or patients, in need thereof. By "patient" or "subject in need" it is meant any organism who may be affected by the above-mentioned conditions, and to whom the therapeutic and prophylactic methods herein described are desired, including humans, domestic and non-domestic mammals such as canine and feline subjects, bovine, simian, equine and rodents, specifically, murine subjects. More specifically, the methods of the invention are intended for mammals. By "mammalian subject" is meant any mammal for which the proposed therapy is desired, including human, livestock, equine, canine, and feline subjects, most specifically humans.

As described above, the nucleic acid cassette of the invention may be administered by the methods of the invention either ex vivo, by introduction thereof into cells that are being transplanted or transferred to the treated subject, or alternatively in vivo, where the cassette or any vector or composition thereof are directly administered to the subject.

It should be therefore understood that the number of administrations of treatment to a subject may vary. Introducing the genetically modified cells that comprise the cassette of the invention, into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated. In other aspects of the invention as discussed above, the nucleic acid cassette for V(D)J targeted insertion of a nucleic acid sequence of interest is employed to modify cellular DNA in vivo. In these in vivo embodiments, the nucleic acid cassette of the invention may be administered directly to the individual. The nucleic acid cassette may be administered by any of a number of well-known methods in the art for the administration of nucleic acids to a subject. The nucleic acid cassette can be incorporated into a variety of formulations. More particularly, nucleic acid cassette of the present invention can be formulated into pharmaceutical compositions by combination with appropriate pharmaceutically acceptable carriers or diluents. Appropriate pharmaceutical composition applicable for this aspect will be described in more detail herein after.

In yet a further aspect, the invention relates to a nucleic acid cassette. More specifically, the cassette of the invention may comprise the nucleic acid sequence of interest and at least one RSS. In some embodiments, the cassette provided by the invention may be applicable for targeted insertion of at least one nucleic acid sequence of interest into a target genomic locus. It should be further noted that the insertion of the nucleic acid sequence of interest into the target genomic locus may be facilitated, mediated and/or performed by RAG-catalyzed recombination between at least one genomic RSS flanking the target genomic locus and at least one RSS comprised within the nucleic acid cassette.

It should be appreciated that the nucleic acid cassette of the invention, as being dependent on RAG activity, may be also referred to herein as the "V(D)J targeting cassette" or "V(D)J targeting nucleic acid cassette".

In some specific embodiments, the nucleic acid cassette may be flanked on both the 5' and 3' ends thereof by RSS.

In yet some further specific embodiments, the RSS may be at least one of 12 RSS, 23 RSS and 22 RSS. In some particular and non-limiting embodiments, RSS applicable in the present invention may by any of the RSSs as denoted by nucleic acid sequence of SEQ ID NO. 36, 37, 38, 39, 40 and 41.

Therefore, in some embodiments the cassettes of the invention may be flanked either by "same" RSSs (two 12 RSSs or two 23 RSSs), or by an incompatible pair of a 12 RSS and a 23 RSS.

In some particular embodiments specifically suitable for VDJ targeting in the B lineage, the cassette of the invention may be flanked by two "outward facing" 12 RSSs to integrate between a V and a J segment of the heavy chain (as also illustrated by FIG. 5A). In yet some further alternative embodiments, a suitable configuration for VDJ targeting in the T lineage, may be a cassette flanked by two "downstream facing" 23 RSSs to integrate between a D and a J segment of a β chain (as also illustrated by FIG. 5B).

In some embodiments, the RSS used by the methods and cassettes of the invention may be naturally occurring, selected by a screen, rationally optimized, selected based on compatibility or incompatibility with other RSSs.

In certain embodiments, the cassette of the invention may further comprise at least one genetic element. Specifically, such genetic element may be at least one of: an internal ribosome entry site (IRES), a 2A peptide coding sequence, a promoter and any fragments thereof, a splice donor, a splice acceptor, a degron, a 3 frame stop, a protein stabilizing sequence, a signal peptide, a stop codon, a polyadenylation site, a transcription enhancer, a switch region, an mRNA stabilizing sequence and a protein stabilizing sequence.

As noted above, several genetic elements may be included in the cassette of the invention. In some specific embodiments, at least one SD may be included. More specifically, for VDJ targeting in the B cell lineage, a heavy chain constant region may not be encoded by the cassette of the invention, but instead a downstream splice donor (SD) may be included therein thereby allowing the utilization of endogenous constant region. In some embodiments, such cassette may encode an Ab light chain ($V_L J_L C_L$) and a variable region of a heavy chain ($V_H D_H J_H$) separated by a 2A peptide, more specifically, such cassette may include $V_L J_L C_L$-2A-$V_H D_H J_H$-SD. In some specific embodiments, at least one SA may be included. In some embodiments, such cassette may encode an Ab light chain ($V_L J_L C_L$) and a variable region of a heavy chain ($V_H D_H J_H$) separated by a 2A peptide, more specifically, such cassette may include SA-$V_L J_L C_L$-2A-$V_H D_H J_H$-SD.

In yet some further embodiments, a minimal promoter (mP) may be included in the cassette of the invention. In some embodiments, such cassette may encode an Ab light chain ($V_L J_L C_L$) and a variable region of a heavy chain ($V_H D_H J_H$) separated by a 2A peptide, more specifically, such cassette may include: mP-$V_L J_L C_L$-2A-$V_H D_H J_H$-SD.

In yet some further embodiments, for VDJ targeting in the T cell lineage, several different specific configurations for VDJ targeting may be used. More specifically, in some embodiments, when targeting a transgenic TCR cassette to the TCR β chain locus, a heavy chain constant region may not be encoded by the cassette of the invention but instead, the cassette may include a downstream SD to allow the utilization of endogenous constant region. In some embodiments, the cassette may encode a TCR a chain (VαJαCα) and a variable region of a β chain (VβDβJβ) separated by a 2A peptide, specifically, VαJαCα-2A-VβDβJβ-SD. Still further in some embodiments, when targeting a CAR cassette to the TCR β chain locus, the cassette of the invention may comprise a nucleic acid sequence encoding the full CAR gene, ending with a stop codon, and only then a SD. In some specific embodiments, at least one SA may be included. In some embodiments, such cassette may encode an TCR a chain (VαJαCα) and a variable region of a β chain (VβDβJβ) separated by a 2A peptide, specifically, such cassette may include SA-VαJαCα-2A-VβDβJβ—SD.

In yet some further embodiments, a minimal promoter (mP) may be included in the cassette of the invention. In some embodiments, such cassette may encode an TCR a chain (VαJαCα) and a variable region of a β chain (VβDβJβ) separated by a 2A peptide, specifically, such cassette may include: mP-VαJαCα-2A-VβDβJβ-SD.

In still some further specific embodiments, the cassette of the invention may comprise two or more nucleic acid sequences of interest separated by at least one genetic element. Such genetic element may be at least one of: an IRES, a 2A peptide coding sequence and a promoter. Thus, in some embodiments, the cassette of the invention may encode several peptides (e.g. two Ab chains) and these may be separated by 2A peptides. In yet some specific embodiment a preceding IRES and an intervening 2A peptide may be included in the cassette of the invention that encodes the heavy and the light chains, specifically, such cassette may comprise RSS-IRES-$V_L J_L C_L$-2A-$V_H D_H J_H$-SD-RSS. More specifically, an IRES sequence followed by a sequence encoding a light chain V, J and C segments. An 2A sequence separates between the light chain and heavy chain segments VDJ that are followed by a splice donor site that allow that allow specific splicing to include the endogenous C region.

In yet some further embodiments, the nucleic acid sequence of interest may be a protein coding nucleic acid sequence or a non-coding sequence.

In some specific embodiments, the nucleic acid sequence of interest may be a protein coding gene. More specifically, such protein may be at least one of: a therapeutic protein or peptide, a prophylactic protein, a tolerizing protein, an immunizing protein, a toxic protein, a suicide protein, specifically, an inducible suicide protein, a marker protein, an imaging protein and a fusion or chimeric protein.

In some specific and non-limiting embodiments, a suicide gene may be further comprised within the cassette of the invention. In yet some specific embodiments the invention provides a cassette comprising an inducible suicide gene for the specific elimination of targeted lymphocytes, specifically, in case the expression is found to be associated with adverse outcomes. In more particular embodiments, the cassette of the invention may further comprise an upstream caspase gene fused to an inducible dimerization domain (iCasp9). In certain embodiments, the cassette of the invention may comprise RSS-IRES-iCasp9-2A-$V_L J_L C_L$-2A-$V_H D_H J_H$-SD-RSS. More specifically, an IRES sequence followed by a sequence encoding caspase 9, followed by 2A sequence that separates between the caspase and a light chain V, J and C segments. An additional 2A sequence separates between the light chain and heavy chain segments VDJ that are followed by a splice donor site that allow that allow specific splicing to include the endogenous C region.

In yet some further embodiments, the nucleic acid sequence of interest may encode at least one of a small non-coding RNA molecule, specifically, miRNA, siRNA, shRNA and the like. In yet some further embodiments, the small non-coding RNA molecule may be specifically directed against a TCR chain, a BCR chain, an immune checkpoint gene, an apoptotic gene.

More specifically, in some embodiments, the cassette of the invention may target a full TCR gene (TCRα-2A-TCRβ) into the TCRβ chain locus, in such case, an miRNA directed against the TCRα chain, may be further added in the cassette to prevent cross-dimerization. In yet some further embodiments, miRNAs against the non-targeted allele may be used. Knockdown of the other allele is desired only if natural allelic exclusion is absent or incomplete, for example when introducing a CAR gene rather than a TCR and thus not providing all natural signals for allelic exclusion. Still further, in some embodiments, the cassette of the invention may further comprise nucleic acid sequence encoding miRNA against the immune checkpoint protein PD1 in T cells. In some further embodiments, the cassette of the invention may further comprise nucleic acid sequence encoding a miRNA against an apoptotic gene. In further embodiments, such miRNA may be used in conjunction with an inducible suicide gene as described above. Accordingly, in certain embodiments, the cassette of the invention may comprise RSS-IRES-iCasp9-2A-$V_L J_L C_L$-2A-$V_H D_H J_H$-SD-miRNA-RSS. More specifically, an IRES sequence followed by a sequence encoding caspase 9, followed by 2A sequence that separates between the caspase and a light chain V, J and C segments. An additional 2A sequence separates between the light chain and heavy chain segments VDJ that are followed by a splice donor site, and an additional sequence encoding miRNA. The cassette is flanked by an additional RSS sequence.

In yet some further embodiments, the nucleic acid sequence of interest comprised within the cassette of the invention may encode at least one of a receptor and an antibody or any fragment/s or chimera/s thereof.

In some specific embodiments, the nucleic acid sequence of interest of the cassette of the invention may encode at least one receptor. Specifically, any one of, or at least one of a TCR, CAR and a BCR.

In some embodiments, the nucleic acid sequence of interest may encode a receptor that may be a naturally occurring receptor, receptor selected by a screen or rationally designed receptor.

More specifically, for V(D)J targeting T cells, receptors targeted at specific antigens, may be used in the cassettes of the invention for targeted integration of several different receptors of clinical relevance. Thus, in some specific embodiments, the cassette of the invention may comprise a nucleic acid sequence encoding an anti CD19 CAR. Such cassette may be effective for treating B cell malignancies. In some specific embodiments, such CD19 CAR may comprise the amino acid sequence as denoted by SEQ ID NO. 10 or any derivatives thereof. In yet some further embodiments, the cassette of the invention may comprise a nucleic acid sequence encoding an anti-Tn-MUC1 CAR, which targets a highly cancer specific glycoform. In some specific embodiments, such Tn-MUC1 CAR may comprise the amino acid sequence as denoted by SEQ ID NO. 11 or any derivatives thereof. In some further embodiments, the cassette of the invention may comprise nucleic acid sequence encoding an NY-ESO-1-specific TCR construct. In some specific embodiments, such NY-ESO-1CAR may comprise the amino acid sequence as denoted by SEQ ID NO. 12 or any derivatives thereof.

In certain specific embodiments, the nucleic acid sequence of interest may encode at least one antibody. In more particular embodiments, such antibody may be any one of: full length antibody, antibody fragment, scFv, bi-specific antibody, tri-specific antibody, BiTE and V-NAR.

In some embodiments, the nucleic acid sequence of interest may encode an antibody that may be a naturally occurring antibody, antibody or fragments thereof selected by a screen or rationally designed antibody.

In more specific embodiments, for targeting B cells, specifically, differentiating B cells that express RAG, V(D)J cassette for targeted insertion of antibody sequences, specifically, antibodies of clinical relevance. More particularly, in some embodiments, the cassette of the invention may comprise a nucleic acid sequence encoding at least one anti-viral antibody, specifically, at least one anti-HIV antibody, more specifically, the 3BNC117 antibody. In some particular and non-limiting embodiments such 3BNC117 antibody may comprise the amino acid sequence as denoted by SEQ ID NO. 13 or any derivatives thereof. In yet some further embodiments, the cassette of the invention may comprise a nucleic acid sequence encoding at least one anti-TNFα antibody, specifically, an antibody effective in auto-immune diseases, more specifically, the Adalimumab (Humira™) antibody. In some particular and non-limiting embodiments such Adalimumab antibody may comprise the amino acid sequence as denoted by SEQ ID NO. 14 or any derivatives thereof. In yet some further embodiments, the cassette of the invention may comprise a nucleic acid sequence encoding at least one anti MUC1 glycoform antibody, specifically, the PankoMab-GEX. In some particular and non-limiting embodiments such PankoMab-GEX antibody may comprise a heavy chain variable region that comprises the amino acid sequence as denoted by SEQ ID NO. 15, and a light chain variable region comprising the amino acid sequence as denoted by SEQ ID NO. 16 or any derivatives thereof.

In yet some further specific embodiments, the nucleic acid cassette of the invention may comprise a nucleic acid encoding a secreted antibody directed against or specific for an autoantigen. In yet some further embodiments, said cassette may further comprise a nucleic acid sequence encoding a BCR directed against and/or specific for a foreign antigen.

A non-limiting example for such cassette that offers an inducible secretion of antibodies, is illustrated in FIG. 20. Such cassette may include RSS-IRES-scFv/BiTe (specific for an autoantigen)-IRES-BCR (specific for a foreign antigen)-RSS.

In some embodiments, the target genomic locus targeted by the cassette of the invention may be at least one of Immunoglobulin heavy chain locus, Immunoglobulin κ chain locus, Immunoglobulin λ chain locus, TCRβ chain locus, TCRα chain locus, TCRγ chain and the TCRδ chain locus.

In certain embodiments, the cassette of the invention may be comprised within a nucleic acid vector. More specifically, such vector may be any one of a viral vector, a non-viral vector and a naked DNA vector.

It should be appreciated that any of the nucleic acid cassettes described herein as specific and non-limiting embodiments, are encompassed by the invention and may be used in any of the methods described herein before and in any of the compositions described herein after.

The invention provides nucleic acid cassette and methods using the cassette. The term "nucleic acid", "nucleic acid sequence", or "polynucleotide" and "nucleic acid molecule" refers to polymers of nucleotides, and includes but is not limited to deoxyribonucleic acid (DNA), ribonucleic acid (RNA), DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included. The terms should also be understood to include, as equivalents, analogs of either RNA or DNA made from nucleotide analogs, and, as applicable to the embodiment being described, single-stranded (such as sense or antisense) and double-stranded polynucleotides. Preparation of nucleic acids is well known in the art.

All elements comprised within the cassette of the invention are operably linked together. The term "operably linked", as used in reference to a regulatory sequence and a structural nucleotide sequence, means that the nucleic acid sequences are linked in a manner that enables regulated expression of the linked structural nucleotide sequence.

Still further, it should be understood that the invention encompasses as additional aspects thereof any vector or vehicle that comprise any of the cassettes described by the invention.

Still further, the invention also provides any cell, specifically a mammalian host cell that express the cassettes of the invention or any of the vectors or vehicles described by the invention. In some specific embodiments, such host cells may be immune-related cells, specifically lymphocytes, more specifically, lymphocytes either obtained in some embodiments from a healthy subject or in other embodiments, obtained from a subject suffering from an immune-related disorder. Specific embodiments relate to B, T and NK T lymphocytes that are transduced or transfected with the cassettes of the invention or any vector or vehicle thereof. It should be understood that any of the cells, vectors and subjects described by the invention also apply for these aspects as well.

In yet a further aspect, the invention relates to a pharmaceutical composition comprising an effective amount of at least one nucleic acid cassette, or any vector or cell comprising the cassette of the invention. More specifically, the cassette of the composition of the invention may comprise the nucleic acid sequence of interest and at least one RSS. In some embodiments, the cassettes provided by the compositions of the invention may be applicable for targeted insertion of at least one nucleic acid sequence of interest into a target genomic locus. It should be noted that the insertion of the nucleic acid sequence of interest into the target genomic locus may be facilitated, mediated and/or performed by RAG-catalyzed recombination between at least one genomic RSS flanking the target genomic locus and at least one RSS comprised within said nucleic acid cassette. In some optional embodiments, the compositions of the invention may further comprise at least one of pharmaceutically acceptable carrier/s, diluent/s, excipient/s and additive/s.

The compositions of the invention may comprise an effective amount of the cassette of the invention or of any vector thereof or of any cell comprising the same. The term "effective amount" relates to the amount of an active agent present in a composition, specifically, the cassette of the invention as described herein that is needed to provide a desired level of active agent in the bloodstream or at the site of action in an individual (e.g., the thymus or bone marrow) to be treated to give an anticipated physiological response when such composition is administered. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein. An "effective amount" of a the V(D)J targeting cassette of the invention can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The pharmaceutical compositions of the invention can be administered and dosed by the methods of the invention, in accordance with good medical practice, systemically, for example by parenteral, e.g. intrathymic, into the bone marrow and intravenous. It should be noted however that the invention may further encompass additional administration modes. In other examples, the pharmaceutical composition can be introduced to a site by any suitable route including intraperitoneal, subcutaneous, transcutaneous, topical, intramuscular, intraarticular, subconjunctival, or mucosal, e.g. oral, intranasal, or intraocular administration.

Local administration to the area in need of treatment may be achieved by, for example, by local infusion during surgery, topical application, direct injection into the specific organ (thymus, bone marrow, spleen, lymph nodes), etc. More specifically, the compositions used in any of the methods of the invention, described herein before, may be adapted for administration by parenteral, intraperitoneal, transdermal, oral (including buccal or sublingual), rectal, topical (including buccal or sublingual), vaginal, intranasal and any other appropriate routes. Such formulations may be prepared by any method known in the art of pharmacy, for example by bringing into association the active ingredient with the carrier(s) or excipient(s).

In yet some further embodiments, the composition of the invention may optionally further comprises at least one of pharmaceutically acceptable carrier/s, excipient/s, additive/s diluent/s and adjuvant/s.

More specifically, pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients, specifically, the V(D)J targeting cassette of the invention with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question.

Still further, pharmaceutical preparations are compositions that include one or more targeting cassette present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of the V(D)J targeting cassette can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

Still further, the composition/s of the invention and any components thereof may be applied as a single daily dose or multiple daily doses, preferably, every 1 to 7 days. It is specifically contemplated that such application may be carried out once, twice, thrice, four times, five times or six times daily, or may be performed once daily, once every 2 days, once every 3 days, once every 4 days, once every 5 days, once every 6 days, once every week, two weeks, three weeks, four weeks or even a month. The application of the combination/s, composition/s and kit/s of the invention or of any component thereof may last up to a day, two days, three days, four days, five days, six days, a week, two weeks, three weeks, four weeks, a month, two months three months or even more. Specifically, application may last from one day to one month. Most specifically, application may last from one day to 7 days.

Still further, it should be understood, that the invention further encompasses any cell that comprise the nucleic acid cassette of the invention. In more particular embodiments, the cell of the invention may be transformed or transfected with at least one nucleic acid cassette according to the invention that enables the targeted insertion of a nucleic acid sequence of interest into a target locus within the cell. It should be noted that any of the cells discussed above may applicable for this aspect, specifically, any lymphocyte progenitor, ex vivo differentiating lymphocytes, HSPCs and iPSCs. It should be appreciated that these cells may be used for the therapeutic and prophylactic methods of the invention and may therefore include in some embodiments thereof cells of an autologous or allogeneic source.

As used herein, a cell has been "transformed" or "transfected" by exogenous or heterologous DNA, e.g. the V(D)J cassette of the invention, when such DNA has been introduced inside the cell. The transforming DNA may be integrated (covalently linked) into the genome of the cell. With respect to the present invention, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

In yet a further aspect, the invention provide an effective amount of at least one nucleic acid cassette or any composition thereof for use in a method for targeted insertion of at least one nucleic acid sequence of interest into a target genomic locus in a mammalian cell. More specifically, the cassette of the invention may comprise the nucleic acid sequence of interest and at least one RSS. It should be further noted that the insertion of the nucleic acid sequence of interest into the target genomic locus may be facilitated, mediated and/or performed by RAG-catalyzed recombination between at least one genomic RSS flanking the target genomic locus and at least one RSS comprised within the nucleic acid cassette. The invention further provides an effective amount of at least one of the cassettes described herein, any compositions or vehicles thereof or any cell expressing the cassette of the invention for use in a method for targeted insertion of at least one nucleic acid sequence of interest into a target genomic locus of a cell in a mammalian subject.

In a further aspect of the invention, the invention provide an effective amount of at least one nucleic acid cassette or any composition thereof or vehicles thereof or any cell expressing the cassette of the invention for use in a method for treating, preventing, ameliorating, inhibiting or delaying the onset of a pathologic disorder in a mammalian subject. More specifically, the cassette of the invention may comprise the nucleic acid sequence of interest and at least one RSS. The cassette administered to the treated subject targets insertion of the at least one nucleic acid sequence of interest comprised therein into a target genomic locus in a the treated subject. It should be further noted that the insertion of the nucleic acid sequence of interest into the target genomic locus in the treated subject may be facilitated, mediated and/or performed by RAG-catalyzed recombination between at least one genomic RSS flanking the target genomic locus and at least one RSS comprised within the nucleic acid cassette.

In some specific embodiments the nucleic acid cassette or any compositions or vectors thereof for use in accordance with the invention, may be flanked on both the 5' and 3' ends thereof by RSS.

In more specific embodiments, the RSS comprised within the cassette for use in accordance with the invention may be at least one of 12 RSS, 23 RSS and 22 RSS. In some particular and non-limiting embodiments, RSS applicable in the present invention may by any of the RSSs as denoted by nucleic acid sequence of SEQ ID NO. 36, 37, 38, 39, 40 and 41.

In some embodiments, the RSS of the cassettes for use in accordance with the invention may be naturally occurring, selected by a screen, rationally optimized, selected based on compatibility or incompatibility with other RSSs.

In yet some further specific embodiments, the nucleic acid cassette for use in accordance with the invention may further comprise at least one genetic element, said genetic element is at least one of: an IRES, a 2A peptide coding sequence, a promoter or any functional fragment thereof, a splice donor, a splice acceptor, a degron, a 3 frame stop, a protein stabilizing sequence, a signal peptide, a stop codon, a polyadenylation site, a transcription enhancer, a switch region, an mRNA stabilizing sequence and a protein stabilizing sequence.

In some specific embodiments, the cassette for use in accordance with the invention may comprise two or more nucleic acid sequences of interest separated by at least one genetic element. In more specific embodiments, such genetic element may be at least one of an IRES, a 2A peptide coding sequence and a promoter.

In certain embodiments, the nucleic acid sequence of interest comprised within the cassette for use in accordance with the invention may be a protein coding nucleic acid sequence or a non-coding sequence.

In some specific embodiments, where the nucleic acid sequence of interest is a protein coding gene, such protein may be at least one of: a therapeutic protein or peptide, a prophylactic protein, a tolerizing protein, an immunizing protein, a toxic protein, an inducible suicide protein, a marker protein, an imaging protein and a fusion or chimeric protein.

In yet some further alternative embodiments, the nucleic acid sequence of interest may encode at least one small non-coding RNA molecule. More specifically, such one small non-coding RNA molecule may be for example, miRNA, siRNA, shRNA or any of the one small non-coding RNA molecules described by the invention herein before. In some further embodiments, the small non-coding RNA molecule may be specifically directed against a TCR chain, a BCR chain, an immune checkpoint gene or an apoptotic gene.

In more specific embodiments, the nucleic acid sequence of interest of the cassette for use in accordance with the invention may encode at least one of a receptor and an antibody or any fragment/s or chimera/s thereof.

In some particular embodiments, the nucleic acid sequence of interest may encode at least one receptor. More specifically, such receptor may be any one of: a TCR, CAR and a BCR.

In some embodiments, the nucleic acid sequence of interest may encode a receptor that may be a naturally occurring receptor, receptor selected by a screen or rationally designed receptor.

In yet some further particular embodiments, the nucleic acid sequence of interest may encode at least one antibody. More specifically, such antibody may be any one of full length antibody, antibody fragment, scFv, bi-specific antibody, tri-specific antibody, BiTE and V-NAR.

In some embodiments, the nucleic acid sequence of interest may encode an antibody that may be a naturally occurring antibody, antibody or fragments thereof selected by a screen or rationally designed antibody.

In some embodiments, the nucleic acid cassette for use in accordance with the invention may comprise a nucleic acid sequence encoding a secreted antibody directed against and specific for an autoantigen. This cassette may further comprise a nucleic acid sequence encoding a BCR directed against and specific for a foreign antigen. It should be noted that in certain embodiments, these two nucleic acid sequences are separated by at least one genetic element, for example, an IRES, a 2A peptide coding sequence and a promoter.

In certain embodiments, the target genomic locus for the targeted insertion of the nucleic acid sequence of interest comprised within the cassette for use in accordance with the invention may be at least one of Immunoglobulin heavy chain locus, Immunoglobulin κ chain locus, Immunoglobulin λ chain locus, TCRβ chain locus, TCRα chain locus, TCRγ chain and the TCRδ chain locus.

It should be appreciated that in certain embodiments, the nucleic acid cassette for use in accordance with the invention may be comprised within a nucleic acid vector. More specifically, such vector may be any one of a viral vector, a non-viral vector and a naked DNA vector.

In more specific embodiments, the vector may be a viral vector. Specifically, suitable viral vectors may be any one of rAAV, ssAAV, scAAV, SV40 vector, Adeno virus vector, helper-dependent Adeno viral vector, retroviral vector and lentiviral vector.

In yet some further embodiments, the cassette for use in accordance with the invention may be comprised within a non-viral vector. Such vector may be any one of plasmid, minicircle and linear DNA.

In yet some further embodiments, the vector may be a naked DNA vector, specifically, any one of plasmid, minicircle and linear DNA.

It should be noted that in certain embodiments, the cassette for use in accordance with the invention, leads to targeted insertion of the nucleic acid sequence of interest into a target locus in a cell of said mammalian subject. It should be noted that the targeted insertion may be mediated and facilitated by RAG complex. Thus, in some specific embodiments, the targeted cell/s of the subject may naturally express RAG. However, it should be noted that the invention further encompasses in some embodiments thereof, the option that the target cells of the administered subject may be either stably RAG expressing or inducibly RAG expressing. Such cells in some embodiments may be transfected with RAG expression vectors. As indicated herein before, in some embodiments, RAG expressing cells may be cells that undergo VDJ recombination. In yet some further embodiments, RAG expressing cell may further encompass cells that already underwent VDJ recombination but still express RAG.

In certain embodiments, the cell/s of the administered subject targeted by the cassette for use in accordance with the invention may be any one of thymocytes, HSPCs and mobilized HSPCs.

In yet some specific embodiments, the cells targeted by the cassette for use in accordance with the invention may be thymocytes of any subsect. More specifically, such cells may be thymocytes of any one of the DN1, DN2, DN3, DN4, DP and SP subsets, as described herein above. In yet some further embodiments, the cells targeted by the cassette for use in accordance with the invention may be splenocytes of any subsect, or any lymphocytes obtained or present in lymph nodes and bone marrow.

The uses described herein for the cassette or any cells, vehicles or compositions thereof may be applied in some embodiments to any disease, disorder, or natural cellular process that would benefit from modulating cell activity by integrating a gene of interest.

In some specific embodiments the uses described herein for the cassette or any cells, vehicles or compositions thereof may be applied for treating a subject in need. In more particular and non-limiting embodiments, such subject may be a subject suffering of an immune-related disorder. It should be noted that any of the immune related disorders described herein before in connection with other aspects of the invention are also applicable in the present aspects.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. Thus, as used herein the term "about" refers to +10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, and/or parts, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

EXAMPLES

Materials and Reagents
Reagents:

Imatinib: Gleevec® (STI-571, $C_{29}H_{31}N_7O$).
Plasmids and Viral Vectors:
pGEMT (cat #A3600, by Promega)
Ad5-serotype-6 helper-free plasmid: pDGM6 obtained from the D. W. Russell lab at University of Washington.
Cell Lines:
Jurkat cells ATCC® TIB-152™
V-Abl immortalized murine Pro B cells obtained from the L. Deriano lab at the Pasteur institute.
HEK293-T-ATCC® CRL-3216™.
Kits:
Quick-RNA™ RNA microprep kit (Zymo Research).
Takara "All Serotype" purification kit (Cat #6666).
Animals and Animal Models:
C57BL/6 mice obtained from the Jackson labs.
Experimental Procedures
Transfection with GFPi-Redless Plasmid:
V-Abl immortalized murine Pro B cells were transfected by electroporation (1600V, 20 ms, 1 pulse) with the GFPi-redless plasmid containing a 23-consensus RSS and a 12-consensus RSS. Cells recuperated for 4 hours, then given 3 μM Imatinib (Im) for induction of differentiation.

Integration by VDJ Targeting of a Gene Coding for an Antibody into the IgK Locus in Inducibly Differentiating B Cell Progenitors:

Immortalized and inducible differentiating Pro-B cells (Lescale et al. 2017 Mech Ageing Dev. 2017 July; 165(Pt A):3-9) were cultured at 37° C. with 5% $CO_2$. $10^6$ cells were taken, washed with PBS twice (Biological Industries) and then mixed with an amount of 2.3 μg Donor DNA (i.e. the plasmid pADN110, see illustrated map in FIG. 10). Neon™ Electroporation (Invitrogen) was performed using 10 μL tips (Invitrogen) at 1600 v, 20 ms, 1 pulse. Neon™ Buffer R was replaced with Opti-MEM™ (Life Technologies) and Neon™ buffer E1 with Opti-MEM™ 10% Glycerol. Cells post electroporation were plated on RPMI 1640 (Biological Industries) supplemented with 10% FBS (Sigma) and 50 μM B-Mercaptoethanol. PBS was supplemented to media 24 h post electroporation. Imatinib was supplemented to media 24 h post electroporation to a concentration of 3 μM.

A volume of 1.5 ml was taken from culture for RNA extraction 3 days post electroporation, using Quick-RNA™ RNA microprep kit (Zymo Research) according to the manufacturer's protocol. 2 μg RNA were taken for Reverse transcriptase reaction using oligo dT(15) primer with RevertAid Reverse transcriptase (ThermoFisher-Merck) according to manufacturer's protocol. PCR reaction on the cDNA template was done using 2×taq PCR MasterMix (Tiangen) according to manufacturer's protocol. Gel electrophoresis was performed on a 1.7% Agarose gel supplemented with Ethidium Bromide. The following primers were used:
ECMV IRES RI as denoted by SEQ ID NO: 19
5'-CATATAGACAAACGCACACCGGC-3'
IgKVm-rec-F1 as denoted by SEQ ID NO: 20
5'-GTCCCTGCCAGGTTYAGTGGCAGTGGRT-CWRGGAC-3'. It should be noted that in accordance with IUPAC nomenclature, "Y" may be C or T, "R" may be a or G and "W" may be A or T.

Extraction of Primary Mouse Bone Marrow and Enrichment for IL7-Receptor-Positive Progenitor Cells:

Two female C57Bl/6 mice, 8-12 weeks old, were used for each preparation of IL7-receptor-enriched bone marrow cells (IL7R cells). Hind and back longitude bones were flushed with RPMI medium containing 10% FBS, 100 U/ml Penicillin, 100 μg/ml Streptomycin and 2 mM EDTA. Clumps were disaggregated with a pipette and passed through a 40 μl cell strainer. No RBC lysis was performed.

Pelleted cells were washed once with PBS (without Ca$^{++}$ and without Mg) supplemented with 10% FBS (PBS-FBS) and then re-suspended in 200 µl PBS-FBS, per mouse. PE-conjugated anti mouse IL7R (cat #130-102-551 by Miltenyi) was added at: 10 µl/mouse/200 µl PBS-FBS. Binding was performed at 4-6° C. for 30 min. Cell suspension was subsequently washed twice with PBS-FBS and re-suspended in 80 µl PBS-FBS per mouse. Magnetic nanobeads conjugated to a secondary antibody directed against the PE moiety of the primary antibody (cat #130-048-801 by Miltenyi) were added at: 20 µl/mouse/80 µl PBS-FBS. Binding was performed at 4-6° C. for 30 min. Cell-bead conjugates were washed once with PBS-FBS and separated on a magnetic column (cat #130-042-401 by Miltenyi). Typically, 2-4 million IL7R+ enriched cells per mouse were obtained. Cells were subsequently transduced, as detailed below, and cultured for in vitro differentiation in MEM-alpha medium, supplemented with 20% heat inactivated FBS, 100 U/ml Penicillin and 100 µg/ml Streptomycin.

Flow Cytometry:

Staining was performed on non-fixed cells, in azide containing buffer, to prevent capping and internalization of expressed cell surface receptors.

The employed antibodies are as follows:

| Antibody: | Source | Cat# |
|---|---|---|
| Mouse IL7 receptor-PE | Miltenyi | 130-102-551 |
| Mouse IgK-Vio Blue | Miltenyi | 130-105-860 |
| Mouse IgM-APC | BioLegend | 406509 |
| Mouse Isotype control-APC | BioLegend | 400511 |
| Mouse CD19-FITC | BioLegend | 115505 |

Acquisition was performed on the "Attune NXT" flow cytometer and data analysis was performed with the TAU site-licensed Kaluza software.

Construction of a Minimal Promoter Trans-Recombination Donor Vector: dsAAV-360A:

A VDJ-targeting vector coding for a segment of a human IgK variable region, specifically, the Vκ 3-15 segment, and further coding for an HA tag was constructed. The human IgK variable region includes the natural V promoter, which is a "minimal promoter" i.e. it can only drive transcription when adjacent to an enhancer. Therefore, transcription occurs only after desired integration into the mouse VDJ loci (which are adjacent to a mouse enhancer at the Igκ/λ) or IgH loci). The nucleic acid sequence of the above segment is as denoted by SEQ ID NO: 25.

Figure 1:
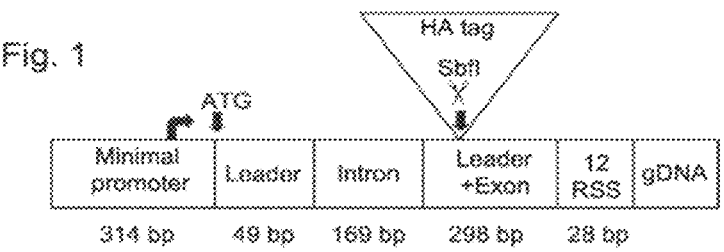
FIG. 1. AAV vector

A natural human germline gene encoding for the IgKappa-V3-15 was PCR-amplified. The amplified region spanned 929 bases and included 314 bp of the minimal promoter that comprises the nucleic acid sequence as denoted by SEQ ID NO. 51 (upstream of the Leader ATG) and 71 bp downstream on the RSS (12-spacer). The gene was cloned into Bluescript SK-, and 2 tandem in-frame repeats of the HA tag (mouse codon optimized) were inserted into the natural SbfI site of the human IgKV3-15 gene (see schematic representation of the construct in FIG. 1). The HA-tagged gene was then cloned into a double strand AAV vector, which was pre-cloned to contain flanking *Drosophila melanogaster* (DM) stuffer sequences, to support optimal vector replication and packaging efficiency. The complete map of the dsAAV vector is illustrated in FIG. 2.

AAV Serotype 6 Preparation of dsAAV-360A Vector:

Vector stock was prepared by transfecting HEK293-T cells with the vector plasmid: dsAAV360A, alongside the Ad5-serotype-6 helper-free plasmid: pDGM6.

Purification was performed by using the Takara "All Serotype" purification kit (Cat #6666), according to the manufacturer's protocol.

dsAAV-360A Vector Transduction of IL7R. Enriched Bone Marrow Cells:

Approximately 2-4 million of IL7R+ enriched cells were transduced in a 24-well with 70% of vector progeny received from the Takara "All Serotypes" kit, at a ratio of 1:9 with serum-less medium (Opti-MEM™). Spinoculation at 1200×g for 45 minutes was performed and 2 hours after initiating the transduction, full medium (MEM-alpha) containing 10% FBS was added at 3× volume excess. Cells were harvested 3 days post transduction.

RNA Isolation and RT-PCR Analysis:

RNA isolation was performed using the Quick-RNA™ RNA microprep kit (Zymo Research) according to the manufacturer's instructions. Reverse Transcription reactions were performed with 100-1000 ng total RNA, using 100 pmol oligo-dT as primer, 200 U of RNase H-minus M-MLV-point mutant (cat #M3682 by Promega), at 50° C. Typically, about 5% of the reverse transcription reaction was taken for PCR in 20 µl total volume, using standard conditions, a regular Taq polymerase ready-mix (cat #EZ-3006, by HyLabs) for 35 cycles of reaction, followed by 7 minutes tailing at 72° C. Primer locations and sequences are illustrated in FIG. 3.

mHA-SbfI-F1 primer as denoted by SEQ ID NO: 21
CTTACCCCTATGATGTGCCTGACTACGCTTGCA.

IgKCm-rec-Rev2 primer as denoted by SEQ ID NO: 22
GGATGGTGGAAGATGGATAC.

RT-PCR products were cloned into a TA cloning vector: pGEMT (cat #A3600, by Promega). Sequencing was then performed at the inter-departmental life sciences unit (IDRFU). Sequence alignment and analysis was performed by licensed SnapGene 4.1.5 software.

Intrathymic Injection of Cells Stained Fluorescently with CESE:

About 1*10$^6$ Jurkat-cells stained with CFSE (Carboxyfluorescein succinimidyl ester) were intrathymically injected with ultrasound guidance using 30-gauge insulin syringes (Tuckett A Z et al., J Hematol Oncol. 2017 16; 10(1): 109; Tuckett A Z et al., Ultrasound Med Biol. 2015; 41:1105-1111) to 6-8 weeks old C57BL/6 mice. The thymus was isolated immediately after injection and the fluorescent signal from CFSE stained cells was detected using Maestro imaging system.

Intrathymic Injection of Luciferase Transduced Cells:

Murine bone marrow cells were obtained from 6-8 weeks old C57BL/6 mice and used either fresh (BM) or after enrichment for Lin– cells (Lin–). Cells were transduced retrovirally to express Luciferase. 1E6 transduced cells were intrathymically injected using ultrasound guidance with 30 gauge syringes to 6-8 weeks old C57BL/6 mice. The signal of luciferase was detected after injection of Luciferin using the Biospace imaging system.

Example 1

V(D)J Targeting Strategy

VDJ targeting in accordance with the present invention, employs rAAV as well as the natural process of V(D)J recombination, taking place in developing lymphocytes. In natural V(D)J recombination, during T and B cell maturation, the genes to encode the two chains of a TCR or an Antibody are rearranged in a nearly random fashion from V and J gene segments (in α and γ TCR chains and Antibody light chains) or V, D and J segments (in β or δ TCR chains or Antibody heavy chain). V(D)J recombination is catalyzed by the RAG complex, composed of the RAG1 and RAG2 proteins as illustrated in FIG. 4A. RAG recognizes recombination signal sequences (RSSs) and recombines them to join together appropriate gene segments. RAG activity is associated with genomic instability and therefore, the inventors refrain from overexpressing RAG, but rather rely on its endogenous expression only. Flanking of a receptor/Antibody gene with appropriate RSSs, as demonstrated by FIG. 4B, allows its recognition as a substrate of RAG-mediated targeted insertion into the endogenous TCR/Antibody chain locus, but only if the vector transduces appropriate lymphocyte precursors, in which RAG is active. Recombination events involving the two flanking RSSs may be sequential rather than parallel, much as chromosomal D to J recombination naturally precedes V to DJ recombination. The identity of the endogenous chain being targeted depends on the lymphocyte precursor being transduced and on the RSS pair being used. The targeted cassette includes a sequence upstream to the receptor/Antibody gene which codes a 2A peptide or an IRES in order to avoid formation of protein fusions with preceding segments while still utilizing the strong endogenous promoter. A splice donor (SD) may further be provided downstream of the receptor/Antibody gene to facilitate utilization of the endogenous C segment(s) upon integration, transcription and splicing. More specifically, the SD is required to allow class switching of targeted Antibodies. In particular, an Antibody targeting cassette entails: RSS-2A/IRES-$V_L J_L C_L$-2A-$V_H D_H J_H$-SD-RSS, or alternatively encodes a single chain variable fragment or a bi-specific or tri-specific antibody.

A TCR targeting cassette entails: RSS-2A/IRES-VαJαCα-2A-VβDβJβ-SD-RSS, or alternatively encodes a TCRγδ.

A CAR targeting cassette entails RSS-2A/IRES-CAR-Stop-SD-RSS.

VDJ targeting relies on the ability of the RAG complex to act in trans, i.e. to recombine RSSs found on different molecules. Indeed, by its evolution, structure and mechanism of action, RAG is a DNA transposase. RAG was shown capable of inducing the transposition of DNA segments in trans both in vitro and in vivo. VDJ targeting further relies on rAAV transduction since rAAV is proficient in transducing many different tissues in vivo and several rAAV variants can efficiently transduce HSCs and lymphocytes [12].

Example 2

Vector Design
RSS Choice

VDJ targeting in accordance with the invention can be used to integrate desired transgenes in any TCR chain (α, β, γ or δ) or Antibody chain (heavy, κ or λ) and between different segments in any chain. The identity of the endogenous chain being targeted depends on the lymphocyte precursor being transduced and on the RSSs flanking the transgene cassette. An RSS is composed of a conserved nonamer and a conserved heptamer separated by a variable spacer. The length of the spacer is either 12 bp or 23 bp (sometimes 22). The "12/23 rule" dictates that RAG will recombine an RSS that has a 12 bp spacer only with an RSS that has a 23 bp spacer and vice versa. Specific sequence features may further cause a particular "12 RSS" to recombine more efficiently with some "23 RSSs" but not with others, and this may underlie the "beyond 12/23 rule" preventing VJ rearrangements (skipping D) in TCR β and δ chains. Therefore, in some embodiments, the transgene cassettes is flanked either by "same" RSSs (two 12 RSSs or two 23 RSSs), or by an incompatible pair of a 12 RSS and a 23 RSS.

According to some embodiments, in the specific vector configuration for VDJ targeting in the B lineage, a cassette flanked by two "outward facing" 12 RSSs is targeted to integrate between a V and a J segment of the heavy chain (FIG. 5A). In some further embodiments, the specific vector configuration for VDJ targeting in the T lineage, a cassette flanked by two "downstream facing" 23 RSSs is targeted to integrate between a D and a J segment of a β chain (FIG. 5B). The upstream 23 RSS on the vector is of the "V type" and the downstream 23 RSS on the vector is of the "D type", in order to preclude integration between two genomic J segments, according to the beyond 12/23 rule. Subsequent natural V to D rearrangement brings the V promoter to the proximity of the enhancer and allows robust cassette expression. It is possible to avoid the requirement for additional, naturally occurring V(D)J rearrangements by coding an enhancer or a promoter (but not both) as part of the cassette.

Importantly, RSS configuration is essential but not sufficient for desired targeting. VDJ targeting takes place only if a vector with the appropriate RSS configuration transduces the appropriate lymphocyte at the appropriate developmental stage, because genomic RSS accessibility is determined by developmentally regulated transcription and epigenetic factor. The first constructs described herein target the heavy chain locus in B cell and the β chain locus in T cells. When targeting in vitro differentiating lymphocytes, the targeting occurs early during development (Pro-B cells and DN1/2 cells respectively). Targeting between V and J segments or between D and J segments must be induced before the natural D to J rearrangement which precedes the V to DJ rearrangement in these cells. Targeted cells does not express a pre-BCR or pre-TCR, yet TCR/BCR transgenic mouse data imply that they nevertheless successfully pass all developmental checkpoints. In subsequent experiments, the rates and consequences of targeting the light chains in B cells and the α chain (and later γ or δ chains) in T cells are assessed. This requires targeting later during in vitro differentiation (when targeting in vitro) and using appropriately oriented 12 and 23 RSSs.

Inclusion of Constant Regions or Splice Donors

In a specific and non-limiting configuration for VDJ targeting in the B cell lineage, a heavy chain constant region is not encoded but instead a downstream splice donor (SD) is included to allow the utilization of endogenous constant region. The cassette encodes an Antibody light chain ($V_L J_L C_L$) and a variable region of a heavy chain ($V_H D_H J_H$) separated by a 2A peptide ($V_L J_L C$-2A-$V_H D_H J_H$-SD). Upon integration, transcription and splicing, the transgene is first expressed as a BCR on naïve B cells. Following antigen-induced activation and affinity maturation the transgene is also expressed as antibodies of different classes being secreted from plasma cells.

In the T cell lineage, two different specific configurations for VDJ targeting are used, specifically, TCR and CAR.

More specifically, when targeting a transgenic TCR cassette to the TCR β chain locus, a heavy chain constant region is not encoded but instead it includes a downstream splice donor (SD) to allow the utilization of endogenous constant region. The cassette encodes a TCR α chain ($V_α J_α C_α$) and a variable region of a β chain ($V_β D_β J_β$) separated by a 2A peptide ($V_α J_α C_α$-2A-$V_β D_β J_β$-SD). rAAV coding capacity is limited, and therefore omitting CB in favor of a SD is beneficial. In addition, without being bound by theory, it seems that the SD inclusion allows a more natural-like expression with increased RNA stability and subsequent translation.

When targeting a CAR cassette to the TCR β chain locus, the full CAR gene is encoded, ending with a stop codon, and only then a SD (additional variants include a synthetic polyadenylation site).

Inclusion of Minimal Promoters and/or Splice Acceptors

In a specific and non-limiting configuration for VDJ targeting in the B cell lineage, a splice acceptor (SA) or a minimal promoter (MP) may be included. The cassette encodes an Antibody light chain ($V_L J_L C_L$) and a variable region of a heavy chain ($V_H D_H J_H$) separated by a 2A peptide (SA-$V_L J_L$C-2A-$V_H D_H J_H$-SD). Upon integration, transcription and splicing, the transgene is first expressed as a BCR on naïve B cells. Following antigen-induced activation and affinity maturation the transgene is also expressed as antibodies of different classes being secreted from plasma cells. Similar example with a minimal promoter may be: MP-$V_L J_L$C-2A-$V_H D_H J_H$-SD. In the T cell lineage, two different specific configurations for VDJ targeting are used, specifically, TCR and CAR.

More specifically, when targeting a transgenic TCR cassette to the TCR β chain locus the cassette may further include an upstream splice acceptor (SA). The cassette encodes a TCR α chain ($V_\alpha J_\alpha C_\alpha$) and a variable region of a β chain ($V_\beta D_\beta J_\beta$) separated by a 2A peptide (SA-$V_\alpha J_\alpha C_\alpha$-2A-$V_\beta D_\beta J_\beta$-SD). Similar embodiments using a minimal promoter may include (MP-$V_\alpha J_\alpha C_\alpha$-2A-$V_\beta D_\beta J_\beta$-SD). In some embodiments, the splice acceptor (SA) may be SA 97.66 having the nucleic acid sequence as denoted by SEQ ID NO: 26. In some embodiments, the splice acceptor (SA) may be SA EF1a having the nucleic acid sequence as denoted by SEQ ID NO: 31. In some embodiments, the splice donor (SD) may be SD mIGHJ1/J4 having the nucleic acid sequence as denoted by SEQ ID NO: 32. In some embodiments, the splice donor (SD) may be SD IgHJ3 SD 98.84 having the nucleic acid sequence as denoted by SEQ ID NO: 33.

In some embodiment, the minimal promoter may be a Variant of IGH minimal promoter having the nucleic acid sequence as denoted by SEQ ID NO: 34. In some embodiment, the minimal promoter may be an IgK Minimal Promoter having the nucleic acid sequence as denoted by SEQ ID NO: 35.

IRES/2A Coding Sequences

In some embodiments, the targeted cassettes include a sequence upstream to the receptor/Antibody gene which codes a 2A peptide or an IRES in order to avoid formation of protein fusions with preceding segments while still utilizing the strong endogenous promoter. In some embodiments, the IRES represents the first choice because subsequent expression is independent of junctional diversity introduced by terminal deoxynucleotidyl transferase (TDT) during RAG induced rearrangements. The IRES is preceded by a 3-frame stop to prevent ongoing translation. 2A peptides only induce ribosomal skipping if the reading frame is preserved (roughly ⅓ of events). Nevertheless, when active, 2A peptide can allow very high expression levels of an integrated transgene. Therefore, some of the vectors encode a 2A peptide to assess which design allows maximal expression. In addition, many of the vectors encode several peptides (e.g. two Antibody chains) and these are separated by 2A peptides. A non-limiting example of a vector design with a preceding IRES and an intervening 2A peptide may be: (RSS-IRES-$V_L J_L$C-2A-$V_H D_H J_H$-SD-RSS).

Inclusion of an Inducible Suicide Gene

Many immunotherapy targets are self-antigens, and therefore sustained autoimmunity from lymphocytes directed against these autoantigens is a serious problem for all lymphocyte engineering approaches, including for VDJ targeting described herein. The optimal vector configuration for facilitating VDJ targeting is evaluated by incorporation of an inducible suicide gene for the specific elimination of targeted lymphocytes (when expression is found to be associated with adverse outcomes). In particular, an upstream caspase gene fused to an inducible dimerization domain (iCasp9) is added to the cassette. The default is the expression of an inactive monomeric caspase. However, if an adverse outcome is seen and quick shutoff is desired, the addition of a small membrane permeable molecule allows the dimerization of the caspase and the subsequent induction of apoptosis. Importantly, similar systems are successfully used for the elimination of genetically modified T cells in multiple ongoing clinical trials (e.g. NCT01875237). Apoptosis induced by caspase dimerization is independent on cell cycling, it is quick, non-immunogenic and has little bystander effect compared to common alternatives for induced cell death. An example of a vector design with an inducible suicide gene is: (RSS-IRES-iCasp9-2A-$V_L J_L$C-2A-$V_H D_H$JH-SD-RSS).

Inclusion of miRNAs

The optimal vector configuration for facilitating VDJ targeting is evaluated followed by testing designs incorporating one of several alternative and non-mutually exclusive miRNAs:

a) miRNA against non-targeted chains, e.g. in order to target a full TCR gene (TCRα-2A-TCRβ) into the TCRβ chain locus, miRNA against the TCRα chain is used to prevent cross-dimerization.

b) miRNAs against the non-targeted allele; knockdown of the other allele is desired only if natural allelic exclusion is absent or incomplete, for example when introducing a CAR gene rather than a TCR and thus not providing all natural signals for allelic exclusion.

c) miRNA against the immune checkpoint protein PD1 in T cells; this prevents tumor tolerance but may also increase the risk of adverse autoimmunity and therefore it is used in conjunction to an inducible suicide gene as described above.

d) miRNA against an apoptotic gene; this may prevent central tolerance by negative selection if targeting an autoantigen but it also increases risk of sustained adverse autoimmunity and therefore it is used in conjunction to an inducible suicide gene as described above.

Importantly, the miRNA does not require a vector borne promoter but instead can be efficiently processed from an intron upon transgene integration and transcription. An example of a vector design with a miRNA and an inducible suicide gene is: (RSS-IRES-iCasp9-2A-$V_L J_L$C-2A-$V_H D_H J_H$-SD-miRNA-RSS).

rAAV Capsid and Genome

Several rAAV serotypes can efficiently transduce HSCs and lymphocytes. The rAAV6 serotype is used for most in vitro VDJ targeting assays, because it is the most widely used serotype in lymphocytes to date [12]. However, additional serotypes are also tested including HSC derived AAV and rAAV8 that was found efficient, and superior to lentivectors, at in vivo intrathymic transfection in both mice and macaques [16]. The transgene cassettes is encoded in self-complementary rAAV (scAAV), which allows the RSSs to quickly obtain the dsDNA configuration that is recognized by RAG. ScAAV coding capacity is just over 2 Kb. Therefore, for targeting of longer genes or several genes (e.g. when introducing an inducible suicide gene), the cassettes are encoded in single stranded AAV (ssAAV). ssAAV is processed in the target cell into dsDNA forms but with delay and efficiency loss compared to scAAV.

Example 3

Developing VDJ Targeting of Ex Vivo Differentiating Lymphocytes

Assays in Readily Transfected Cell Lines

VDJ targeting is first demonstrated in episomal and integrated reporter systems in readily transfected cell lines, as illustrated by FIG. 6. Activity of the transgenic RAG in the cell lines is verified using a reporter system where RAG induced recombination in cis leads to GFP expression (FIG. 6A). VDJ targeting is then demonstrated using a donor vector coding for an RSS-flanked promoterless GFP and an either episomal or integrated reporter coding for RFP flanked by RSSs which are compatible with the donor RSSs (FIG. 6B). VDJ targeting rates is normalized to transfection efficiency (measured using a canonical GFP expression vector) and to RAG activity and compared to a negative control where the RAG expressing plasmids are not co-transfected. Analogous reporter system is used in human cell lines (typically HEK293) and mouse cell lines (typically NIH3T3). The appropriate human or mouse RAG proteins is expressed in each system. RSS sequences are chosen that are highly used in natural V(D)J recombination in developing T cells or B cells in the respective organism. Different donor and reporter plasmids encode different RSS sequences at different relative orientations to assess compatibility and maximize efficiency. Several RSS choice are tested for their ability to help in targeting integration to one chain but not another chain (e.g. to the β and not δ chain), and also to one pair of segments and not another pair (e.g. target integration between D and J and not between two different J segments). Episomal assays (co-transfection of donor and reporter) is used for quick initial readout, but ultimately, selected cell clones harboring a single integrated reporter provide a clearer result (targeted cells are not only green, they are also not red).

Examples of integrated reporter systems transfected in HEK293 cell lines are provided in FIG. 7 and FIG. 8. VDJ targeting of a single-RSS construct containing dsRED reporter gene, was performed toward the IgK locus of HEK293T cells (FIG. 7A). PCR analysis demonstrated that upon co-transfection with plasmid encoding RAG1 and RAG2, the dsRED2 cassette was successfully incorporated between the V and J segments of the IgK locus (FIG. 7B).

VDJ targeting of a dual-RSS construct containing GFPi-redless reporter gene, was performed toward to the IgK locus in HEK293T cells (FIG. 8A). PCR analysis demonstrated that upon addition of plasmids encoding RAG1 and RAG2, the GFPi-redless cassette was successfully incorporated between the V and J segments of the IgK locus of T cells (FIG. 8B).

Assays in Transformed Lymphocyte Cell Lines:

Following, selected reporter vectors are then used to assess VDJ targeting rates in lymphocyte cell lines which express RAG either constitutively or inducibly. In particular, VDJ targeting is assessed in the Sup-T1 T-ALL cell line, which expresses RAG at a high basal level, and in V-Abl transformed pro-B cell lines (Lescale C et al., Nat Commun. 7:10529 (2016)) and Pre-B cells lines (Yin B, et al. J Exp Med. 206(12):2625-2639(2009)), which express RAG upon induction by the V-Abl kinase inhibitor. In these cells, the RSS compatibility is examined in the lymphocyte setting, and in addition, the effect of different delivery methods on the rates of VDJ targeting is compared. In particular, VDJ targeting rates after co-delivery of the same donor and reporter pair using either plasmid electroporation (Neon™), lentiviral vectors or rAAV vectors are compared, where each rate is normalized to transduction rates of a GFP positive control using the respective delivery method. For rAAV vectors, VDJ targeting propensity of self-complementary AAV (scAAV) and single stranded AAV (ssAAV) and of serotypes rAAV6 and rAAV8 are compared as well as HSC derived rAAV.

An example of VDJ targeting into inducibly differentiating B cells is provided in FIG. 9. V-Abl immortalized murine Pro B cells were transfected with the GFPi-redless plasmid containing a 23-consensus RSS and a 12-consensus RSS. Cells further received Imatinib for induction of differentiation as schematically represented in FIG. 9A. PCR analysis demonstrated that upon addition of the plasmid encoding GFPi-redless, the GFPi-redless cassette was successfully incorporated between the V and J segments of the IgK locus of differentiating B cells (FIG. 9B).

In addition, a gene coding for an antibody was integrated by VDJ targeting into the IgK locus of inducibly differentiating B cell progenitors. The inventors used a cell line of immortalized pro-B cells that can be induced to differentiate and express RAG upon administration of the v-Abl kinase inhibitor Imatinib. Electroporation was performed using a plasmid coding for the anti-RSV antibody Palivizumab flanked by appropriate RSSs (see illustration in FIG. 10). Analysis by Reverse transcription reaction (see more details in the Experimental procedure section) shows that integration into the IgK locus and subsequent expression occurred only upon addition of Imatinib (see FIG. 11).

Reporter Assays in In Vitro Differentiating Primary Cells

Next, the rates of VDJ targeting is assessed in primary developing lymphocytes in vitro. Initially, GFP coding donor vectors are used, as GFP allows an easily quantifiable readout and is highly suitable for protocol optimization. However, follow-up experiments, targeting receptor genes (TCR/CAR/BCR), may reveal interesting discrepancies with the GFP experiments because receptor presentation is known to affect subsequent lymphocyte differentiation. Therefore, some of the vectors target both a GFP marker and a receptor (detailed below), separated by a 2A peptide. VDJ targeting rates are assessed in lymphocytes differentiated from three diverse pluripotent cell sources: mouse Embryonic Stem Cells (Kucerova-Levisohn M, et al., J Vis Exp. (92):e52119.(2014)), mouse Hematopoietic Stem cell (HSCs), and human Umbilical Cord Blood Hematopoietic Stem cells (UCB HSCs) [7]. The vectors for transfection of mouse and human cells codes the respective RSS sequences and have appropriate codon usage optimization.

In the T cell lineage, RAG is naturally expressed during the maturation of double negative 1 (DN1 through ISP) thymocytes, and in the B cell lineage, it is expressed during differentiation from Pro-B cell to immature B cell. In vitro, pluripotent cells are differentiated to T-cell on a support of OP9-DL1 cells providing Notch differentiation signals, and pluripotent cells are differentiated to B cells on a mesenchymal stem cell-conditioned medium containing SCF, G-CSF, FLT3 ligand, and IL-7. Precursors of different stages are transfected with an rAAV6 or rAAV8 vector coding for a GFP gene flanked by RSSs. Subsequently, additional differentiation is facilitated to allow for RAG expression and VDJ targeting. Real time PCR and flow cytometry are both used to assess the targeting rate. For each type of differentiating culture, the composition and differentiation status of the culture are assessed daily by flow cytometry. rAAV transfections are performed at different days opting to find the timing that allows the highest rates of VDJ targeting. The first transfection time point in the T lineage is when the proportion of double negative 1 (DN1) cells is peaking, per flow cytometry (allowing for DJ recombination at the β TCR locus). The last transfection time point in the T lineage is when the proportion of ISP cells is peaking (allowing for VJ recombination at the α TCR locus). The first transfection time point in the B lineage is when the proportion of pro-B cells is peaking, per flow cytometry (allowing for DJ recombination at the heavy chain locus). The last transfection time point in the B lineage is when the proportion of immature B cells is peaking (allowing for VJ recombination at a light chain locus). For both lineages, the optimal transfection time point is evaluated followed by examination of the efficacy of different MOIs (1E9 vg/mL through 1E11 vg/mL) and construction of a dose response curve.

Targeting In Vitro Differentiating B Cells from IL7R+ Enriched Primary Bone Marrow Using AAV IL 7R positive cells in the bone marrow correspond to B-cell progenitors on the verge of V(D)J recombination as described in FIG. 12. Bone marrow were thus extracted from mice. Enrichment for IL7R positive cells was then performed, in vitro differentiation was facilitated and the cells were transduced with an AAV vector coding for a VDJ-targeting construct, the dsAAV 360-A viral vector (the bacterial plasmid used in the preparation of the AAV vector, see more details in the Experimental procedure section). The resulting products were analyzed by RT-PCR, cloned into bacterial plasmids and subjected to Sanger sequencing as detailed in the Experimental procedure section.

More specifically, for VDJ targeting of B cell progenitors, IL7R cells were enriched. It appears that IL7R+ enriched bone marrow cells exhibited a marked increase in purity. Typical IL7R enrichment was about of 20-30 fold (see FIG. 13A-13C (i-iv)). As shown in FIG. 14, following isolation, ~60% of the cells expressing the IL7 receptor also express the CD19 B-cell marker. Within 3 days of culture, IL7 receptor-positive enriched lymphocytes exhibit a dramatic increase of differentiation rate, as exhibited by expression of both IgM and IgK while IgM precedes IgK (FIG. 15). IL7R-enriched bone marrow cells were than transduced with the dsAAV 360-A viral vector as described in experimental procedures. Trans-recombination products were detected in transduced cells by Reverse Transcription followed by two rounds of PCR (see FIG. 16A, 16B, 16C). Sanger sequencing of two separate clones was performed and showed junctional diversity at the coding joint, a unique attribute of RAG mediated integration. The two coding joints map to IgK-J4 and IgK-J5 are illustrated in FIG. 17A-17B. These results illustrate successful V(D)J targeting of an immunoglobulin light chain segment in primary B cells.

Receptor/Antibody Targeting in In Vitro Differentiating Primary Cells

The optimal parameters of VDJ targeting are evaluated using the GFP construct in in vitro differentiating T cells and the protocol is subsequently applied to the integration of several different receptors of clinical relevance.

The following receptors are targeted:
a) an anti CD19 CAR coding construct, shown to be highly effective in treating B cell malignancies;
b) an anti-Tn-MUC1 CAR coding construct which targets a highly cancer specific glycoform; and
c) an NY-ESO-1-specific TCR construct. NY-ESO-1 is a cancer-testis antigen and early clinical data with the TCR concordantly shows good safety and efficacy profiles (Rapoport A P, et al. Nat Med. 21(8):914-921 (2015)).

Targeted receptors were chosen to maximize the therapeutic impact while minimizing the risk of sustained auto-immunity. Nevertheless, the risk remains and is subsequently mitigated by the introduction of inducible suicide genes. Targeting rates are validated using RT-PCR and flow cytometry. Flow cytometry is further used to determine the subclass distribution among the targeted T cells upon maturation. This is followed by in vitro functional assays, including: chromium release from labeled CD19/Tn-MUC1/NY-ESO-1-expressing cells as well as a cytokine release assay (Kunkele A, et al. Cancer Immunol Res. 3(4):368-379 (2015)). In addition, where available, the inventors demonstrate that stimulated T cells that were targeted while differentiating from HSCs obtained from cancer patients can lyse autologous Tumor cells.

Similarly, the optimal parameters of VDJ targeting are evaluated using the GFP construct in in vitro differentiating B cells and the protocol is subsequently applied to the integration of several different Antibodies of clinical relevance. The following antibodies are targeted:
(a) 3BNC117 an anti-HIV Antibody showing remarkable clinical efficacy (Scheid J F, et al. Nature. 535(7613): 556-560 (2016)); (b) Adalimumab (Humira™) an anti-TNFα Antibody that is effective in many auto-immune diseases but is associated with a high cost and high incidence of anti-drug antibody formation (Bartelds G M, et al., JAMA. 305(14):1460-1468 (2011)); and
(c) PankoMab-GEX an anti MUC1 glycoform Antibody that is highly cancer specific and has a good safety profile according to recent clinical trials (Fiedler W, et al. Eur J Cancer. 63:55-63 (2016)). Targeting rates are validated using RT-PCR and flow cytometry. Flow cytometry is further used to determine the subclass distribution among the targeted B cells upon maturation. This is followed by in vitro B cell activation assay.

In both lineages, LAM PCR is used followed by next generation sequencing to assess off-target integration profile, and karyotyping is used to detect chromosomal aberrations.

Adoptive Therapy with Targeted Cells in Animal Models:

Well established mouse models are used to assess the in vivo potency and safety of selected in vitro targeted and differentiated cells. Efficacy of Anti-CD19 CAR targeted T cells is tested in the Raji Burkitt lymphoma bearing SCID-beige model, following CD80 and IL15 co-stimulation (Brentjens R J, et al. Nat Med. 9(3):279-286 (2003)). In particular, selective expansion of targeted cells leading to subsequent drop in CD19 counts and eradication of Raji tumors are evaluated in these mice. Efficacy of B cells targeted with anti-TNFα Antibody is also evaluated in a human TNFα over-expressing transgenic mouse. These TgTC mice develop a progressively erosive polyarthritis developed with many characteristics of human rheumatoid arthritis, including polyarticular swelling, impairment of movement, cartilage and bone erosion and synovial hyperplasia. Following adoptive transfer of targeted B cells, repertoire sequencing is used in order to monitor selective expansion and affinity maturation (somatic hypermutations as well as class switching) and to prevent arthritis in this mouse model.

Safety assessment is paramount in the in vivo experiments. For all in vivo studies, mice weight, appearance and behavior as well as assess plasma levels of AST enzymes, as markers of tissue toxicity are monitored and scored. A multiplex bead-based cytokine assay is also applied because cytokine storm is a common adverse effect of cancer immunotherapy. LAM PCR is performed for off-target integration analysis using plasma derived T-cells and post-mortem thymocytes. Finally, some mice are transplanted with targeted lymphocytes early in life and kept alive for 18 subsequent months to allow long term carcinogenicity assessment.

Example 4

Developing VDJ Targeting by In Vivo Vector Administration

Ex vivo engineering of lymphocytes and pluripotent cells is cumbersome, time consuming and expensive. VDJ targeting following in vivo rAAV injection allows scaling up and applying the treatment to a much wider population. Importantly, rAAV vectors have a better safety profile than lentiviral and retroviral vectors, commonly used for T cell engineering to date. rAAV vectors are also superior to lentivectors in the transduction of thymocytes in vivo. The rAAV constructs for in vivo assessment of VDJ targeting is similar to those used for in vitro assessment, using rAAV6 and HSC derived rAAV, as well as the rAAV8 serotype that was previously shown to be efficient in intrathymic transfection.

As described herein before, for safety validation, mice weight, appearance and behavior as well as assessment of plasma levels of AST enzymes, as markers of tissue toxicity are monitored and scored. LAM PCR is performed for off-target integration analysis using plasma derived T-cells and post-mortem thymocytes, and some mice are injected early in life and kept alive for 18 subsequent months to allow long term carcinogenicity assessment.

Intrathymic rAAV Injections

Intrathymic injections are most clinically relevant at an early age, prior to thymic involution. However, in humans, thymopoiesis may continue at least until age 40. T cells develop in thymus, thus, thymic injections may allow transduction of T cells progenitors undergoing VDJ recombination. Alternatively, in vitro differentiated T cell precursors may be transduced. The cells may then be infused either into the thymus or systemically and thymic migration and retention is then monitored.

Transfection Positive Control

First, injections were performed to demonstrate the feasibility of cell injection into the thymus of a live animal. Then, luciferase-transduced cells were used to show that cell retention may be monitored by following a luciferase signal (see details in the Experimental procedure section). It appears that Jurkat cells stained with CFSE and injected intrathymically using ultrasound guidance in live mice were readily detected in mouse thymuses after post-mortem surgery (see FIG. 18A-18C).

Next, fresh murine bone marrow cells, with or without enrichment for Lin– cells, were transduced with a retroviral vector encoding for luciferase and injected intrathymically using ultrasound guidance in live mice. Luciferase signal was readily detected in the thymuses of live mice following luciferin administration (see FIG. 19A-19C).

In a next step, doses of 1E11 to 1E12 rAAV vectors are injected directly into the thymus of 4-8 weeks-old mice. Canonical, promoter-driven, GFP-coding constructs are injected as a positive control, and transfection rates are estimated using RT-PCR and flow cytometry. Based on Moreau et al. [16], by day 3 post-transfection, rates of GFP+ cells are assessed among all thymocyte populations as well as epithelial cells and dendritic cells. The percentages of transduced thymocytes within the DN (CD4–CD8–), DP (CD4+CD8+), and SP mature (CD4+CD8– and CD4–CD8+) subsets reflect their overall thymic distribution, as expected. Monitoring rates of GFP+DP cells at day 10 post-transfection, an increase subsequent to differentiation of immature transduced progenitors is demonstrated as expected, however, DN transduced thymocytes are still detected at significant rates at days 10 and 30 post-injection. The migration of differentiated targeted cells is further examined into the periphery. In particular, flow cytometry and RT-PCR are used to estimate rates of targeted cells in the spleen and in the lymph nodes at days 3, 10 and 30 post-transfection. At day 3 post-transfection, only low rates of targeted T cells in the lymph nodes and the spleen are expected but the rate may increase to as much as 1% by day 10, for the lowest injected dose (1E11). The rate then declines significantly by day 30 post-injection as these mice have a full lymphocyte compartment and due to episomal vector dilution in dividing cells an in the absence of selective advantage. With intrathymic injections, little to none transduced CD19+ B cells is expected and as well as no skewing of the CD4/CD8 ratio, (expected to be 3:2 in both the eGFP– and eGFP+ subsets). Differentiated targeted cell has a naïve T cell phenotype (CD44low/CD62Lhigh) since rAAV transduction does not activate T lymphocytes leading to acquisition of an effector or memory phenotype.

RAG Activity Assay

The experiments above are then repeated using a RAG activity reporter vector, where RAG induced recombination in cis leads to GFP expression (as illustrated in FIG. 6A). With this vector, only cells transfected as DN to ISP thymocytes initially show GFP expression as expected. The distribution of GFP+ cells within the DN subpopulations, DN1 to DN4, serves as a predictor for subsequent VDJ targeting experiments (below). Again, by day 10 post-transfection, the percentage of DP thymocytes increases subsequent to differentiation of immature transduced progenitors, however, DN transduced thymocytes are still detected at significant rates at days 10 and 30 post-injection as expected. When analyzing the migration of differentiated targeted cells to the spleen and lymph nodes, only low rates of targeted T cells are expected at day 3, but the rate may increase by day 10, and subsequently decline by day 30 post-injection due to episomal vector dilution in dividing cells and in the absence of selective advantage. The absence of transduced CD19+ B cells and a normal CD4/CD8 ratio is further validated as well as differentiated targeted cells having a naïve T cell phenotype (CD44low/CD62Lhigh).

VDJ Targeting Reporter Assay

Next, the experiments above are repeated using a GFP reporter of VDJ targeting in the T lineage. The initial distribution of GFP+ cells reflects the integration accessibility of the integration locus. In particular, when using a vector for VDJ targeting between D and J of TCRβ (similar to the one in FIG. 4B, but with a GFP gene instead of a receptor gene) initial GFP+ cells appear among DN2 thymocytes. When using a vector for VDJ targeting between V and J segments of the TCRα locus, initial GFP+ cells are observed among DP thymocytes, and when using a vector for VDJ targeting into the TCRγ or the TCRδ locus, initial GFP+ cells are observed among DN4 thymocytes. As GFP is stably integrated into the genome, it is expected to observe expression in all subsets of thymocytes and mature T cells which are later in the developmental path than the precursor where integration was facilitated. In particular, in all cases, a high increase of GFP+DP and SP (CD4+ or CD8+) with time, is expected and finding activated GFP+ T cells acquiring effector or memory phenotypes as also expected. However, GFP+ rates at all subpopulations are still expected to be low in the absence of a selective advantage or specific activation.

VDJ Targeting of Receptor Genes

Finally, targeting of receptor genes is evaluated. All constructs include an inducible suicide gene (iCasp9, Di Stasi A, et al. The New England journal of medicine 365(18):1673-1683 (2011)) to specifically and quickly eliminate the targeted cells if adverse events occur. One vector encodes a human Tn-Muc1 specific TCR construct and is injected intrathymically to conditional mouse model of human MUC1-positive endometriosis. Targeted T cell precursors pass not only positive about also negative thymic selection as expected. Expression levels in thymocyte subclasses and in T cells are examined using RT-PCR and flow cytometry. Here, TCR expressing T cells are expected to be activated upon interaction with the human MUC1 tumors, and subsequently it is expected to see eradication of the tumors by pathology and immunohistochemistry.

Yet another construct encodes an anti-mouse-CD19 CAR. CAR vectors is designed to allow integration between the D and J segment of the TCRβ locus. This allows early targeting, and assuming a CAR does not provide signals for allelic exclusion, the other allele is rearranged to provide an MHC interacting TCR in order to pass through positive thymic selection. The construct also encodes a miR-181a recognition element. In some particular and non-limiting embodiments, VDJ targeting in accordance with the invention may be employed to target the miR-181a recognition element that comprises the nucleic acid sequence as denoted by SEQ ID NO. 18. miR-181a is strongly expressed in thymocytes and markedly downregulated in post-thymic T cells (Papapetrou E P, et al., J Clin Invest 119(1): 157-168 (2009)). In particular, the auto-reactive receptor is not expressed in thymocytes subjected to negative selection but expression ensues upon maturation. As described herein before, expression levels in thymocyte subclasses and in T cells are examined using RT-PCR and flow cytometry. Here, CAR expressing T cells are expected to be activated by the CD19 B cell antigen, leading to expansion of the targeted T cell population concomitant to elimination of natural B cells. Conversely, upon administration of the Caspase9 dimerization inducers, the targeted T cells are expected to be eliminated and the B cell compartment to be re-established through differentiation of HSCs.

Intravenous rAAV Injections after Stem Cell Mobilization

It was previously shown that mobilized HSPCs can be targeted in vivo at high rates and subsequently home back to the bone marrow where they stably express the transgene [17]. Moreover, long term surviving HSPCs can be transduced and expanded in the marrow. However, previous approaches used immunogenic adenovectors and genotoxic, promiscuously integrating transposons. Here, in vivo VDJ targeting is demonstrated after tail vein vector injections following bone marrow mobilization, without relying on myeloablative conditioning. Subcutaneous injections of G-CSF/AMD3100 is used to mobilize HSPCs from the bone marrow into the peripheral blood stream. Upon mobilization (followed by flow cytometry), tail vein injections of 1E11 to 1E12 rAAV vectors of serotypes 6, 8 and HSC derived rAAV are performed.

Transfection Positive Control

First, canonical, promoter-driven, GFP-coding constructs are injected as a positive control, and transfection rates are estimated using RT-PCR and flow cytometry. GFP+ cells are expected among HSCs and many classes of their derived lineages. When comparing different serotypes one can determine which one allows the best transfection of B cell precursors (Pro-B, Pre-B and immature B). In lack of integration and selective advantage, the rate of GFP+ mature B cells is expected to have a naïve phenotype and their rate to rise initially but then soon decline. Homing of transduced cells back to the bone marrow is validated.

RAG Activity Assay

Next, the experiments above are repeated using a RAG activity reporter vector, where RAG induced recombination in cis leads to GFP expression (FIG. 6A). With this vector, only cells transfected as pre-B cells to immature B cells show GFP expression. The distribution of GFP+ cells within the precursor subpopulations serves as a predictor for subsequent VDJ targeting experiments (below). Again, the percentage of mature B cells increases following differentiation of immature transduced progenitors, however, GFP+ precursors are still detected at significant rates. The rate if GFP+ B cells then declines due to episomal vector dilution in dividing cells and in the absence of selective advantage. Differentiated targeted cells are again validated for having a naïve phenotype.

VDJ Targeting Reporter Assay:

Next, the experiments above are repeated using a GFP reporter of VDJ targeting in the B lineage. The initial distribution of GFP+ cells reflects the integration accessibility of the integration locus. In particular, when using a vector for VDJ targeting between V and J of the heavy chain (FIG. 5A, but with a GFP gene instead of an Antibody gene), initial GFP+ cells are observed among pre-B precursors. When using a vector for VDJ targeting between V and J segments of light chain locus, initial GFP+ cells are expected among immature B cells. As GFP is stably integrated into the genome, expression is observed in all subsets of the B cells lineage and mature B cells which are later in the developmental path than the precursor where integration was facilitated. In all cases, a high increase of GFP+ immature and mature B cells is expected with time, as well as activated GFP+ B cells and plasma cells acquiring effector or memory phenotypes. However, GFP+ rates at all subpopulations are still expected to be low in the absence of a selective advantage or specific activation.

VDJ Targeting of Antibody Genes

Finally, targeting of Antibody genes is demonstrated. All constructs include an inducible suicide gene (iCasp9) to specifically and quickly eliminating the targeted cells if adverse events occur. The vector encodes PankoMab-GEX, an anti MUC1 glycoform Antibody that is highly cancer specific, and is injected intravenously to conditional mouse model of human MUC1-positive endometriosis. Targeted B cell precursors pass not only positive about also negative selection in the marrow as expected. Expression levels in B cell precursor subclasses and in mature B cells are assessed using RT-PCR and flow cytometry. Here, BCR expressing B cells are activated upon interaction with the human MUC1 tumours. Repertoire sequencing is used to monitor selective expansion and affinity maturation (somatic hypermutations as well as class switching) and subsequent eradication of the tumours is evaluated by pathology and immunohistochemistry.

Alternatively, when the mouse cancer does not express the human MUC1 glycoform that is targeted by the PankoMab- GEX Antibody, another vector is used, coding for the c-SN6j Antibody (anti-CD105). The vector is injected intravenously to a transgenic mouse model expressing relevant human CD105 epitopes on the vasculature of tumours induced by injections of 4T1 cells.

Confronting Positive Selection

Developing T cells targeted with a transgenic TCR are positively selected in the thymus, and developing B cells targeted with a transgenic Antibody express a BCR and thus are positively selected in the bone marrow. This is true whether the lymphocytes are targeted ex vivo and subsequently transplanted or whether targeting is achieved by direct in vivo injection of the vector. However, developing T cells targeted with a CAR gene and developing B cells targeted with scFv/BiTE pass positive selection, only if allelic exclusion is absent or incomplete in the case CARs and scFv/BiTEs do not provide all the natural ques for allelic exclusion.

Alternatively, when allelic exclusion is nevertheless found to be complete, then VDJ targeting of CAR and scFv/BiTE genes is accomplished by transduction of ex vivo differentiating precursors. Targeted cells further differentiated ex vivo pass the positive selection checkpoint prior to administration.

Confronting Negative Selection and Peripheral Tolerance

First, T cells and B cells are targeted with respective receptors and Antibodies against foreign antigens or neoantigen. Thus, the developing lymphocytes pass thymic negative selection. However, VDJ targeting can be used to engineer lymphocytes against the many common immunotherapy targets that are self-expressed antigens. When expressing a CAR/TCR against an auto-antigen, a miR-181a recognition element is incorporated into the cassette. miR-181a is highly expressed in developing T cells and markedly downregulated in post-thymic T cells. Inclusion of miR-181a recognition element can thus segregate expression of CARs and TCRs between developing and mature T cells. In particular, the auto-reactive receptor is not expressed in thymocytes subjected to negative selection but its expression is re-constituted upon maturation.

Efficacy against the desired auto-antigen comes also with the risk of sustained adverse auto-immunity. Therefore, when targeting a receptor against an autoantigen along with a miR-181a recognition element, an inducible suicide gene is also included, to allow specific elimination of targeted cells. Finally, when applying VDJ targeting to ex vivo differentiating cells, cells can be differentiated past the negative selection checkpoint before being injected, and co-delivering an inducible suicide gene is again preferable.

Example 5

Engineering Inducible B Cells

Many monoclonal Antibodies in clinical use are targeting self-antigens. However, monoclonal Antibodies have a limited half-life, requiring repeat administration at an extremely high cost. They are prone to anti-drug Antibodies and are rarely curative. In order to engineer B cells targeting self-antigens, it is not enough to bypass central tolerance. A B cell will not be activated by an auto-antigen even if the B cell expresses a relevant BCR, because the B cell will not get the necessary help from T cells at the germinal centre. Therefore, VDJ targeting application is specifically tailored to allow safe engineering of B cells to inducibly express autoantibodies. The design as schematically represented in FIG. 20, allows targeted developing B cells to pass positive and negative selection in the bone marrow and it allows B cell activation and secretion of the autoantibody only upon induction by a foreign inducer.

The inventors target the integration of a cassette separately coding for a secreted Antibody and a BCR targeting different antigens. The secreted Antibody is directed against a disease associated Auto-antigen, while the BCR is directed against a foreign inducer. The B cell differentiates to Antibody-secreting plasma cells only upon administration of the foreign inducer. The secreted Antibody is specifically a scFv or a BiTE, rather than a full IgL-2A-IgH Antibody, in order to prevent cross pairing with the BCR chains. The BCR gene is coded in a way that prevents its secretion by avoiding the alternative splice and polyadenylation sites that are used in the natural setting for exclusion of the transmembrane domain upon activation. The foreign inducer of BCR activation is specifically an antigen of an orally administered vaccine. A prominent example is the Polio vaccine, a safe, cheap, orally administered immunogen, that is rarely encountered through the natural life course, thus diminishing the risk of spurious activation. An appropriate BCR to be activated by the polio vaccine can be designed based on well characterized human anti-poliovirus antibodies [18]. Activation is dose dependent and self-limiting thus minimizing the risk of sustained adverse auto-immunity, while allowing oral re-dosing at will. In addition, immune memory from first activation increases the potency and shorten the kinetics of subsequent activations. In different patients, different auto-antigens can be targeted for the treatment of diverse clinical indications, but the inducer can be one and the same. From the protein therapy perspective: dozens of different monoclonal antibodies are replaced by a single orally administered immunogen. Inducible efficacy of targeted B cells may be demonstrated in immunocompetent C57BL/6 mice transplanted with a syngeneic B16F10/human-Ep-CAM cells as a subcutaneous solid tumour model.

Tumor Eradication by In Vitro Engineered Inducible-B Cells

First, VDJ targeting is performed in in vitro differentiating mouse B cells. The integrated cassette express an anti-human-Ep-CAM BiTE that is also specific to the mouse CD3 for mouse T cell engagement. In particular, VDJ targeting is used to introduce a cassette encoding for an anti-human-EpCAM BiTE and a BCR based on a human anti-polio Antibody [18]. RT-PCR is used to assess targeting rates in the different precursor subpopulations and among mature B cells, as well as flow cytometry with staining against human IgM to monitor BCR expression and presentation. ELISA is used to detect the BiTE before and after in vitro activation, to validate inducer dependent antibody secretion.

Next, the targeted B cells are implanted in C57BL/6 mice bearing syngeneic B16F10/human-Ep-CAM tumours, and in control tumour-free mice. Plasma BiTE levels are monitored by ELISA and are expected to be low in both groups, because activation relies on a polio immunogen. The Polio vaccine inducer is then orally administered and BiTE pharmacokinetics is examined by EILSA as well as dose dependent effects on tumour progression and eradication. ELISA monitoring is continued in order to assess the self-limiting nature of the induced activation, and repeat dosing are also performed to monitor how immune memory may allow faster and more potent reaction at second administration.

Tumour Eradication by In Vivo Engineered Inducible-B Cells in vivo VDJ targeting is applied for inducible-B cell engineering after tail vein vector injections following bone marrow mobilization, without relying on myeloablative conditioning. Subcutaneous injections of G-CSF/AMD3100 are used to mobilize HSPCs from the bone marrow into the peripheral blood stream. Upon mobilization (followed by flow cytometry), tail vein injections of 1E11 to 1E12 rAAV vectors (of serotypes 6, 8 and HSC derived rAAV) are provided. The integrated cassette again encodes an anti-human-EpCAM BiTE and a BCR based on a human anti-polio Antibody [18]. The presence of mature B cells expressing human IgM, monitored by flow cytometry, attests that the targeted precursors have homed back to the bone marrow and differentiated, passing both positive and negative selection. As described above, plasma BiTE levels are monitored by ELISA and are expected to be low, because activation relies on a polio immunogen. The Polio vaccine inducer is then administered orally, and BiTE pharmacokinetics are analysed by ELISA as well as dose dependent effects on tumour progression and eradication. ELISA monitoring is continued in order to validate self-limiting activation, and repeat dosing is also performed for monitoring how immune memory may allow faster and more potent reaction at second administration.

```
                          SEQUENCE LISTING

<160> NUMBER OF SEQ ID NOS: 51

<210> SEQ ID NO 1
<211> LENGTH: 931
<212> TYPE: PRT
<213> ORGANISM: Homo sapiens
<220> FEATURE:
<221> NAME/KEY: MISC_FEATURE
<223> OTHER INFORMATION: RAG-1 Accession number: AAH37344.1

<400> SEQUENCE: 1

Met Ala Ala Ser Phe Pro Pro Thr Leu Gly Leu Ser Ser Ala Pro Asp
1               5                   10                  15

Glu Ile Gln His Pro His Ile Lys Phe Ser Glu Trp Lys Phe Lys Leu
            20                  25                  30

Phe Arg Val Arg Ser Phe Glu Lys Thr Pro Glu Glu Ala Gln Lys Glu
        35                  40                  45

Lys Lys Asp Ser Phe Glu Gly Lys Pro Ser Leu Glu Gln Ser Pro Ala
    50                  55                  60

Val Leu Asp Lys Ala Asp Gly Gln Lys Pro Val Pro Thr Gln Pro Leu
65                  70                  75                  80

Leu Lys Ala His Pro Lys Phe Ser Lys Lys Phe His Asp Asn Glu Lys
                85                  90                  95

Ala Arg Gly Lys Ala Ile His Gln Ala Asn Leu Arg His Leu Cys Arg
            100                 105                 110

Ile Cys Gly Asn Ser Phe Arg Ala Asp Glu His Asn Arg Arg Tyr Pro
        115                 120                 125

Val His Gly Pro Val Asp Gly Lys Thr Leu Gly Leu Leu Arg Lys Lys
    130                 135                 140

Glu Lys Arg Ala Thr Ser Trp Pro Asp Leu Ile Ala Lys Val Phe Arg
145                 150                 155                 160

Ile Asp Val Lys Ala Asp Val Asp Ser Ile His Pro Thr Glu Phe Cys
                165                 170                 175

His Asn Cys Trp Ser Ile Met His Arg Lys Phe Ser Ser Ala Pro Cys
            180                 185                 190

Glu Val Tyr Phe Pro Arg Asn Val Thr Met Glu Trp His Pro His Thr
        195                 200                 205

Pro Ser Cys Asp Ile Cys Asn Thr Ala Arg Arg Gly Leu Lys Arg Lys
    210                 215                 220

Ser Leu Gln Pro Asn Leu Gln Leu Ser Lys Lys Leu Lys Thr Val Leu
225                 230                 235                 240

Asp Gln Ala Arg Gln Ala Arg Gln Arg Lys Arg Ala Gln Ala Arg
                245                 250                 255

Ile Ser Ser Lys Asp Val Met Lys Lys Ile Ala Asn Cys Ser Lys Ile
            260                 265                 270

His Leu Ser Thr Lys Leu Leu Ala Val Asp Phe Pro Glu His Phe Val
```

-continued

```
            275                 280                 285
Lys Ser Ile Ser Cys Gln Ile Cys Glu His Ile Leu Ala Asp Pro Val
    290                 295                 300
Glu Thr Asn Cys Lys His Val Phe Cys Arg Val Cys Ile Leu Arg Cys
305                 310                 315                 320
Leu Lys Val Met Gly Ser Tyr Cys Pro Ser Cys Arg Tyr Pro Cys Phe
                325                 330                 335
Pro Thr Asp Leu Glu Ser Pro Val Lys Ser Phe Leu Ser Val Leu Asn
                340                 345                 350
Ser Leu Met Val Lys Cys Pro Ala Lys Glu Cys Asn Glu Glu Val Ser
                355                 360                 365
Leu Glu Lys Tyr Asn His His Ile Ser Ser His Lys Glu Ser Lys Glu
                370                 375                 380
Ile Phe Val His Ile Asn Lys Gly Gly Arg Pro Arg Gln His Leu Leu
385                 390                 395                 400
Ser Leu Thr Arg Arg Ala Gln Lys His Arg Leu Arg Glu Leu Lys Leu
                405                 410                 415
Gln Val Lys Ala Phe Ala Asp Lys Glu Glu Gly Gly Asp Val Lys Ser
                420                 425                 430
Val Cys Met Thr Leu Phe Leu Leu Ala Leu Arg Ala Arg Asn Glu His
                435                 440                 445
Arg Gln Ala Asp Glu Leu Glu Ala Ile Met Gln Gly Lys Gly Ser Gly
                450                 455                 460
Leu Gln Pro Ala Val Cys Leu Ala Ile Arg Val Asn Thr Phe Leu Ser
465                 470                 475                 480
Cys Ser Gln Tyr His Lys Met Tyr Arg Thr Val Lys Ala Ile Thr Gly
                485                 490                 495
Arg Gln Ile Phe Gln Pro Leu His Ala Leu Arg Asn Ala Glu Lys Val
                500                 505                 510
Leu Leu Pro Gly Tyr His His Phe Glu Trp Gln Pro Pro Leu Lys Asn
                515                 520                 525
Val Ser Ser Thr Asp Val Gly Ile Ile Asp Gly Leu Ser Gly Leu
                530                 535                 540
Ser Ser Ser Val Asp Asp Tyr Pro Val Asp Thr Ile Ala Lys Arg Phe
545                 550                 555                 560
Arg Tyr Asp Ser Ala Leu Val Ser Ala Leu Met Asp Met Glu Glu Asp
                565                 570                 575
Ile Leu Glu Gly Met Arg Ser Gln Asp Leu Asp Asp Tyr Leu Asn Gly
                580                 585                 590
Pro Phe Thr Val Val Lys Glu Ser Cys Asp Gly Met Gly Asp Val
                595                 600                 605
Ser Glu Lys His Gly Ser Gly Pro Val Val Pro Glu Lys Ala Val Arg
                610                 615                 620
Phe Ser Phe Thr Ile Met Lys Ile Thr Ile Ala His Ser Ser Gln Asn
625                 630                 635                 640
Val Lys Val Phe Glu Glu Ala Lys Pro Asn Ser Glu Leu Cys Cys Lys
                645                 650                 655
Pro Leu Cys Leu Met Leu Ala Asp Glu Ser Asp His Glu Thr Leu Thr
                660                 665                 670
Ala Ile Leu Ser Pro Leu Ile Ala Glu Arg Glu Ala Met Lys Ser Ser
                675                 680                 685
Glu Leu Met Leu Glu Leu Gly Gly Ile Leu Arg Thr Phe Lys Phe Ile
                690                 695                 700
```

```
Phe Arg Gly Thr Gly Tyr Asp Glu Lys Leu Val Arg Glu Val Glu Gly
705                 710                 715                 720

Leu Glu Ala Ser Gly Ser Val Tyr Ile Cys Thr Leu Cys Asp Ala Thr
            725                 730                 735

Arg Leu Glu Ala Ser Gln Asn Leu Val Phe His Ser Ile Thr Arg Ser
        740                 745                 750

His Ala Glu Asn Leu Glu Arg Tyr Glu Val Trp Arg Ser Asn Pro Tyr
    755                 760                 765

His Glu Ser Val Glu Glu Leu Arg Asp Arg Val Lys Gly Val Ser Ala
770                 775                 780

Lys Pro Phe Ile Glu Thr Val Pro Ser Ile Asp Ala Leu His Cys Asp
785                 790                 795                 800

Ile Gly Asn Ala Ala Glu Phe Tyr Lys Ile Phe Gln Leu Glu Ile Gly
                805                 810                 815

Glu Val Tyr Lys Asn Pro Asn Ala Ser Lys Glu Glu Arg Lys Arg Trp
            820                 825                 830

Gln Ala Thr Leu Asp Lys His Leu Arg Lys Met Asn Leu Lys Pro
        835                 840                 845

Ile Met Arg Met Asn Gly Asn Phe Ala Arg Lys Leu Met Thr Lys Glu
    850                 855                 860

Thr Val Asp Ala Val Cys Glu Leu Ile Pro Ser Glu Glu Arg His Glu
865                 870                 875                 880

Ala Leu Arg Glu Leu Met Asp Leu Tyr Leu Lys Met Lys Pro Val Trp
                885                 890                 895

Arg Ser Ser Cys Pro Ala Lys Glu Cys Pro Glu Ser Leu Cys Gln Tyr
            900                 905                 910

Ser Phe Asn Ser Gln Arg Phe Ala Glu Leu Leu Ser Thr Lys Phe Lys
        915                 920                 925

Tyr Arg Asn
930

<210> SEQ ID NO 2
<211> LENGTH: 2796
<212> TYPE: DNA
<213> ORGANISM: Homo sapiens
<220> FEATURE:
<221> NAME/KEY: misc_feature
<223> OTHER INFORMATION: RAG-1 Accession number: BC037344.2

<400> SEQUENCE: 2
atggcagcct ctttcccacc caccttggga ctcagttctg ccccagatga aattcagcac      60
ccacatatta aattttcaga atggaaattt aagctgttcc gggtgagatc ctttgaaaag     120
acacctgaag aagctcaaaa ggaaaagaag gattcctttg aggggaaacc ctctctggag     180
caatctccag cagtcctgga caaggctgat ggtcagaagc cagtcccaac tcagccattg     240
ttaaaagccc accctaagtt ttcaaagaaa tttcacgaca cgagaaagc aagaggcaaa     300 gcgatccatc aagccaacct tcgacatctc tgccgcatct gtgggaattc ttttagagct     360
gatgagcaca caggagata tccagtccat ggtcctgtgg atggtaaaac cctaggcctt     420
ttacgaaaga aggaaaagag agctacttcc tggccggacc tcattgccaa ggttttccgg     480
atcgatgtga aggcagatgt tgactcgatc caccccactg agttctgcca taactgctgg     540
agcatcatgc acaggaagtt tagcagtgcc ccatgtgagg tttacttccc gaggaacgtg     600
accatggagt ggcacccca cacaccatcc tgtgacatct gcaacactgc ccgtcgggga     660
```

-continued

```
ctcaagagga agagtcttca gccaaacttg cagctcagca aaaaactcaa aactgtgctt    720
gaccaagcaa gacaagcccg tcagcgcaag agaagagctc aggcaaggat cagcagcaag    780
gatgtcatga agaagatcgc caactgcagt aagatacatc ttagtaccaa gctccttgca    840
gtggacttcc cagagcactt tgtgaaatcc atctcctgcc agatctgtga acacattctg    900
gctgaccctg tggagaccaa ctgtaagcat gtcttttgcc gggtctgcat tctcagatgc    960
ctcaaagtca tgggcagcta ttgtccctct tgccgatatc catgcttccc tactgacctg    1020
gagagtccag tgaagtcctt tctgagcgtc ttgaattccc tgatggtgaa atgtccagca    1080
aaagagtgca atgaggaggt cagtttggaa aaatataatc accacatctc aagtcacaag    1140
gaatcaaaag agattttttgt gcacattaat aaagggggcc ggccccgcca acatcttctg    1200
tcgctgactc ggagagctca gaagcaccgg ctgagggagc tcaagctgca agtcaaagcc    1260
tttgctgaca agaagaagg tggagatgtg aagtccgtgt gcatgacctt gttcctgctg    1320
gctctgaggg cgaggaatga gcacaggcaa gctgatgagc tggaggccat catgcaggga    1380
aagggctctg gcctgcagcc agctgtttgc ttggccatcc gtgtcaacac cttcctcagc    1440
tgcagtcagt accacaagat gtacaggact gtgaaagcca tcacagggag acagattttt    1500
cagcctttgc atgcccttcg gaatgctgag aaggtacttc tgccaggcta ccaccacttt    1560
gagtggcagc cacctctgaa gaatgtgtct tccagcactg atgttggcat tattgatggg    1620
ctgtctgggc tatcatcctc tgtggatgat tacccagtgg acaccattgc aaagaggttc    1680
cgctatgatt cagctttggt gtctgctttg atggacatgg aagaagacat cttggaaggc    1740
atgagatccc aagaccttga tgattacctg aatggcccct tcactgtggt ggtgaaggag    1800
tcttgtgatg gaatgggaga cgtgagtgag aagcatggga gtgggcctgt agttccagaa    1860
aaggcagtcc gtttttcatt cacaatcatg aaaattacta ttgcccacag ctctcagaat    1920
gtgaaagtat ttgaagaagc caaacctaac tctgaactgt gttgcaagcc attgtgcctt    1980
atgctggcag atgagtctga ccacgagacg ctgactgcca tcctgagtcc tctcattgct    2040
gagagggagg ccatgaagag cagtgaatta atgcttgagc tgggaggcat tctccggact    2100
ttcaagttca tcttcagggg caccggctat gatgaaaaac ttgtgcggga agtggaaggc    2160
ctcgaggctt ctggctcagt ctacatttgt actctttgtg atgccacccg tctggaagcc    2220
tctcaaaatc ttgtcttcca ctctataacc agaagccatg ctgagaacct ggaacgttat    2280
gaggtctggc gttccaaccc ttaccatgag tctgtggaag aactgcggga tcgggtgaaa    2340
ggggtctcag ctaaaccttt cattgagaca gtcccttcca tagatgcact ccactgtgac    2400
attggcaatg cagctgagtt ctacaagatc ttccagctag atagggga agtgtataag    2460 aatcccaatg cttccaaaga ggaaaggaaa aggtggcagg ccacactgga caagcatctc    2520
cggaagaaga tgaacctcaa accaatcatg aggatgaatg gcaactttgc caggaagctc    2580
atgaccaaag agactgtgga tgcagttttgt gagttaattc cttccgagga gaggcacgag    2640
gctctgaggg agctgatgga tctttacctg aagatgaaac cagtatggcg atcatcatgc    2700
cctgctaaag agtgcccaga atccctctgc cagtacagtt tcaattcaca gcgttttgct    2760
gagctccttt ctacgaagtt caagtataga aattaa                              2796
```

<210> SEQ ID NO 3
<211> LENGTH: 1040
<212> TYPE: PRT
<213> ORGANISM: Mus musculus
<220> FEATURE:
<221> NAME/KEY: MISC_FEATURE
<223> OTHER INFORMATION: RAG-1 Accession number: NP_033045.2

<400> SEQUENCE: 3

```
Met Ala Ala Ser Leu Pro Ser Thr Leu Ser Phe Ser Ala Pro Asp
1               5                   10                  15

Glu Ile Gln His Pro Gln Ile Lys Phe Ser Glu Trp Lys Phe Lys Leu
            20                  25                  30

Phe Arg Val Arg Ser Phe Glu Lys Ala Pro Glu Glu Ala Gln Lys Glu
        35                  40                  45

Lys Asp Ser Ser Glu Gly Lys Pro Tyr Leu Glu Gln Ser Pro Val Val
50                  55                  60

Pro Glu Lys Pro Gly Gly Gln Asn Ser Ile Leu Thr Gln Arg Ala Leu
65                  70                  75                  80

Lys Leu His Pro Lys Phe Ser Lys Phe His Ala Asp Gly Lys Ser
            85                  90                  95

Ser Asp Lys Ala Val His Gln Ala Arg Leu Arg His Phe Cys Arg Ile
            100                 105                 110

Cys Gly Asn Arg Phe Lys Ser Asp Gly His Ser Arg Tyr Pro Val
            115                 120                 125

His Gly Pro Val Asp Ala Lys Thr Gln Ser Leu Phe Arg Lys Lys Glu
130                 135                 140

Lys Arg Val Thr Ser Trp Pro Asp Leu Ile Ala Arg Ile Phe Arg Ile
145                 150                 155                 160

Asp Val Lys Ala Asp Val Asp Ser Ile His Pro Thr Glu Phe Cys His
            165                 170                 175

Asp Cys Trp Ser Ile Met His Arg Lys Phe Ser Ser His Ser Gln
            180                 185                 190

Val Tyr Phe Pro Arg Lys Val Thr Val Glu Trp His Pro His Thr Pro
            195                 200                 205

Ser Cys Asp Ile Cys Phe Thr Ala His Arg Gly Leu Lys Arg Lys Arg
210                 215                 220

His Gln Pro Asn Val Gln Leu Ser Lys Lys Leu Lys Thr Val Leu Asn
225                 230                 235                 240

His Ala Arg Arg Asp Arg Arg Lys Arg Thr Gln Ala Arg Val Ser Ser
            245                 250                 255

Lys Glu Val Leu Lys Lys Ile Ser Asn Cys Ser Lys Ile His Leu Ser
            260                 265                 270

Thr Lys Leu Leu Ala Val Asp Phe Pro Ala His Phe Val Lys Ser Ile
            275                 280                 285

Ser Cys Gln Ile Cys Glu His Ile Leu Ala Asp Pro Val Glu Thr Ser
290                 295                 300

Cys Lys His Leu Phe Cys Arg Ile Cys Ile Leu Arg Cys Leu Lys Val
305                 310                 315                 320

Met Gly Ser Tyr Cys Pro Ser Cys Arg Tyr Pro Cys Phe Pro Thr Asp
            325                 330                 335

Leu Glu Ser Pro Val Lys Ser Phe Leu Asn Ile Leu Asn Ser Leu Met
            340                 345                 350

Val Lys Cys Pro Ala Gln Asp Cys Asn Glu Glu Val Ser Leu Glu Lys
            355                 360                 365

Tyr Asn His His Val Ser Ser His Lys Glu Ser Lys Glu Thr Leu Val
            370                 375                 380

His Ile Asn Lys Gly Gly Arg Pro Arg Gln His Leu Leu Ser Leu Thr
385                 390                 395                 400
```

```
Arg Arg Ala Gln Lys His Arg Leu Arg Glu Leu Lys Ile Gln Val Lys
            405                 410                 415
Glu Phe Ala Asp Lys Glu Glu Gly Gly Asp Val Lys Ala Val Cys Leu
            420                 425                 430
Thr Leu Phe Leu Leu Ala Leu Arg Ala Arg Asn Glu His Arg Gln Ala
            435                 440                 445
Asp Glu Leu Glu Ala Ile Met Gln Gly Arg Gly Ser Gly Leu Gln Pro
            450                 455                 460
Ala Val Cys Leu Ala Ile Arg Val Asn Thr Phe Leu Ser Cys Ser Gln
465                 470                 475                 480
Tyr His Lys Met Tyr Arg Thr Val Lys Ala Ile Thr Gly Arg Gln Ile
            485                 490                 495
Phe Gln Pro Leu His Ala Leu Arg Asn Ala Glu Lys Val Leu Leu Pro
            500                 505                 510
Gly Tyr His Pro Phe Glu Trp Gln Pro Pro Leu Lys Asn Val Ser Ser
            515                 520                 525
Arg Thr Asp Val Gly Ile Ile Asp Gly Leu Ser Gly Leu Ala Ser Ser
            530                 535                 540
Val Asp Glu Tyr Pro Val Asp Thr Ile Ala Lys Arg Phe Arg Tyr Asp
545                 550                 555                 560
Ser Ala Leu Val Ser Ala Leu Met Asp Met Glu Glu Asp Ile Leu Glu
            565                 570                 575
Gly Met Arg Ser Gln Asp Leu Asp Asp Tyr Leu Asn Gly Pro Phe Thr
            580                 585                 590
Val Val Val Lys Glu Ser Cys Asp Gly Met Gly Asp Val Ser Glu Lys
            595                 600                 605
His Gly Ser Gly Pro Ala Val Pro Glu Lys Ala Val Arg Phe Ser Phe
            610                 615                 620
Thr Val Met Arg Ile Thr Ile Glu His Gly Ser Gln Asn Val Lys Val
625                 630                 635                 640
Phe Glu Glu Pro Lys Pro Asn Ser Glu Leu Cys Cys Lys Pro Leu Cys
            645                 650                 655
Leu Met Leu Ala Asp Glu Ser Asp His Glu Thr Leu Thr Ala Ile Leu
            660                 665                 670
Ser Pro Leu Ile Ala Glu Arg Glu Ala Met Lys Ser Ser Glu Leu Thr
            675                 680                 685
Leu Glu Met Gly Gly Ile Pro Arg Thr Phe Lys Phe Ile Phe Arg Gly
            690                 695                 700
Thr Gly Tyr Asp Glu Lys Leu Val Arg Glu Val Glu Gly Leu Glu Ala
705                 710                 715                 720
Ser Gly Ser Val Tyr Ile Cys Thr Leu Cys Asp Thr Thr Arg Leu Glu
            725                 730                 735
Ala Ser Gln Asn Leu Val Phe His Ser Ile Thr Arg Ser His Ala Glu
            740                 745                 750
Asn Leu Gln Arg Tyr Glu Val Trp Arg Ser Asn Pro Tyr His Glu Ser
            755                 760                 765
Val Glu Glu Leu Arg Asp Arg Val Lys Gly Val Ser Ala Lys Pro Phe
            770                 775                 780
Ile Glu Thr Val Pro Ser Ile Asp Ala Leu His Cys Asp Ile Gly Asn
785                 790                 795                 800
Ala Ala Glu Phe Tyr Lys Ile Phe Gln Leu Glu Ile Gly Glu Val Tyr
            805                 810                 815
Lys His Pro Asn Ala Ser Lys Glu Glu Arg Lys Arg Trp Gln Ala Thr
```

```
            820             825             830
Leu Asp Lys His Leu Arg Lys Arg Met Asn Leu Lys Pro Ile Met Arg
                835             840             845

Met Asn Gly Asn Phe Ala Arg Lys Leu Met Thr Gln Glu Thr Val Asp
    850             855             860

Ala Val Cys Glu Leu Ile Pro Ser Glu Glu Arg His Glu Ala Leu Arg
865             870             875             880

Glu Leu Met Asp Leu Tyr Leu Lys Met Lys Pro Val Trp Arg Ser Ser
                885             890             895

Cys Pro Ala Lys Glu Cys Pro Glu Ser Leu Cys Gln Tyr Ser Phe Asn
            900             905             910

Ser Gln Arg Phe Ala Glu Leu Leu Ser Thr Lys Phe Lys Tyr Arg Tyr
        915             920             925

Glu Gly Lys Ile Thr Asn Tyr Phe His Lys Thr Leu Ala His Val Pro
    930             935             940

Glu Ile Ile Glu Arg Asp Gly Ser Ile Gly Ala Trp Ala Ser Glu Gly
945             950             955             960

Asn Glu Ser Gly Asn Lys Leu Phe Arg Arg Phe Arg Lys Met Asn Ala
                965             970             975

Arg Gln Ser Lys Cys Tyr Glu Met Glu Asp Val Leu Lys His His Trp
            980             985             990

Leu Tyr Thr Ser Lys Tyr Leu Gln Lys Phe Met Asn Ala His Asn Ala
        995             1000            1005

Leu Lys Ser Ser Gly Phe Thr Met Asn Ser Lys Glu Thr Leu Gly
    1010            1015            1020

Asp Pro Leu Gly Ile Glu Asp Ser Leu Glu Ser Gln Asp Ser Met
    1025            1030            1035

Glu Phe
    1040

<210> SEQ ID NO 4
<211> LENGTH: 3123
<212> TYPE: DNA
<213> ORGANISM: Mus musculus
<220> FEATURE:
<221> NAME/KEY: misc_feature
<223> OTHER INFORMATION: RAG-1 Accession number: NM_009019.2

<400> SEQUENCE: 4
atggctgcct ccttgccgtc taccctgagc ttcagttctg cacccgatga aattcaacac      60
ccacaaatca aattttccga gtggaaattt aagctgttta gggtgagatc ctttgaaaag     120
gcacccgaag aagcacagaa ggagaaggat tcctcagagg ggaaacctta cctagaacag     180
tctccagtag ttccagagaa gcctggtggt cagaactcaa ttctgactca acgagcactg     240
aaactccatc ctaaattttc aaagaaattc catgctgatg ggaagtcaag cgacaaagca     300
gttcaccaag ccaggcttag acacttctgc cgcatctgtg gaatcgtttt caagagtgac     360
gggcacagcc ggagataccc agtccacggg cccgtggacg ctaaacccca agtcttttc      420 cgaaagaagg aaaaaagagt cacttcctgg ccagacctca ttgccaggat tttccggatc     480
gacgtgaagg cagatgttga ctccatccac ccgacggaat ctgccatga ctgttggagc      540 atcatgcaca gaaagttcag cagttcccac agtcaggtct acttcccaag gaaagtgacc     600
gtggagtggc acccccacac accgtcctgt gacatctgtt ttactgccca tcggggactc     660
aagaggaaga gacatcagcc caatgtgcag ctcagcaaga aactaaaaac tgtgctcaac     720
```

```
cacgcgagac gggaccgtcg caagagaact caggctaggg tcagcagcaa ggaagtcctg    780
aagaagatct ccaactgcag taagattcat ctcagtacca agcttcttgc cgtggacttc    840
ccagcacact ttgtgaaatc catctcctgc cagatatgcg aacacattct ggctgatccc    900
gtggagacca gctgcaagca tctattctgt aggatctgca ttctcagatg tctcaaagtc    960
atgggcagct attgtccctc ttgccgatat ccgtgcttcc ctactgacct ggagagccca   1020
gtgaagtcct ttctgaacat cttgaattct ctcatggtca agtgtcccgc caagattgc    1080 aatgaggaag tgagtctgga aaaatataac caccatgtgt caagccacaa agaatctaaa   1140
gagactttgg tgcatatcaa taaagggggga cggcctcgcc agcatctcct gtcactgacg   1200
agaagggcgc agaaacatcg gctgagggag ctcaagattc aagtcaaaga atttgctgac   1260
aaagaagaag gtggagatgt gaaggctgtc tgcttgacat tgtttctcct ggcactgagg   1320
gcgaggaatg agcacaggca agctgatgaa ttagaggcca tcatgcaagg caggggctcc   1380
gggcttcaac cagctgtttg cttggccatc cgtgtcaata ccttcctcag ctgtagccaa   1440
taccataaga tgtacaggac tgtgaaagct atcactggga ggcagatttt tcaacctttg   1500
catgctcttc ggaatgccga gaaagtcctt ctgccaggct accatcccct tgagtggcag   1560
cccccactga agaatgtgtc ctccagaact gatgttggaa ttattgatgg gctgtctgga   1620
cttgcctcct ctgtggatga gtacccagta gataccattg cgaagaggtt ccgctacgac   1680
tctgctttgg tgtctgcttt gatggacatg gaagaagaca tcttggaagg catgagatcc   1740
caagatcttg atgactacct gaatggtccc ttcacagtgg tggtaaagga gtcttgcgat   1800
ggaatggggg atgtgagtga gaagcacggg agtgggcccg cagttccaga aaaggccgtt   1860
cgtttctctt tcacagtcat gagaattacg atagagcatg gttcacagaa cgtgaaggtg   1920
tttgaggaac ccaagcccaa ttctgaactg tgttgcaagc cgttgtgtct tatgctggca   1980
gatgagtctg accatgagac ccttactgct attctaagcc ccctcattgc cgagagggag   2040
gccatgaaga gcagtgaatt aacgctggag atggaggca tccccaggac ttttaaattc   2100
atcttcaggg gcactggata cgatgaaaaa cttgtccggg aagtagaagg cttggaagct   2160
tctggctcag tctacatctg tacactctgt gacaccaccc gtttggaagc ctctcagaat   2220
cttgtcttcc actccataac cagaagccac gccgagaacc tgcagcgcta tgaggtctgg   2280
cggtccaatc cgtatcatga gtccgtggaa gagctccggg accgggtgaa aggggtctct   2340
gccaaacctt tcatcgagac agtcccttcc atagatgcgc ttcactgtga cattggcaat   2400
gcagctgaat tctataagat tttccagctg gagatagggg aagtgtataa acatcccaat   2460
gcctctaaag aggaaaggaa gagatggcag gccacgctgg acaaacatct ccggaaaagg   2520
atgaacttaa aaccaatcat gaggatgaat ggcaactttg cccggaagct tatgaccccaa   2580 gagactgtag acgcagtttg tgagttaatt ccttctgagg agaggcatga agctctcagg   2640
gagctcatgg acctttacct gaagatgaaa cccgtgtggc gctcttcatg tcccgctaaa   2700
gagtgtccag agtccctctg tcagtacagt ttcaactcac agcgtttcgc ggaactcctc   2760
tccaccaagt tcaaatatag atacgagggc aaaatcacca attactttca caaaaccttg   2820
gcacatgtcc ctgaaattat tgaaagggat ggctctatcg gggcctgggc aagtgaggga   2880
aatgaatcgg gtaacaagct gtttagacgg tttcggaaaa tgaatgccag gcagtccaag   2940
tgctatgaga tggaagatgt cctgaaacat cactggctgt atacttcaaa atacctccag   3000
aagtttatga atgctcataa cgcgttaaaa agctctgggt ttaccatgaa ctcaaaggag   3060
accttagggg acccttggg cattgaggac tctctggaaa gccaagattc aatggagttt   3120
```

-continued taa                                                    3123

<210> SEQ ID NO 5
<211> LENGTH: 527
<212> TYPE: PRT
<213> ORGANISM: Homo sapiens
<220> FEATURE:
<221> NAME/KEY: MISC_FEATURE
<223> OTHER INFORMATION: RAG-2 Accession number: NP_001230715.1

<400> SEQUENCE: 5

Met Ser Leu Gln Met Val Thr Val Ser Asn Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Leu
        35                  40                  45

Asp Val Lys His Asn His Val Lys Leu Lys Pro Thr Ile Phe Ser Lys
    50                  55                  60

Asp Ser Cys Tyr Leu Pro Pro Leu Arg Tyr Pro Ala Thr Cys Thr Phe
65                  70                  75                  80

Lys Gly Ser Leu Glu Ser Glu Lys His Gln Tyr Ile Ile His Gly Gly
                85                  90                  95

Lys Thr Pro Asn Asn Glu Val Ser Asp Lys Ile Tyr Val Met Ser Ile
            100                 105                 110

Val Cys Lys Asn Asn Lys Lys Val Thr Phe Arg Cys Thr Glu Lys Asp
        115                 120                 125

Leu Val Gly Asp Val Pro Glu Ala Arg Tyr Gly His Ser Ile Asn Val
    130                 135                 140

Val Tyr Ser Arg Gly Lys Ser Met Gly Val Leu Phe Gly Gly Arg Ser
145                 150                 155                 160

Tyr Met Pro Ser Thr His Arg Thr Thr Glu Lys Trp Asn Ser Val Ala
                165                 170                 175

Asp Cys Leu Pro Cys Val Phe Leu Val Asp Phe Glu Phe Gly Cys Ala
            180                 185                 190

Thr Ser Tyr Ile Leu Pro Glu Leu Gln Asp Gly Leu Ser Phe His Val
        195                 200                 205

Ser Ile Ala Lys Asn Asp Thr Ile Tyr Ile Leu Gly Gly His Ser Leu
    210                 215                 220

Ala Asn Asn Ile Arg Pro Ala Asn Leu Tyr Arg Ile Arg Val Asp Leu
225                 230                 235                 240

Pro Leu Gly Ser Pro Ala Val Asn Cys Thr Val Leu Pro Gly Gly Ile
                245                 250                 255

Ser Val Ser Ser Ala Ile Leu Thr Gln Thr Asn Asn Asp Glu Phe Val
            260                 265                 270

Ile Val Gly Gly Tyr Gln Leu Glu Asn Gln Lys Arg Met Ile Cys Asn
        275                 280                 285

Ile Ile Ser Leu Glu Asp Asn Lys Ile Glu Ile Arg Glu Met Glu Thr
    290                 295                 300

Pro Asp Trp Thr Pro Asp Ile Lys His Ser Lys Ile Trp Phe Gly Ser
305                 310                 315                 320

Asn Met Gly Asn Gly Thr Val Phe Leu Gly Ile Pro Gly Asp Asn Lys
                325                 330                 335

Gln Val Val Ser Glu Gly Phe Tyr Phe Tyr Met Leu Lys Cys Ala Glu
            340                 345                 350

```
Asp Asp Thr Asn Glu Glu Gln Thr Thr Phe Thr Asn Ser Gln Thr Ser
        355                 360                 365

Thr Glu Asp Pro Gly Asp Ser Thr Pro Phe Glu Asp Ser Glu Glu Phe
    370                 375                 380

Cys Phe Ser Ala Glu Ala Asn Ser Phe Asp Gly Asp Asp Glu Phe Asp
385                 390                 395                 400

Thr Tyr Asn Glu Asp Asp Glu Asp Glu Ser Glu Thr Gly Tyr Trp
            405                 410                 415

Ile Thr Cys Cys Pro Thr Cys Asp Val Asp Ile Asn Thr Trp Val Pro
        420                 425                 430

Phe Tyr Ser Thr Glu Leu Asn Lys Pro Ala Met Ile Tyr Cys Ser His
        435                 440                 445

Gly Asp Gly His Trp Val His Ala Gln Cys Met Asp Leu Ala Glu Arg
    450                 455                 460

Thr Leu Ile His Leu Ser Ala Gly Ser Asn Lys Tyr Tyr Cys Asn Glu
465                 470                 475                 480

His Val Glu Ile Ala Arg Ala Leu His Thr Pro Gln Arg Val Leu Pro
            485                 490                 495

Leu Lys Lys Pro Pro Met Lys Ser Leu Arg Lys Lys Gly Ser Gly Lys
        500                 505                 510

Ile Leu Thr Pro Ala Lys Lys Ser Phe Leu Arg Arg Leu Phe Asp
        515                 520                 525
```

<210> SEQ ID NO 6
<211> LENGTH: 1584
<212> TYPE: DNA
<213> ORGANISM: Homo sapiens
<220> FEATURE:
<221> NAME/KEY: misc_feature
<223> OTHER INFORMATION: RAG-2 Accession number: NM_001243786.1

<400> SEQUENCE: 6

```
atgtctctgc agatggtaac agtcagtaat aacatagcct taattcagcc aggcttctca      60
ctgatgaatt ttgatggaca gttttcttc  tttggacaaa aaggctggcc caaaagatcc     120
tgccccactg gagttttcca tctggatgta aagcataacc atgtcaaact gaagcctaca     180
attttctcta aggattcctg ctacctccct cctcttcgct acccagccac ttgcacattc     240
aaaggcagct tggagtctga aaagcatcaa tacatcatcc atggagggaa acaccaaac     300 aatgaggttt cagataagat ttatgtcatg tctattgttt gcaagaacaa caaaaaggtt     360
acttttcgct gcacagagaa agacttggta ggagatgttc ctgaagccag atatggtcat     420
tccattaatg tggtgtacag ccgagggaaa agtatgggtg ttctctttgg aggacgctca     480
tacatgcctt ctacccacag aaccacagaa aaatggaata gtgtagctga ctgcctgccc     540
tgtgttttcc tggtggattt tgaatttggg tgtgctacat catacattct tccagaactt     600
caggatgggc tatcttttca tgtctctatt gccaaaaatg acaccatcta tttttagga     660 ggacattcac ttgccaataa tatccggcct gccaacctgt acagaataag ggttgatctt     720
cccctgggta gcccagctgt gaattgcaca gtcttgccag gaggaatctc tgtctccagt     780
gcaatcctga ctcaaactaa caatgatgaa tttgttattg ttggtggcta tcagcttgaa     840
aatcaaaaaa gaatgatctg caacatcatc tctttagagg acaacaagat agaaattcgt     900
gagatggaga cccagattg  gaccccagac attaagcaca gcaagatatg gtttggaagc     960
aacatgggaa atggaactgt ttttcttggc ataccaggag acaataaaca gttgtttca   1020
```

-continued

```
gaaggattct atttctatat gttgaaatgt gctgaagatg atactaatga agagcagaca    1080
acattcacaa acagtcaaac atcaacagaa gatccagggg attccactcc ctttgaagac    1140
tctgaagaat tttgtttcag tgcagaagca aatagttttg atggtgatga tgaatttgac    1200
acctataatg aagatgatga agaagatgag tctgagacag gctactggat tacatgctgc    1260
cctacttgtg atgtggatat caacacttgg gtaccattct attcaactga gctcaacaaa    1320
cccgccatga tctactgctc tcatggggat gggcactggg tccatgctca gtgcatggat    1380
ctggcagaac gcacactcat ccatctgtca gcaggaagca acaagtatta ctgcaatgag    1440
catgtggaga tagcaagagc tctacacact ccccaaagag tcctacccTT aaaaaagcct    1500
ccaatgaaat ccctccgtaa aaaaggttct ggaaaaatct tgactcctgc caagaaatcc    1560
tttcttagaa ggttgtttga ttag                                           1584
```

<210> SEQ ID NO 7
<211> LENGTH: 527
<212> TYPE: PRT
<213> ORGANISM: Mus musculus
<220> FEATURE:
<221> NAME/KEY: MISC_FEATURE
<223> OTHER INFORMATION: RAG-2 Accession number: NP_033046.1

<400> SEQUENCE: 7

```
Met Ser Leu Gln Met Val Thr Val Gly His Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Phe
        35                  40                  45

Asp Ile Lys Gln Asn His Leu Lys Leu Lys Pro Ala Ile Phe Ser Lys
    50                  55                  60

Asp Ser Cys Tyr Leu Pro Pro Leu Arg Tyr Pro Ala Thr Cys Ser Tyr
65                  70                  75                  80

Lys Gly Ser Ile Asp Ser Lys His Gln Tyr Ile Ile His Gly Gly
                85                  90                  95

Lys Thr Pro Asn Asn Glu Leu Ser Asp Lys Ile Tyr Ile Met Ser Val
            100                 105                 110

Ala Cys Lys Asn Asn Lys Lys Val Thr Phe Arg Cys Thr Glu Lys Asp
        115                 120                 125

Leu Val Gly Asp Val Pro Glu Pro Arg Tyr Gly His Ser Ile Asp Val
    130                 135                 140

Val Tyr Ser Arg Gly Lys Ser Met Gly Val Leu Phe Gly Gly Arg Ser
145                 150                 155                 160

Tyr Met Pro Ser Thr Gln Arg Thr Thr Glu Lys Trp Asn Ser Val Ala
                165                 170                 175

Asp Cys Leu Pro His Val Phe Leu Ile Asp Phe Glu Phe Gly Cys Ala
            180                 185                 190

Thr Ser Tyr Ile Leu Pro Glu Leu Gln Asp Gly Leu Ser Phe His Val
        195                 200                 205

Ser Ile Ala Arg Asn Asp Thr Val Tyr Ile Leu Gly Gly His Ser Leu
    210                 215                 220

Ala Ser Asn Ile Arg Pro Ala Asn Leu Tyr Arg Ile Arg Val Asp Leu
225                 230                 235                 240

Pro Leu Gly Thr Pro Ala Val Asn Cys Thr Val Leu Pro Gly Gly Ile
                245                 250                 255
```

```
Ser Val Ser Ser Ala Ile Leu Thr Gln Thr Asn Asn Asp Glu Phe Val
            260                 265                 270

Ile Val Gly Gly Tyr Gln Leu Glu Asn Gln Lys Arg Met Val Cys Ser
        275                 280                 285

Leu Val Ser Leu Gly Asp Asn Thr Ile Glu Ile Ser Glu Met Glu Thr
    290                 295                 300

Pro Asp Trp Thr Ser Asp Ile Lys His Ser Lys Ile Trp Phe Gly Ser
305                 310                 315                 320

Asn Met Gly Asn Gly Thr Ile Phe Leu Gly Ile Pro Gly Asp Asn Lys
                325                 330                 335

Gln Ala Met Ser Glu Ala Phe Tyr Phe Tyr Thr Leu Arg Cys Ser Glu
            340                 345                 350

Glu Asp Leu Ser Glu Asp Gln Lys Ile Val Ser Asn Ser Gln Thr Ser
        355                 360                 365

Thr Glu Asp Pro Gly Asp Ser Thr Pro Phe Glu Asp Ser Glu Glu Phe
    370                 375                 380

Cys Phe Ser Ala Glu Ala Thr Ser Phe Asp Gly Asp Asp Glu Phe Asp
385                 390                 395                 400

Thr Tyr Asn Glu Asp Asp Glu Asp Glu Ser Val Thr Gly Tyr Trp
                405                 410                 415

Ile Thr Cys Cys Pro Thr Cys Asp Val Asp Ile Asn Thr Trp Val Pro
            420                 425                 430

Phe Tyr Ser Thr Glu Leu Asn Lys Pro Ala Met Ile Tyr Cys Ser His
        435                 440                 445

Gly Asp Gly His Trp Val His Ala Gln Cys Met Asp Leu Glu Glu Arg
    450                 455                 460

Thr Leu Ile His Leu Ser Glu Gly Ser Asn Lys Tyr Tyr Cys Asn Glu
465                 470                 475                 480

His Val Gln Ile Ala Arg Ala Leu Gln Thr Pro Lys Arg Asn Pro Pro
                485                 490                 495

Leu Gln Lys Pro Pro Met Lys Ser Leu His Lys Lys Gly Ser Gly Lys
            500                 505                 510

Val Leu Thr Pro Ala Lys Lys Ser Phe Leu Arg Arg Leu Phe Asp
        515                 520                 525
```

<210> SEQ ID NO 8
<211> LENGTH: 1584
<212> TYPE: DNA
<213> ORGANISM: Mus musculus
<220> FEATURE:
<221> NAME/KEY: misc_feature
<223> OTHER INFORMATION: RAG-2 Accession number: NM_009020.3

<400> SEQUENCE: 8

```
atgtccctgc agatggtaac agtgggtcat aacatagcct taattcaacc aggcttctca    60
cttatgaatt tgatggcca agttttcttc tttggccaga aaggctggcc taagagatcc    120
tgtcctactg gagtctttca ttttgatata aacaaaatc atctcaaact gaagcctgca    180
atcttctcta aagattcctg ctacctccca cctcttcgtt atccagctac ttgctcatac    240
aaaggcagca tagactctga caagcatcaa tatatcattc acggagggaa acaccaaac    300 aatgagcttt ccgataagat ttatatcatg tctgtcgctt gcaagaataa caaaaaagtt    360
actttccgtt gcacagagaa agacttagta ggagatgtcc ctgaaaccag atacggccat    420
tccattgacg tggtgtatag tcgagggaaa agcatgggtg ttctctttgg aggacgttca    480
tacatgcctt ctacccagag aaccacagaa aaatggaata gtgtagctga ctgcctaccc    540
```

```
catgttttct tgatagattt tgaatttggg tgtgctacat catatattct cccagaactt    600
caggatgggc tgtctttca tgtttctatt gccagaaacg ataccgttta tattttggga     660
ggacactcac ttgccagtaa tatacgccct gctaacttgt atagaataag agtggacctt    720
cccctgggta ccccagcagt gaattgcaca gtcttgccag gaggaatctc tgtctccagt    780
gcaatcctca ctcaaacaaa caatgatgaa tttgttattg tgggtggtta tcagctggaa    840
aatcagaaaa ggatggtctg cagccttgtc tctctagggg acaacacgat tgaaatcagt    900
gagatggaga ctcctgactg gacctcagat attaagcata gcaaaatatg gtttggaagc    960
aacatgggaa acgggactat tttccttggc ataccaggag acaataagca ggctatgtca    1020
gaagcattct atttctatac tttgagatgc tctgaagagg atttgagtga agatcagaaa    1080
attgtctcca acagtcagac atcaacagaa gatcctgggg actccactcc ctttgaagac    1140
tcagaggaat tttgtttcag tgctgaagca accagttttg atggtgacga tgaatttgac    1200
acctacaatg aagatgatga agatgacgag tctgtaaccg gctactggat aacatgttgc    1260
cctacttgtg atgttgacat caataccctgg gttccgttct attcaacgga gctcaataaa    1320
cccgccatga tctattgttc tcatggggat gggcactggg tacatgccca gtgcatggat    1380
ttggaagaac gcacactcat ccacttgtca gaaggaagca acaagtatta ttgcaatgaa    1440
catgtacaga tagcaagagc attgcaaact cccaaaagaa accccccctt acaaaaacct    1500
ccaatgaaat ccctccacaa aaaaggctct gggaaagtct tgactcctgc caagaaatcc    1560
ttccttagaa gactgtttga ttaa                                          1584
```

<210> SEQ ID NO 9
<211> LENGTH: 29
<212> TYPE: PRT
<213> ORGANISM: Artificial Sequence
<220> FEATURE:
<223> OTHER INFORMATION: protein stabilizing sequence

<400> SEQUENCE: 9

Met Lys Lys Leu Lys Leu Arg Leu Thr His Leu Trp Tyr Lys Leu Leu
1               5                   10                  15

Met Lys Leu Gly Leu Lys Ser Asp Glu Val Tyr Tyr Ile
            20                  25

<210> SEQ ID NO 10
<211> LENGTH: 489
<212> TYPE: PRT
<213> ORGANISM: Artificial Sequence
<220> FEATURE:
<223> OTHER INFORMATION: anti CAR-CD19

<400> SEQUENCE: 10

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr

```
                85                  90                  95
Ile Ser Asn Leu Glu Gln Glu Asp Ile Ala Thr Tyr Phe Cys Gln Gln
            100                 105                 110
Gly Asn Thr Leu Pro Tyr Thr Phe Gly Gly Gly Thr Lys Leu Glu Ile
            115                 120                 125
Thr Gly Ser Thr Ser Gly Ser Gly Lys Pro Gly Ser Gly Glu Gly Ser
            130                 135                 140
Thr Lys Gly Glu Val Lys Leu Gln Glu Ser Gly Pro Gly Leu Val Ala
145                 150                 155                 160
Pro Ser Gln Ser Leu Ser Val Thr Cys Thr Val Ser Gly Val Ser Leu
                165                 170                 175
Pro Asp Tyr Gly Val Ser Trp Ile Arg Gln Pro Pro Arg Lys Gly Leu
            180                 185                 190
Glu Trp Leu Gly Val Ile Trp Gly Ser Glu Thr Thr Tyr Tyr Asn Ser
            195                 200                 205
Ala Leu Lys Ser Arg Leu Thr Ile Ile Lys Asp Asn Ser Lys Ser Gln
            210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Gly Gly Ser Tyr Ala Met Asp Tyr
                245                 250                 255
Trp Gly Gln Gly Thr Ser Val Thr Val Ser Ser Ala Ala Ile Glu
            260                 265                 270
Val Met Tyr Pro Pro Pro Tyr Leu Asp Asn Glu Lys Ser Asn Gly Thr
            275                 280                 285
Ile Ile His Val Lys Gly Lys His Leu Cys Pro Ser Pro Leu Phe Pro
            290                 295                 300
Gly Pro Ser Lys Pro Phe Trp Val Leu Val Val Val Gly Gly Val Leu
305                 310                 315                 320
Ala Cys Tyr Ser Leu Leu Val Thr Val Ala Phe Ile Ile Phe Trp Val
                325                 330                 335
Arg Ser Lys Arg Ser Arg Leu Leu His Ser Asp Tyr Met Asn Met Thr
            340                 345                 350
Pro Arg Arg Pro Gly Pro Thr Arg Lys His Tyr Gln Pro Tyr Ala Pro
            355                 360                 365
Pro Arg Asp Phe Ala Ala Tyr Arg Ser Arg Val Lys Phe Ser Arg Ser
            370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
            435                 440                 445
Ser Glu Ile Gly Met Lys Gly Glu Arg Arg Arg Gly Lys Gly His Asp
            450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 11
```

<211> LENGTH: 789
<212> TYPE: DNA
<213> ORGANISM: Artificial Sequence
<220> FEATURE:
<223> OTHER INFORMATION: anti Tn-MUC1 CAR

<400> SEQUENCE: 11

```
atggaatggt cttgggtgtt cctgttcttc ctgagcgtga ccaccggcgt gcacagccag      60
gtgcagctgc agcagtctga tgccgagctc gtgaagcctg gcagcagcgt gaagatcagc     120
tgcaaggcca gcggctacac cttcaccgac cacgccatcc actgggtcaa gcagaagcct     180
gagcagggcc tggaatggat cggccacttc agccccggca caccgacat caagtacaac      240
gacaagttca agggcaaggc caccctgacc gtggacagaa gcagcagcac cgcctacatg     300
cagctgaaca gcctgaccag cgaggacagc gccgtgtact tctgcaagac cagcaccttc     360
tttttcgact actggggcca gggcacaacc ctgacagtgt ctagcggcgg aggcggatct     420
ggcggcggag gatctggggg aggcggctct gaactcgtga tgacccagag ccccagctct     480
ctgacagtga cagccggcga gaaagtgacc atgatctgca agtcctccca gagcctgctg     540
aactccggcg accagaagaa ctacctgacc tggtatcagc agaaacccgg ccagcccccc     600
aagctgctga tcttttgggc cagcacccgg gaaagcggcg tgcccgatag attcacaggc     660
agcggctccg gcaccgactt taccctgacc atcagctccg tgcaggccga ggacctggcc     720
gtgtattact gccagaacga ctacagctac ccctgacct tcggagccgg caccaagctg      780
gaactgaag                                                             789
```

<210> SEQ ID NO 12
<211> LENGTH: 220
<212> TYPE: PRT
<213> ORGANISM: Artificial Sequence
<220> FEATURE:
<223> OTHER INFORMATION: NY-ESO-1-specific TCR

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Gly Trp Val Arg Gln Ala Pro Gly Lys Gly Leu Glu Trp Val
        35                  40                  45

Ser Ser Ile Gly Ser Ser Gly Gly Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Leu Leu Pro Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys
    210                 215                 220

<210> SEQ ID NO 13
<211> LENGTH: 226
<212> TYPE: PRT
<213> ORGANISM: Artificial Sequence
<220> FEATURE:
<223> OTHER INFORMATION: 3BNC117 (anti-HIV Antibody)

<400> SEQUENCE: 13

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Tyr Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 14
<211> LENGTH: 224
<212> TYPE: PRT
<213> ORGANISM: Artificial Sequence
<220> FEATURE:
<223> OTHER INFORMATION: Adalimumab (Humira) an anti-TNF? Antibody

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
                35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

<210> SEQ ID NO 15
<211> LENGTH: 116
<212> TYPE: PRT
<213> ORGANISM: Artificial Sequence
<220> FEATURE:
<223> OTHER INFORMATION: PankoMab-GEX an anti MUC1 glycoform Antibody
      heavy chain

<400> SEQUENCE: 15

Glu Val Gln Leu Val Glu Ser Gly Gly Gly Leu Val Gln Pro Gly Gly
 1               5                   10                  15

Ser Met Arg Leu Ser Cys Val Ala Ser Gly Phe Pro Phe Ser Asn Tyr
                20                  25                  30

Trp Met Asn Trp Val Arg Gln Ala Pro Gly Lys Gly Leu Glu Trp Val
                35                  40                  45

Gly Glu Ile Arg Leu Lys Ser Asn Asn Tyr Thr Thr His Tyr Ala Glu
 50                  55                  60

Ser Val Lys Gly Arg Phe Thr Ile Ser Arg Asp Ser Lys Asn Ser Leu
 65                  70                  75                  80

Tyr Leu Gln Met Asn Ser Leu Lys Thr Glu Asp Thr Ala Val Tyr Tyr
                85                  90                  95

Lys Thr Arg His Tyr Tyr Phe Asp Tyr Trp Gly Gln Gly Thr Leu Val
                100                 105                 110

Thr Val Ser Ser
        115

<210> SEQ ID NO 16
<211> LENGTH: 114
<212> TYPE: PRT
<213> ORGANISM: Artificial Sequence
<220> FEATURE:
<223> OTHER INFORMATION: PankoMab-GEX an anti MUC1 glycoform Antibody light chain

<400> SEQUENCE: 16

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ala
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gln Gly Thr Lys Val Glu Ile Lys
            100                 105                 110

Arg Ala

<210> SEQ ID NO 17
<211> LENGTH: 1200
<212> TYPE: DNA
<213> ORGANISM: Homo sapiens
<220> FEATURE:
<221> NAME/KEY: misc_feature
<223> OTHER INFORMATION: iCasp9

<400> SEQUENCE: 17

```
atgctcgagg gagtgcaggt ggaaaccatc tccccaggag acgggcgcac cttccccaag      60
cgcggccaga cctgcgtggt gcactacacc gggatgcttg aagatggaaa gaaagttgat     120
tcctcccggg acagaaacaa gcccttaag tttatgctag caagcagga ggtgatccga      180
ggctgggaag aaggggttgc ccagatgagt gtgggtcaga gagccaaact gactatatct     240
ccagattatg cctatggtgc cactgggcac ccaggcatca tccaccaca tgccactctc     300
gtcttcgatg tggagcttct aaaactggaa tctggcggtg atccggagt cgacggattt     360
ggtgatgtcg gtgctcttga gagtttgagg ggaaatgcag atttggctta catcctgagc     420
atggagccct gtggccactg cctcattatc aacaatgtga acttctgccg tgagtccggg     480
ctccgcaccc gcactggctc aacatcgac tgtgagaagt gcggcgtcg cttctcctcg      540
ctgcatttca tggtggaggt gaagggcgac ctgactgcca agaaaatggt gctggctttg     600
ctggagctgg cgcagcagga ccacggtgct ctggactgct gcgtggtggt cattctctct     660
cacggctgtc aggccagcca cctgcagttc caggggctg tctacggcac agatggatgc     720
cctgtgtcgg tcgagaagat tgtgaacatc ttcaatggga ccagctgccc cagcctggga     780
gggaagccca agctcttttt catccaggcc tgtggtgggg agcagaaaga ccatgggttt     840
gaggtggcct ccacttcccc tgaagacgag tcccctggca gtaaccccga gccagatgcc     900
accccgttcc aggaaggttt gaggaccttc gaccagctgg acgccatatc tagtttgccc     960
acacccagtg acatctttgt gtcctactct actttcccag gttttgttc ctggagggac    1020
cccaagagtg gctcctggta cgttgagacc ctggacgaca tctttgagca gtgggctcac    1080
tctgaagacc tgcagtccct cctgcttagg gtcgctaatg ctgtttcggt gaaagggatt    1140
tataacaga tgcctggttg ctttaatttc ctccggaaaa aacttttctt taaacatca     1200
```

```
<210> SEQ ID NO 18
<211> LENGTH: 23
<212> TYPE: DNA
<213> ORGANISM: Artificial Sequence
<220> FEATURE:
<223> OTHER INFORMATION: miR-181a recognition element

<400> SEQUENCE: 18
actcaccgac agcgttgaat gtt                                            23

<210> SEQ ID NO 19
<211> LENGTH: 23
<212> TYPE: DNA
<213> ORGANISM: Artificial Sequence
<220> FEATURE:
<223> OTHER INFORMATION: ECMV IRES R1

<400> SEQUENCE: 19
catatagaca aacgcacacc ggc                                            23

<210> SEQ ID NO 20
<211> LENGTH: 35
<212> TYPE: DNA
<213> ORGANISM: Artificial Sequence
<220> FEATURE:
<223> OTHER INFORMATION: IgKVm-rec-F1

<400> SEQUENCE: 20
gtccctgcca ggttyagtgg cagtggrtcw rggac                               35

<210> SEQ ID NO 21
<211> LENGTH: 33
<212> TYPE: DNA
<213> ORGANISM: Artificial Sequence
<220> FEATURE:
<223> OTHER INFORMATION: mHA-SbfI-F1 primer

<400> SEQUENCE: 21
cttaccccta tgatgtgcct gactacgctt gca                                 33

<210> SEQ ID NO 22
<211> LENGTH: 20
<212> TYPE: DNA
<213> ORGANISM: Artificial Sequence
<220> FEATURE:
<223> OTHER INFORMATION: IgKCm-rec-Rev2 primer

<400> SEQUENCE: 22
ggatggtgga agatggatac                                                20

<210> SEQ ID NO 23
<211> LENGTH: 2529
<212> TYPE: DNA
<213> ORGANISM: Artificial Sequence
<220> FEATURE:
<223> OTHER INFORMATION: Anti-polio BCR

<400> SEQUENCE: 23
atgaagctga gagtgggcca gacactgggc acaatcccta gacagtgcga ggtgctgctg    60
ctcctgctgc ttctgggact tgtgatgga gtgtcactgt ccccaggaca dacagccaac   120
atcgcctgct ctggagataa attggcggat aaatatatta actggtatca gcagaagtca   180
ggccagtccc ctgttctggt catctatgaa gatgcgaagc ggccctcagg gatccctgag   240
cgattctctg gctccagctc tgggaacaca gccactctaa ccatcagcgg gacccaggct   300
```

```
atggatgagg ctgactacta ctgtcaggcg tgggacaaca gcgctggata tgtattcgga    360
actgggacca aagtcaccgt cggtcagccc aagtccactc ccacactcac catgtttcca    420
ccttcccctg aggagctcca ggaaaacaaa gccacactcg tgtgtctgat tccaattttt    480
tccccaagtg gtgtgacagt ggcctggaag gcaaatggta cacctatcac ccagggtgtg    540
gacacttcaa atcccaccaa agaggacaac aagtacatgg ccagcagctt cttacatttg    600
acatcggacc agtggagatc tcacaacagt tttacctgcc aagttacaca tgaaggggac    660
actgtggaga agagtctgtc tcctgcagaa tgtctcggca gcggcgccac aaacttctct    720
ctgctaaagc aagcaggtga tgttgaagaa accccgggc ctatggagtt tgggctgagc    780
tgggttttcc tcgttgctct ttttagaggt gtccagtgtc tcgagtcggg cccaggactg    840
gtgaagcctt cggagaccct gtccctcacc tgcagtgtct ctagtggctt catcagtctt    900
tattcgtgga gttggatccg ccaggcacca gggacgggac tggagtggat tgggtccatc    960
cgctatagtg agaccgccta ttacaacccg tccctcaggg gtcgagtctt catatcacta   1020
gacacgtcca agaatcactt ctccctgaag atgagttctc tgaccgccac agatacggcc   1080
gtttattatt gtgcgcgaga ctacagtaag agtggctacg atcgttcggg gcggttcgac   1140
cctgggggcc agggtacccc agtcatcgtc tccatgggct gcctggcccg ggacttcctg   1200
cccagcacca tttccttcac ctggaactac cagaacaaca ctgaagtcat ccagggtatc   1260
agaaccttcc caacactgag gacaggggc aagtacctag ccacctcgca ggtgttgctg   1320
tctcccaaga gcatccttga aggttcagat gaatacctgg tatgcaaaat ccactacgga   1380
ggcaaaaaca aagatctgca tgtgcccatt ccagctgtcg cagagatgaa ccccaatgta   1440
aatgtgttcg tcccaccacg ggatggcttc tctggccctg caccacgcaa gtctaaactc   1500
atctgcgagg ccacgaactt cactccaaaa ccgatcacag tatcctggct aaaggatggg   1560
aagctcgtgg aatctggctt caccacagat ccggtgacca tcgagaacaa aggatccaca   1620
cccccaaacct acaaggtcat aagcacactt accatctctg aaatcgactg gctgaacctg   1680
aatgtgtaca cctgccgtgt ggatcacagg ggtctcacct tcttgaagaa cgtgtcctcc   1740
acatgtgctg ccagtccctc cacagacatc ctaaccttca ccatccccc ctcctttgcc   1800
gacatcttcc tcagcaagtc cgctaacctg acctgtctgg tctcaaacct ggcaacctat   1860
gaaaccctga atatctcctg ggcttctcaa agtggtgaac cactggaaac caaaattaaa   1920
atcatggaaa gccatcccaa tggcaccttc agtgctaagg gtgtggctag tgtttgtgtg   1980
gaagactgga taacaggaa ggaatttgtg tgtactgtga ctcacaggga tctgccttca   2040
ccacagaaga aattcatctc aaaacccaat gaggtgcaca acatccacc tgctgtgtac   2100
ctgctgccac cagctcgtga gcaactgaac ctgagggagt cagccacagt cacctgcctg   2160
gtgaagggct tctctcctgc agacatcagt gtgcagtggc ttcagagagg gcaactcttg   2220
ccccaagaga aatatgtgac cagtgccccg atgccagagc tgggggcccc aggcttctac   2280
tttacccaca gcatcctgac tgtgacagag gaggaatgga actccggaga gacctatacc   2340
tgtgttgtag gccacgaggc cctgccacac ctggtgaccg agaggaccgt ggacaagtcc   2400
actgaggggg aggtgaatgc tgaggaggaa ggctttgaga acctgtggac cactgcctcc   2460
accttcatcg tcctcttcct cctgagcctc ttctacagca ccaccgtcac cctgttcaag   2520
gtgaaatga                                                           2529
```

<210> SEQ ID NO 24
<211> LENGTH: 2214

<212> TYPE: DNA
<213> ORGANISM: Artificial Sequence
<220> FEATURE:
<223> OTHER INFORMATION: anti-RSV BCR

<400> SEQUENCE: 24

```
atggcgacgg gttcaagaac ttccctactt cttgcatttg gcctgctttg tttgccgtgg      60
ttacaggagg gctcggcaga catccagatg acacagagcc cctctacact gagcgccagc     120
gtgggagaca gagtgaccat cacatgcaag tgccagctga gcgtgggcta catgcactgg     180
tatcagcaga agcctggcaa ggcccctaag ctgctgatct acgacacaag caagctggcc     240
tctggcgtgc cctctagatt ttctggcagc ggctctggca ccgagttcac cctgacaatc     300
tctagcctgc agcctgacga cttcgccacc tactactgct ccaaggctc tggctacccc      360
ttcacattcg gcggaggcac caagctggaa atcaaggtgg ccgctcccag cgtgttcatc     420
ttccctccct ctgatgaaca gctgaaaagc ggaacagcca gcgtggtgtg tctgctgaac     480
aacttctacc ccagagaagc caaagtgcag tggaaggtgg acaacgccct gcagagcgga     540
aacagccagg aaagcgtgac agagcaggat tccaaggatt ccacatacag cctgagcagc     600
acactgacac tgtccaaggc cgactacgag aagcacaagg tgtacgcctg cgaagtgaca     660
caccagggac tgtcctcccc tgtgacaaag agcttcaaca gaggagaatg ccgcgcgaaa     720
cgcggaagcg gagctactaa cttcagcctg ctgaagcagg ctggagacgt ggaggagaac     780
cctggaccta tggcgacggg ttcaagaact ccctacttc ttgcatttgg cctgctttgt      840
ttgccgtggt tacaggaggg ctcggcacaa gtgaccctga gagtctgg ccccgctctg       900
gttaagccca cacagaccct gacactgacc tgcaccttca gcggcttcag cctgagcaca     960
agcggcatgt ctgtcggctg gatcagacag cctcctggca aggctctgga atggctggcc    1020
gacatttggt gggacgacaa gaaggactac aaccccagcc tgaagtccag actgaccatc    1080
agcaaggaca ccagcaagaa ccaggtggtg ctgaaagtga ccaacatgga ccctgccgac    1140
accgccacct actactgcgc cagatccatg atcaccaact ggtacttcga cgtctggggc    1200
gccggcacca cagtgacagt ttcttctagc accaagggcc catcggtctt ccccctggca    1260
ccctcctcca agagcacctc tgggggcaca gcggccctgg gctgcctggt caaggactac    1320
ttccccgaac cggtgacggt gtcgtggaac tcaggcgctc tgaccagcgg cgtgcacacc    1380
ttcccggctg tcctacagtc ctcaggactc tactccctca gcagcgtggt gaccgtgccc    1440
tccagcagct gggcacccca gacctacatc tgcaacgtga atcacaagcc cagcaacacc    1500
aaggtggaca agaaagttga gcccaaatct tgtgacaaaa ctcacacatg cccaccgtgc    1560
ccagcacctg aactcctggg gggaccgtca gtcttcctct tccccccaaa acccaaggac    1620
accctcatga tctcccggac ccctgaggtc acatgcgtgg tggtggacgt gagccacgaa    1680
gaccctgagg tcaagttcaa ctggtatgtt gacggcgtgg aggtgcataa tgccaagaca    1740
aagccgcggg aggagcagta acagcacg taccgtgtgg tcagcgtcct caccgtcctg      1800
caccaggact ggctgaatgg caaggagtac aagtgcaagg tctccaacaa agccctccca    1860
gccccatcg agaaaaccat ctccaaagcc aagggcagc cccgagaacc acaggtgtac       1920
accctgcccc catcccggga tgagctgacc aagaatcaag tcagcctgac ctgcctggtc    1980
aaaggcttct atcccagcga catcgccgtg gagtgggaga gcaatgggca gccggagaac    2040
aactacaaga ccacgcctcc cgtgctggac tccgacggct ccttcttcct ctactcaaaa    2100
ctcaccgtgg acaagagcag gtggcagcag gggaacgtct tctcatgctc cgtgatgcat    2160
```

```
gaggctctgc acaaccacta cacgcagaag agcctctccc tgtctccggg ttaa         2214
```

<210> SEQ ID NO 25
<211> LENGTH: 976
<212> TYPE: DNA
<213> ORGANISM: Artificial Sequence
<220> FEATURE:
<223> OTHER INFORMATION: V kappa 3-15 segment of the human IgK variable
      region and an HA tag

<400> SEQUENCE: 25

```
ggcttgtgcc aaacatcttc tgggtggatt taggtgattg aggagaagaa agacacagga    60
gcgaaattct ctgagcacaa gggaggagtt ctacactcag actgagccaa cagactttc   120
tggcctgaca accagggcgg cgcaggatgc tcagtgcaga gaggaagaaa caggtggtct   180
ctgcagctgg aagctcagct cccacccag ctgctttgca tgtccctccc agctgcccta   240
ccttccagag cccatatcaa tgcctgggtc agagctctgg ggaggaactg ctcagttagg   300
acccagacgg aaccatggaa gccccagcgc agcttctctt cctcctgcta ctctggctcc   360
caggtgaggg gaatatgagg tgtctttgca catcagtgaa aactcctgcc acctctgctc   420
agcaagaaat ataattaaaa ttcaatgtag atcaacaatt ttggctctac ttaaagacag   480
tgggtttgat tttgattaca tgagtgcatt tctgttttat ttccaatttc agataccact   540
ggagaaatag tgatgacgca gtctccagcc accctgtctg tgtctccagg gaaagagcc   600
accctctcct gcacttaccc ctatgatgtg cctgactacg cttgcactta ccctatgat   660
gtgcctgact acgcttgcag ggccagtcag agtgttagca gcaacttagc ctggtaccag   720
cagaaacctg gccaggctcc caggctcctc atctatggtg catccaccag gccactggt   780
atcccagcca ggttcagtgg cagtgggtct gggacagagt tcactctcac catcagcagc   840
ctgcagtctg aagattttgc agtttattac tgtcagcagt ataataactg gcctcccaca   900
gtgattcaac atgaaacaaa aacctcaaga agaccatcag tgtttactag attataccag   960
ctgcttcctt tacaga                                                   976
```

<210> SEQ ID NO 26
<211> LENGTH: 36
<212> TYPE: DNA
<213> ORGANISM: Artificial Sequence
<220> FEATURE:
<223> OTHER INFORMATION: SA 97.66 splice acceptor

<400> SEQUENCE: 26

```
ttccttttt tttcaggtgt cgtgaaaact acccct                               36
```

<210> SEQ ID NO 27
<211> LENGTH: 575
<212> TYPE: DNA
<213> ORGANISM: Artificial Sequence
<220> FEATURE:
<223> OTHER INFORMATION: ECMV IRES

<400> SEQUENCE: 27

```
cccctctccc tccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttcccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
```

```
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtacccca ttgtatggga tctgatctgg ggcctcggtg      480
cacatgcttt acatgtgttt agtcgaggtt aaaaaaacgt ctaggccccc cgaaccacgg      540
ggacgtggtt ttcctttgaa aaacacgatg ataat                                 575

<210> SEQ ID NO 28
<211> LENGTH: 22
<212> TYPE: PRT
<213> ORGANISM: Artificial Sequence
<220> FEATURE:
<223> OTHER INFORMATION: P2A picornia Virus 2A peptide

<400> SEQUENCE: 28

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 29
<211> LENGTH: 4683
<212> TYPE: DNA
<213> ORGANISM: adeno-associated virus 6, complete genome
<220> FEATURE:
<221> NAME/KEY: misc_feature
<223> OTHER INFORMATION: GenBank: AF028704.1

<400> SEQUENCE: 29
ttggccactc cctctctgcg cgctcgctcg ctcactgagg ccgggcgacc aaaggtcgcc       60
cgacgcccgg gctttgcccg gcggcctca  gtgagcgagc gagcgcgcag agagggagtg      120
gccaactcca tcactagggg ttcctggagg ggtggagtcg tgacgtgaat tacgtcatag      180
ggttagggag gtcctgtatt agaggtcacg tgagtgtttt gcgacatttt gcgacaccat      240
gtggtcacgc tgggtattta gcccgagtg  agcacgcagg gtctccattt tgaagcggga      300
ggtttgaacg cgcagcgcca tgccggggtt ttacgagatt gtgattaagg tcccagcga       360 ccttgacgag catctgcccg gcatttctga cagctttgtg aactgggtgg ccgagaagga      420
atgggagttg ccgccagatt ctgacatgga tctgaatctg attgagcagg caccctgac      480 cgtggccgag aagctgcagc gcgacttcct ggtccagtgg cgccgcgtga gtaaggcccc      540
ggaggccctc ttctttgttc agttcgagaa gggcgagtcc tacttccacc tccatattct      600
ggtggagacc acgggggtca aatccatggt gctgggccgc ttcctgagtc agattaggga      660
caagctggtg cagaccatct accgcgggat cgagccgacc ctgcccaact ggttcgcggt      720
gaccaagacg cgtaatggcg ccggaggggg gaacaaggtg gtggacgagt gctacatccc      780
caactacctc ctgcccaaga ctcagcccga gctgcagtgg gcgtggacta acatggagga      840
gtatataagc gcgtgtttaa acctggccga gcgcaaacgg ctcgtggcgc acgacctgac      900
ccacgtcagc cagacccagg agcagaacaa ggagaatctg aaccccaatt ctgacgcgcc      960
tgtcatccgg tcaaaaacct ccgcacgcta catggagctg gtcgggtggc tggtggaccg     1020
gggcatcacc tccgagaagc agtggatcca ggaggaccag gcctcgtaca tctccttcaa     1080
cgccgcctcc aactcgcggt cccagatcaa ggccgctctg acaatgccg  gcaagatcat     1140 ggcgctgacc aaatccgcgc ccgactacct ggtaggcccc gctccgcccg ccgacattaa     1200
aaccaaccgc atttaccgca tcctggagct gaacggctac gaccctgcct acgccggctc     1260
```

```
cgtctttctc ggctgggccc agaaaaggtt cggaaaacgc aacaccatct ggctgtttgg     1320
gccggccacc acgggcaaga ccaacatcgc ggaagccatc gcccacgccg tgcccttcta     1380
cggctgcgtc aactggacca atgagaactt tcccttcaac gattgcgtcg acaagatggt     1440
gatctggtgg gaggagggca agatgacggc caaggtcgtg gagtccgcca aggccattct     1500
cggcggcagc aaggtgcgcg tggaccaaaa gtgcaagtcg tccgcccaga tcgatcccac     1560
ccccgtgatc gtcacctcca acaccaacat gtgcgccgtg attgacggga cagcaccac      1620 cttcgagcac cagcagccgt tgcaggaccg gatgttcaaa tttgaactca cccgccgtct     1680
ggagcatgac tttggcaagg tgacaaagca ggaagtcaaa gagttcttcc gctgggcgca     1740
ggatcacgtg accgaggtgg cgcatgagtt ctacgtcaga aagggtggag ccaacaagag     1800
acccgccccc gatgacgcgg ataaaagcga gcccaagcgg gcctgcccct cagtcgcgga     1860
tccatcgacg tcagacgcgg aaggagctcc ggtggacttt gccgacaggt accaaaacaa     1920
atgttctcgt cacgcgggca tgcttcagat gctgtttccc tgcaaaacat gcgagagaat     1980
gaatcagaat ttcaacattt gcttcacgca cgggaccaga gactgttcag aatgtttccc     2040
cggcgtgtca gaatctcaac cggtcgtcag aaagaggacg tatcggaaac tctgtgccat     2100
tcatcatctg ctgggcggg ctcccgagat tgcttgctcg gcctgcgatc tggtcaacgt      2160
ggatctggat gactgtgttt ctgagcaata aatgacttaa accaggtatg gctgccgatg     2220
gttatcttcc agattggctc gaggacaacc tctctgaggg cattcgcgag tggtgggact     2280
tgaaacctgg agccccgaaa cccaaagcca accagcaaaa gcaggacgac ggccggggtc     2340
tggtgcttcc tggctacaag tacctcggac ccttcaacgg actcgacaag ggggagcccg     2400
tcaacgcggc ggatgcagcg gccctcgagc acgacaaggc ctacgaccag cagctcaaag     2460
cgggtgacaa tccgtacctg cggtataacc acgccgacgc cgagtttcag gagcgtctgc     2520
aagaagatac gtcttttggg ggcaacctcg ggcgagcagt cttccaggcc aagaagaggg     2580
ttctcgaacc ttttggtctg gttgaggaag gtgctaagac ggctcctgga agaaacgtc      2640 cggtagagca gtcgccacaa gagccagact cctcctcggg cattggcaag acaggccagc     2700
agcccgctaa aaagagactc aattttggtc agactggcga ctcagagtca gtccccgacc     2760
cacaacctct cggagaacct ccagcaaccc ccgctgctgt gggacctact acaatggctt     2820
caggcggtgg cgcaccaatg gcagacaata acgaaggcgc cgacggagtg ggtaatgcct     2880
caggaaattg gcattgcgat tccacatggc tgggcgacag agtcatcacc accagcaccc     2940
gaacatgggc cttgcccacc tataacaacc acctctacaa gcaaatctcc agtgcttcaa     3000 cggggggccag caacgacaac cactacttcg gctacagcac ccctgggg tatttttgatt      3060 tcaacagatt ccactgccat ttctcaccac gtgactggca gcgactcatc aacaacaatt     3120
ggggattccg gcccaagaga ctcaacttca agctcttcaa catccaagtc aaggaggtca     3180
cgacgaatga tggcgtcacg accatcgcta ataaccttac cagcacggtt caagtcttct     3240
cggactcgga gtaccagttg ccgtacgtcc tcggctctgc gcaccagggc tgcctccctc     3300
cgttcccggc ggacgtgttc atgattccgc agtacggcta cctaacgctc aacaatggca     3360
gccaggcagt gggacggtca tccttttact gcctggaata tttcccatcg cagatgctga     3420
gaacgggcaa taactttacc ttcagctaca ccttcgagga cgtgcctttc cacagcagct     3480
acgcgcacag ccagagcctg gaccggctga tgaatcctct catcgaccag tacctgtatt     3540
acctgaacag aactcagaat cagtccggaa gtgcccaaaa caaggacttg ctgtttagcc     3600
gggggtctcc agctggcatg tctgttcagc ccaaaaactg gctacctgga ccctgttacc     3660
```

```
ggcagcagcg cgtttctaaa acaaaaacag acaacaacaa cagcaacttt acctggactg   3720
gtgcttcaaa atataacctt aatgggcgtg aatctataat caaccctggc actgctatgg   3780
cctcacacaa agacgacaaa gacaagttct tcccatgag cggtgtcatg attttttggaa    3840 aggagagcgc cggagcttca aacactgcat tggacaatgt catgatcaca gacgaagagg   3900
aaatcaaagc cactaacccc gtggccaccg aaagatttgg gactgtggca gtcaatctcc   3960
agagcagcag cacagaccct gcgaccggag atgtgcatgt tatgggagcc ttacctggaa   4020
tggtgtggca agacagagac gtataccttgc agggtcctat ttgggccaaa attcctcaca   4080
cggatggaca ctttcacccg tctcctctca tgggcggctt tggacttaag cacccgcctc   4140
ctcagatcct catcaaaaac acgcctgttc ctgcgaatcc tccggcagag ttttcggcta   4200
caaagtttgc ttcattcatc acccagtatt ccacaggaca agtgagcgtg gagattgaat   4260
gggagctgca gaaagaaaac agcaaacgct ggaatcccga agtgcagtat acatctaact   4320
atgcaaaatc tgccaacgtt gatttcactg tggacaacaa tggactttat actgagcctc   4380 gcccccattgg caccgttac ctcacccgtc ccctgtaatt gtgtgttaat caataaaccg   4440
gttaattcgt gtcagttgaa ctttggtctc atgtcgttat tatcttatct ggtcaccata   4500
gcaaccggtt acacattaac tgcttagttg cgcttcgcga ataccctag tgatggagtt    4560 gcccactccc tctatgcgcg ctcgctcgct cggtggggcc ggcagagcag agctctgccg   4620
tctgcggacc tttggtccgc aggccccacc gagcgagcga gcgcgcatag agggagtggg   4680
caa                                                                  4683

<210> SEQ ID NO 30
<211> LENGTH: 4393
<212> TYPE: DNA
<213> ORGANISM: adeno-associated virus 8, complete genome
<220> FEATURE:
<221> NAME/KEY: misc_feature
<223> OTHER INFORMATION: NC_006261.1

<400> SEQUENCE: 30
cagagaggga gtggccaact ccatcactag gggtagcgcg aagcgcctcc cacgctgccg     60
cgtcagcgct gacgtaaatt acgtcatagg ggagtggtcc tgtattagct gtcacgtgag    120
tgcttttgcg gcatttttgcg acaccacgtg gccatttgag gtatatatgg ccagtgagc    180 gagcaggatc tccattttga ccgcgaaatt tgaacgagca gcagccatgc cgggcttcta    240
cgagatcgtg atcaaggtgc cgagcgacct ggacagcac ctgccgggca tttctgactc    300
gtttgtgaac tgggtggccg agaaggaatg ggagctgccc ccggattctg acatggatcg   360
gaatctgatc gagcaggcac ccctgaccgt ggccagaag ctgcagcgcg acttcctggt    420
ccaatggcgc cgcgtgagta aggccccgga ggccctcttc tttgttcagt tcgagaaggg   480
cgagagctac tttcacctgc acgttctggt cgagaccacg ggggtcaagt ccatggtgct   540
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg   660
ggggaacaag gtggtggacg agtgctacat ccccaactac ctcctgccca agactcagcc   720
cgagctgcag tgggcgtgga ctaacatgga ggagtatata agcgcgtgct tgaacctggc   780
cgagcgcaaa cggctcgtgg cgcagcacct gacccacgtc agccagaccg aggagcagaa   840
caaggagaat ctgaacccca attctgacgc gcccgtgatc aggtcaaaaa cctccgcgcg   900
ctatatggag ctggtcgggt ggctggtgga ccggggcatc acctccgaga agcagtggat   960
```

```
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc cgcggacat  tacccagaac cgcatctacc gcatcctcgc    1140
tctcaacggc tacgaccctg cctacgccgg ctccgtcttt ctcggctggg ctcagaaaaa    1200
gttcgggaaa cgcaacacca tctggctgtt tggacccgcc accaccggca agaccaacat    1260
tgcggaagcc atcgcccacg ccgtgccctt ctacggctgc gtcaactgga ccaatgagaa    1320
ctttcccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc caccccgtg  atcgtcacct ccaacaccaa    1500
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa aagacccgcc ccgatgacg  cggataaaag    1740 cgagcccaag cgggcctgcc cctcagtcgc ggatccatcg acgtcagacg cggaaggagc    1800
tccggtggac tttgccgaca ggtaccaaaa caaatgttct cgtcacgcgg gcatgcttca    1860
gatgctgttt ccctgcaaaa cgtgcgagag aatgaatcag aatttcaaca tttgcttcac    1920
acacggggtc agagactgct cagagtgttt ccccggcgtg tcagaatctc aaccggtcgt    1980
cagaaagagg acgtatcgga aactctgtgc gattcatcat ctgctggggc gggctcccga    2040
gattgcttgc tcggcctgcg atctggtcaa cgtggacctg gatgactgtg tttctgagca    2100
ataaatgact taaaccaggt atggctgccg atggttatct tccagattgg ctcgaggaca    2160
acctctctga gggcattcgc gagtggtggg cgctgaaacc tggagccccg aagcccaaag    2220
ccaaccagca aaagcaggac gacggccggg gtctggtgct tcctggctac aagtacctcg    2280
gacccttcaa cggactcgac aagggggagc ccgtcaacgc ggcggacgca gcggccctcg    2340
agcacgacaa ggcctacgac cagcagctgc aggcgggtga caatccgtac ctgcggtata    2400
accacgccga cgccgagttt caggagcgtc tgcaagaaga tacgtctttt ggggcaacc    2460 tcgggcgagc agtcttccag gccaagaagc gggttctcga acctctcggt ctggttgagg    2520
aaggcgctaa  cggctcct ggaaagaaga  ccggtaga  gccatcaccc cagcgttctc     2580
cagactcctc tacgggcatc ggcaagaaag gccaacagcc cgccagaaaa agactcaatt    2640
ttggtcagac tggcgactca gagtcagttc cagaccctca acctctcgga gaacctccag    2700
cagcgccctc tggtgtggga cctaatacaa tggctgcagg cggtggcgca ccaatggcag    2760
acaataacga aggcgccgac ggagtgggta gttcctcggg aaattggcat tgcgattcca    2820
catggctggg cgacagagtc atcaccacca gcacccgaac ctgggccctg cccacctaca    2880
acaaccacct ctacaagcaa atctccaacg ggacatcggg aggagccacc aacgacaaca    2940
cctacttcgg ctacagcacc ccctgggggt attttgactt taacagattc cactgccact    3000
tttcaccacg tgactggcag cgactcatca acaacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccagggct gcctgcctcc gttccgggcg acgtgttca    3240 tgattcccca gtacggctac ctaacactca acaacggtag tcaggccgtg ggacgctcct    3300
```

```
ccttctactg cctggaatac tttccttcgc agatgctgag aaccggcaac aacttccagt    3360
ttacttacac cttcgaggac gtgccttttcc acagcagcta cgcccacagc cagagcttgg    3420
accggctgat gaatcctctg attgaccagt acctgtacta cttgtctcgg actcaaacaa    3480
caggaggcac ggcaaatacg cagactctgg gcttcagcca aggtgggcct aatacaatgg    3540
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgtttttt tcccagtaac gggatcctga ttttggcaa acaaaatgct gccagagaca    3780
atgcggatta cagcgatgtc atgctcacca gcgaggaaga aatcaaaacc actaaccctg    3840
tggctacaga ggaataccgt atcgtggcag ataacttgca gcagcaaaac acggctcctc    3900
aaattggaac tgtcaacagc cagggggcct acccggtat ggtctggcag aaccgggacg    3960
tgtacctgca gggtcccatc tgggccaaga ttcctcacac ggacggcaac ttccacccgt    4020
ctccgctgat gggcggcttt ggcctgaaac atcctccgcc tcagatcctg atcaagaaca    4080
cgcctgtacc tgcggatcct ccgaccacct caaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                       4393

<210> SEQ ID NO 31
<211> LENGTH: 41
<212> TYPE: DNA
<213> ORGANISM: Artificial Sequence
<220> FEATURE:
<223> OTHER INFORMATION: SA EF1a splice acceptor

<400> SEQUENCE: 31 agttttttc ttccatttca ggtgtcgtga aaactacccc t                          41

<210> SEQ ID NO 32
<211> LENGTH: 13
<212> TYPE: DNA
<213> ORGANISM: Artificial Sequence
<220> FEATURE:
<223> OTHER INFORMATION: SD mIGHJ1/J4 splice donor

<400> SEQUENCE: 32
ctcctcaggt aag                                                       13

<210> SEQ ID NO 33
<211> LENGTH: 23
<212> TYPE: DNA
<213> ORGANISM: Artificial Sequence
<220> FEATURE:
<223> OTHER INFORMATION: IgHJ3 SD 98.84 splice donor

<400> SEQUENCE: 33
tgtctctgca ggtgagtcct aac                                            23

<210> SEQ ID NO 34
<211> LENGTH: 155
<212> TYPE: DNA
<213> ORGANISM: Artificial Sequence
```

<220> FEATURE:
<223> OTHER INFORMATION: Variant of IGH minimal promoter

<400> SEQUENCE: 34

```
ggtacctttt cattccttcc tctccagttc ttctctagat ggactaggtc cttaactagc    60
gaattcggat ccctgtctca tgaatatgca aatcaggtga gtccatggtg gtaaatatag   120
ggatgtcgac acacctcaca aacttaagat ctaga                              155
```

<210> SEQ ID NO 35
<211> LENGTH: 314
<212> TYPE: DNA
<213> ORGANISM: Artificial Sequence
<220> FEATURE:
<223> OTHER INFORMATION: IgK Minimal Promoter

<400> SEQUENCE: 35

```
ggcttgtgcc aaacatcttc tgggtggatt taggtgattg aggagaagaa agacacagga    60
gcgaaattct ctgagcacaa gggaggagtt ctacactcag actgagccaa cagacttttc   120
tggcctgaca accagggcgg cgcaggatgc tcagtgcaga gaggaagaag caggtggtct   180
ttgcagctga aagctcagct cccacccag ctgctttgca tgtccctccc agctgcccta    240
ccttccagag cccatatcaa tgcctgggtc agagctctgg ggaggaactg ctcagttagg   300
acccagacgg aacc                                                     314
```

<210> SEQ ID NO 36
<211> LENGTH: 28
<212> TYPE: DNA
<213> ORGANISM: Artificial Sequence
<220> FEATURE:
<223> OTHER INFORMATION: 12-RSS
<220> FEATURE:
<221> NAME/KEY: misc_feature
<222> LOCATION: (8)..(19)
<223> OTHER INFORMATION: n is a, c, g, or t

<400> SEQUENCE: 36

```
cacagtgnnn nnnnnnnna caaaaacc                                        28
```

<210> SEQ ID NO 37
<211> LENGTH: 39
<212> TYPE: DNA
<213> ORGANISM: Artificial Sequence
<220> FEATURE:
<223> OTHER INFORMATION: 23-RSS
<220> FEATURE:
<221> NAME/KEY: misc_feature
<222> LOCATION: (8)..(30)
<223> OTHER INFORMATION: n is a, c, g, or t

<400> SEQUENCE: 37

```
cacagtgnnn nnnnnnnnn nnnnnnnnnn acaaaaacc                            39
```

<210> SEQ ID NO 38
<211> LENGTH: 38
<212> TYPE: DNA
<213> ORGANISM: Artificial Sequence
<220> FEATURE:
<223> OTHER INFORMATION: 22-RSS
<220> FEATURE:
<221> NAME/KEY: misc_feature
<222> LOCATION: (8)..(29)
<223> OTHER INFORMATION: n is a, c, g, or t

<400> SEQUENCE: 38
cacagtgnnn nnnnnnnnnn nnnnnnnna caaaaacc        38

<210> SEQ ID NO 39
<211> LENGTH: 27
<212> TYPE: DNA
<213> ORGANISM: Artificial Sequence
<220> FEATURE:
<223> OTHER INFORMATION: 11-RSS
<220> FEATURE:
<221> NAME/KEY: misc_feature
<222> LOCATION: (8)..(18)
<223> OTHER INFORMATION: n is a, c, g, or t

<400> SEQUENCE: 39
cacagtgnnn nnnnnnnnac aaaaacc        27

<210> SEQ ID NO 40
<211> LENGTH: 29
<212> TYPE: DNA
<213> ORGANISM: Artificial Sequence
<220> FEATURE:
<223> OTHER INFORMATION: 13-RSS
<220> FEATURE:
<221> NAME/KEY: misc_feature
<222> LOCATION: (8)..(20)
<223> OTHER INFORMATION: n is a, c, g, or t

<400> SEQUENCE: 40
cacagtgnnn nnnnnnnnnn acaaaaacc        29

<210> SEQ ID NO 41
<211> LENGTH: 40
<212> TYPE: DNA
<213> ORGANISM: Artificial Sequence
<220> FEATURE:
<223> OTHER INFORMATION: 24-RSS
<220> FEATURE:
<221> NAME/KEY: misc_feature
<222> LOCATION: (8)..(31)
<223> OTHER INFORMATION: n is a, c, g, or t

<400> SEQUENCE: 41
cacagtgnnn nnnnnnnnn nnnnnnnnnn nacaaaaacc        40

<210> SEQ ID NO 42
<211> LENGTH: 108
<212> TYPE: DNA
<213> ORGANISM: Artificial Sequence
<220> FEATURE:
<223> OTHER INFORMATION: Line 1 of Fig 17A: IgK-V3-15 Sense strand, the
      Mouse IgK-J (any of J1, J2, J4, J5, that may be any sequence
      denoted herein as N for any nucleotide, in the middle block of
      line 1) and Mouse IgK-Constant Sense strand
<220> FEATURE:
<221> NAME/KEY: misc_feature
<222> LOCATION: (38)..(76)
<223> OTHER INFORMATION: n is a, c, g, or t

<400> SEQUENCE: 42
cagtttatta ctgtcagcag tataataact ggcctccnnn nnnnnnnnn nnnnnnnnn        60 nnnnnnnnnn nnnnnngggc tgatgctgca ccaactgtat ccatcttc        108

<210> SEQ ID NO 43
<211> LENGTH: 108
<212> TYPE: DNA
<213> ORGANISM: Artificial Sequence
<220> FEATURE:
<223> OTHER INFORMATION: Line 2 of Fig 17A: IgK-V3-15 anti-Sense strand,
      the Mouse IgK-J (any of J1, J2, J4, J5, that may be any sequence denoted herein as N for any nucleotide, in the middle block of
line 1) and Mouse IgK-Constant Sense strand
<220> FEATURE:
<221> NAME/KEY: misc_feature
<222> LOCATION: (38)..(76)
<223> OTHER INFORMATION: n is a, c, g, or t

<400> SEQUENCE: 43
gtcaaataat gacagtcgtc atattattga ccggaggnnn nnnnnnnnn nnnnnnnnn    60 nnnnnnnnnn nnnnnnccccg actacgacgt ggttgacata ggtagaag              108

<210> SEQ ID NO 44
<211> LENGTH: 27
<212> TYPE: PRT
<213> ORGANISM: Artificial Sequence
<220> FEATURE:
<223> OTHER INFORMATION: Line 3 of Fig 17A: putative encoded amino acid
      sequence of the IgK-V3-15, the Mouse IgK-J (any of J1, J2, J4, J5,
      that may be any sequence denoted herein as X for any amino acid
      residue, in the middle block of line 1) and Mouse IgK-Constant
      Sense strand
<220> FEATURE:
<221> NAME/KEY: MISC_FEATURE
<222> LOCATION: (14)..(26)
<223> OTHER INFORMATION: x is any amino acid residue

<400> SEQUENCE: 44

Ala Val Tyr Tyr Cys Gln Gln Tyr Asn Asn Trp Pro Pro Xaa Xaa Xaa
1               5                   10                  15

Xaa Xaa Xaa Xaa Xaa Xaa Xaa Xaa Xaa Xaa Gly
            20                  25

<210> SEQ ID NO 45
<211> LENGTH: 35
<212> TYPE: DNA
<213> ORGANISM: Artificial Sequence
<220> FEATURE:
<223> OTHER INFORMATION: Line 4 of Fig 17A: IgK-V3-15 Sense strand at
      the left block of the figure

<400> SEQUENCE: 45
cagtttatta ctgtcagcag tataataact ggcct                              35

<210> SEQ ID NO 46
<211> LENGTH: 32
<212> TYPE: DNA
<213> ORGANISM: Artificial Sequence
<220> FEATURE:
<223> OTHER INFORMATION: Line 4 of Fig 17A: Mouse IgK-Constant Sense
      strand at the right block of the figure. also the left part of
      lines 5 and 6

<400> SEQUENCE: 46
gggctgatgc tgcaccaact gtatccatct tc                                 32

<210> SEQ ID NO 47
<211> LENGTH: 34
<212> TYPE: DNA
<213> ORGANISM: Artificial Sequence
<220> FEATURE:
<223> OTHER INFORMATION: Line 5 of Fig 17A: Left part of coding joint #1

<400> SEQUENCE: 47
cagtttatta ctgtcagcag tataataact ggcc                               34

<210> SEQ ID NO 48
<211> LENGTH: 38

```
<212> TYPE: DNA
<213> ORGANISM: Artificial Sequence
<220> FEATURE:
<223> OTHER INFORMATION: Line 5 of Fig 17A: Middle part of coding joint
      #1

<400> SEQUENCE: 48
gctcacgttc ggtgctggga ccaagctgga gctgaaac                              38

<210> SEQ ID NO 49
<211> LENGTH: 36
<212> TYPE: DNA
<213> ORGANISM: Artificial Sequence
<220> FEATURE:
<223> OTHER INFORMATION: Line 6 of Fig 17A: Left part of coding joint #2

<400> SEQUENCE: 49
cagtttatta ctgtcagcag tataataact ggcctc                                36

<210> SEQ ID NO 50
<211> LENGTH: 36
<212> TYPE: DNA
<213> ORGANISM: Artificial Sequence
<220> FEATURE:
<223> OTHER INFORMATION: Line 6 of Fig 17A: Middle part of coding joint
      #2

<400> SEQUENCE: 50
gcacgttcgg ctcggggaca aagttggaaa taaaac                                36

<210> SEQ ID NO 51
<211> LENGTH: 314
<212> TYPE: DNA
<213> ORGANISM: Artificial Sequence
<220> FEATURE:
<223> OTHER INFORMATION: IgK "Minimal Promoter

<400> SEQUENCE: 51
ggcttgtgcc aaacatcttc tgggtggatt taggtgattg aggagaagaa agacacagga      60
gcgaaattct ctgagcacaa gggaggagtt ctacactcag actgagccaa cagactttc     120 tggcctgaca accagggcgg cgcaggatgc tcagtgcaga gaggaagaag caggtggtct    180
ttgcagctga agctcagct cccaccccag ctgctttgca tgtccctccc agctgcccta     240
ccttccagag cccatatcaa tgcctgggtc agagctctgg ggaggaactg ctcagttagg    300
acccagacgg aacc                                                      314
```

The invention claimed is:

1. A method for targeted insertion of at least one nucleic acid sequence of interest into a target genomic locus of a mammalian cell, said method comprises the step of contacting a mammalian cell expressing the recombination activating gene (RAG) complex with at least one nucleic acid cassette comprising said nucleic acid sequence/s of interest and at least one recognition signal sequence (RSS), or with a vector comprising the same, wherein the insertion of said nucleic acid sequence of interest into the target genomic locus is mediated by RAG-catalyzed recombination between at least one genomic RSS flanking the target genomic locus and at least one RSS comprised within said nucleic acid cassette.

2. The method according to claim 1, wherein said nucleic acid cassette is flanked on both the 5' and 3' ends thereof by RSS, optionally, said RSS are at least one of 12 RSS, 23 RSS and 22 RSS.

3. The method according to claim 1, wherein said nucleic acid sequence of interest is a protein coding nucleic acid sequence or a non-coding nucleic acid sequence.

4. The method according to claim 3, wherein said nucleic acid sequence of interest encodes at least one of a receptor and an antibody or any fragment/s or chimera/s thereof, optionally, wherein at least one of:
   (a) said nucleic acid sequence of interest encodes at least one receptor, said receptor is any one of: a T cell receptor (TCR), chimeric antigen receptor (CAR) and a B cell receptor (BCR);
   (b) said nucleic acid sequence of interest encodes at least one antibody, said antibody is any one of: full length antibody, antibody fragment, single-chain variable fragment (scFv), bi-specific antibody, tri-specific antibody, Bi-specific T-cell engagers (BiTE) and variable new antigen receptor antibody (V-NAR); and (c) said nucleic acid cassette comprises a nucleic acid sequence encoding a secreted antibody specific for an autoantigen and a BCR specific for a foreign antigen.

5. The method according to claim 1, wherein said target genomic locus is at least one of Immunoglobulin heavy chain locus, Immunoglobulin κ chain locus, Immunoglobulin λ chain locus, TCRβ chain locus, TCRα chain locus, TCRγ chain and the TCRδ chain locus.

6. The method according to claim 1, wherein said cassette is comprised within a nucleic acid vector, said vector is any one of a viral vector, a non-viral vector and a naked DNA vector.

7. The method according to claim 1, wherein said mammalian cells is any one of a naturally RAG expressing cell, stably RAG expressing cell, inducibly RAG expressing cell and a cell transfected with RAG expression vector/s, optionally, said cell is any one of a lymphocyte progenitor, ex vivo differentiating lymphocytes, hematopoietic stem and progenitor cells (HSPCs) and Induced pluripotent stem cells (iPSCs), optionally, said lymphocyte progenitor is any one of a T cell progenitor, a B cell progenitor and an NK cell progenitor.

8. The method according to claim 1, for targeted insertion of at least one nucleic acid sequence of interest into a target genomic locus of a cell in a mammalian subject, the method comprising administering to said subject an effective amount of at least one nucleic acid cassette comprising said nucleic acid sequence of interest and at least one RSS, or of a vector comprising said cassette, wherein the insertion of said nucleic acid sequence of interest into the target genomic locus is mediated by RAG-catalyzed recombination between at least one genomic RSS flanking the target genomic locus and at least one RSS comprised within said nucleic acid cassette, optionally, said cassette further comprises at least one genetic element, said genetic element is at least one of: an IRES, a 2A peptide coding sequence, a promoter or any functional fragments thereof, a splice donor (SD), a splice acceptor (SA), a degron, a 3 frame stop, a protein stabilizing sequence, a signal peptide, a stop codon, a polyadenylation site, a splice donor, a transcription enhancer, a switch region, an mRNA stabilizing sequence and a protein stabilizing sequence.

9. The method according to claim 8, wherein said nucleic acid sequence of interest is a protein coding nucleic acid sequence or a non-coding nucleic acid sequence, wherein optionally, said nucleic acid sequence of interest encodes at least one of a receptor and an antibody or any fragment/s or chimera/s thereof, optionally, said target genomic locus is at least one of Immunoglobulin heavy chain locus, Immunoglobulin κ chain locus, Immunoglobulin λ chain locus, TCRβ chain locus, TCRα chain locus, TCRγ chain and the TCRδ chain locus.

10. The method according to claim 8, wherein at least one of:
(a) said cassette is comprised within a nucleic acid vector, said vector is any one of a viral vector, a non-viral vector and a naked DNA vector;
(b) said cell is any one of Thymocytes, HSPCs and mobilized HSPCs; and
(c) said subject is a subject suffering from an immune-related disorder.

11. The method according to claim 2, wherein said cassette further comprises at least one genetic element, said genetic element is at least one of: an internal ribosome entry site (IRES), a 2A peptide coding sequence, a promoter or any functional fragments thereof, a splice donor (SD), a splice acceptor (SA), a degron, a 3 frame stop, a protein stabilizing sequence, a signal peptide, a stop codon, a polyadenylation site, a transcription enhancer, a switch region, an mRNA stabilizing sequence and a protein stabilizing sequence, optionally, said cassette comprises two or more nucleic acid sequences of interest separated by at least one genetic element, said genetic element is at least one of: an IRES, a 2A peptide coding sequence, a promoter or any functional fragments thereof, a splice donor (SD) and a splice acceptor (SA).

12. The method according to claim 3, wherein:
(a) said nucleic acid sequence of interest is a protein coding sequence, said protein is at least one of: a therapeutic protein or peptide, a prophylactic protein, a tolerizing protein, an immunizing protein, a toxic protein, a suicide protein, a marker protein, an imaging protein and a fusion or chimeric protein; or
(b) said nucleic acid sequence of interest encodes at least one small non-coding RNA molecule.

13. The method according to claim 6, wherein:
(a) said vector is a viral vector, said viral vector is any one of recombinant adeno associated vectors (rAAV), single stranded AAV (ssAAV), self-complementary rAAV (scAAV), Simian vacuolating virus 40 (SV40) vector, Adeno virus vector, helper-dependent Adeno viral vector, retroviral vector and lentiviral vector; or
(b) said vector is a non-viral vector, said vector is any one of plasmid, minicircle and linear DNA; or
(c) said vector is a naked DNA vector, said vector is any one of plasmid, minicircle and linear DNA.

\* \* \* \* \*